US007439067B2

(12) United States Patent
Lasure et al.

(10) Patent No.: US 7,439,067 B2
(45) Date of Patent: Oct. 21, 2008

(54) ISOLATED POLYNUCLEOTIDES AND METHODS OF PROMOTING A MORPHOLOGY IN A FUNGUS

(75) Inventors: Linda L. Lasure, Fall City, WA (US); Ziyu Dai, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 459 days.

(21) Appl. No.: 10/442,017

(22) Filed: May 19, 2003

(65) Prior Publication Data

US 2003/0215950 A1 Nov. 20, 2003

Related U.S. Application Data

(60) Provisional application No. 60/382,132, filed on May 20, 2002.

(51) Int. Cl.
*C12N 15/80* (2006.01)
*C12P 7/48* (2006.01)

(52) U.S. Cl. .................................. 435/471; 435/144
(58) Field of Classification Search .................. None
See application file for complete search history.

(56) References Cited

U.S. PATENT DOCUMENTS

| 5,532,148 | A | 7/1996 | Datta et al. |
| 5,643,745 | A | 7/1997 | Stuart |
| 5,821,104 | A | 10/1998 | Holm et al. |
| 5,912,153 | A * | 6/1999 | Selitrennikoff et al. ...... 435/193 |
| 5,973,131 | A | 10/1999 | Cao et al. |
| 6,902,887 | B1 | 6/2005 | Berka et al. |
| 2003/0045697 | A1 | 3/2003 | Akin et al. |
| 2004/0044193 | A1 * | 3/2004 | Schroppel et al. .......... 536/23.1 |
| 2005/0064403 | A1 | 3/2005 | Edens et al. |

FOREIGN PATENT DOCUMENTS

| EP | 0955363 A2 | 11/1999 |
| EP | 1384782 A1 | 1/2004 |
| WO | 9509459 A1 | 2/1995 |
| WO | 9943271 A1 | 9/1999 |
| WO | WO 00/56762 | 9/2000 |
| WO | WO 02086090 A2 | 10/2002 |
| WO | 03054186 A1 | 7/2003 |

OTHER PUBLICATIONS

Prokisch, H. et al., Imparment of calcineurin function in *Neurospora crassa* reveals the essential role in hyphal growth, morphology and maintenance of the apical Ca2+ gradient, Molecular General Genetics 256: 104-114, 1997.*
Branch, A.D., A good antisense molecule is hard to find, Trends Biochem. Sci. 23(2): 45-50, 1998.*
Kano R. et al. Repeated Ubiquitin Genes in Trichophyton Mentagrophytes. Current Microbiology. Nov. 1999, vol. 39, pp. 302-305.

Diatchenko, L. et al., "Suppression subtractive hybridization: A method for generating differentially regulated or tissue-specific cDNA probes and libraries" Proc. Natl. Acad. Sci., vol. 93, pp. 6025-6030, Jun. 1996, Biochemistry.
Chomczynski, P. et al., "Single-Step Method of RNA Isolation by Acid Guanidinium Thiocyanate-Phenol-Choloroform Extraction", Analytical Biochemistry, vol. 162, pp. 156-159, 1987.
Punt, P. et al., "Transformation of Filamentous Fungi Based on Hygromycin B and Phleomycin Resistance Markers", Methods in Enzymology, vol. 216, pp. 447-457, 1992.
An, G. et al., "Plant Molecular Biology Manual"A3/1-19, 1988.
Ebert, P. et al."Identification of an essential upstream element in the nopaline sythase promoter by stable and transient assays", Proc. Natl. Acad. Sci., vol. 84, pp. 5745-5749, Aug. 1987, Botany.
Groot, M. et al., "Agrobacterium tumefaciens-mediated transformation of filamentous fungi", Nature Biotechnology, vol. 16, pp. 839-842, Sep. 1998.
Agger, T. et al., "Growth and Product Formation of *Aspergillus oryzae* during Submerged Cultivations: Verification of a Morphologically Structured Model Using Fluorescent Probes", Biotechnology and Bioengineering. vol. 57, No. 3, Feb. 5, 1998. pp. 321-329.
Gibbs, P. et al., "Growth of Filamentous Fungi in Submerged Culture: Problems and Possible Solutions", Critical Reviews in Biotechnology, 20(1):17-48 (2000).
Johansen, C. et al., "Influence of Morphology on Product Formation in *Aspergillus awamori* during Submerged Fermentations", Biotechnol. Prog., 1998, 14, 233-240.
Kossen, "The Morphology of Filamentous Fungi", Advances in Biochemical Engineering/Biotechnology, vol. 70, pp. 1-33, 2000.
Moreira, M. et al., "Control of pellet morphology of filamentous fungi in fluidized bed bioreactors by means of a pulsing flow", Enzyme and Microbial Technology 19:261-266, 1996.
Schugerl, K. et al., "Influence of the Process Parameters on the Morphology and Enzyme Production of *Aspergilli*", Advances in Biochemical Engineering/Biotechnology, vol. 60:195-266, 1998.
Altschul, S. et al., " Gapped Blast and Psi-Blast: a new generation of protein database search programs", Nucleic Acids Research, 1997, vol. 25, No. 17, 3389-3402.
Pazouki, M. et al., "Understanding the morphology of fungi", Bioprocess Engineering, vol. 22. 2000. pp. 127-143.
Bowman S et al., "The Nucleotide Sequence of Saccharomyces Cervisiae Chromosome XIII", Nature, Nature Publishing Group, London GB, vol. 387, No. 6632, May 29, 1997, pp. 90-93.
Galagan J E et al., "The genome sequence of the filamentous fungus *Neurospora crassa*", Nature, Nature Publishing Group, London GB, vol. 422, No. 6934, Apr. 24, 2003, pp. 859-868.

(Continued)

*Primary Examiner*—Nancy Vogel
(74) *Attorney, Agent, or Firm*—Wells St. John P.S.

(57) ABSTRACT

The invention includes isolated polynucleotide molecules that are differentially expressed in a native fungus exhibiting a first morphology relative to the native fungus exhibiting a second morphology. The invention includes a method of enhancing a bioprocess utilizing a fungus. A transformed fungus is produced by transforming a fungus with a recombinant polynucleotide molecule. The recombinant polynucleotide molecule contains an isolated polynucleotide sequence linked operably to a promoter. The polynucleotide sequence is expressed to promote a first morphology. The first morphology of the transformed fungus enhances a bioprocess relative to the bioprocess utilizing a second morphology.

2 Claims, 16 Drawing Sheets

OTHER PUBLICATIONS

Teumer J et al., "Divergent evolution of part of the involucrin gene in the hominoids: Unique intragenic duplications in the gorilla and human", Proceedings of the National Academy of Sciences of the USA, vol. 86, No. 4, 1989, pp. 1283-1286.

Ruzzi M et al., "The sequence of a 8kb segment on the right arm of yeast chromosome VII identifies four new open reading frames and the gene for yTAF-II145", Yeast, vol. 13, No. 4, 1997, pp. 365-368.

Database EMBL [Online] Sep. 20, 2000, XP002417447, Database accession No. BE760518.

Database EMBL [Online] Sep. 20, 2000, XP002417448, Database accession No. BE760857.

Wood V et al., "The genome sequence of Schizosaccharomyces pombe", Nature, Nature Publishing Group, London GB, vol. 415, No. 6874, Feb. 21, 2002, pp. 871-880.

Database UniProt [Online] Jun. 1, 2001, XP002417449, Database accession No. Q9C118.

Loser Karin et al., "Induction of a polyubiquitin gene (ubi1) by potato phytoalexins and heat shock in Gibberella pulicaris", Current Genetics, vol. 34, No. 5, Dec. 1998, pp. 404-409.

Wang J et al., "Structure, expression and promoter activity of two polyubiquitin genes from rice (Oryza sativa L.)", Plant Science, Limerick IE, vol. 156, No. 2, Jul. 28, 2000, pp. 201-211.

Rosen S et al., "The Aspergillus nidulans sfaD gene encodes a G protein beta subunit that is required for normal growth and repression of sporulation", EMBO (European Molecular Biology Organization) Journal, vol. 18, No. 20, Oct. 15, 1999, pp. 5592-5600.

Schoffelmeer E A M et al., "FEM1, a Fusarium oxysporum glycoprotein that is covalently linked to the cell wall matrix and is conserved in filamentous fungi" MGG Molecular Genetics and Genomics, vol. 265, No. 1, Mar. 2001, pp. 143-152.

Ilg T et al., "Molecular cloning and characterization of a novel repeat-containing Leishmania major gene, ppg1, that encodes a membrane-associated form of proteophosphoglycan with a putative glycosylphosphatidylinositol anchor", Journal of Biological Chemistry, vol. 274, No. 44, Oct. 1999, pp. 31410-31420.

Yoshida K T et al., "Temporal and spatial patterns of accumulation of the transcript of myo-inositol-1-phosphate synthase and phytin-containing particles during seed development in rice", Plant Physiology (Rockville), vol. 119, No. 1, Jan. 1999, pp. 65-72.

* cited by examiner

FIG. 1

```
Query:   1   MADMSGEQMQAKITAARREAEGLKDKIKRRKDELADTTLRQVAQNQTETLPRIGMKPRRT   60
             MADMSGEQMQAKITAARREAEGLKDKI+RRKD+LADTTLR VAQNQT+ LPRIGMKPRRT
Sbjct:   1   MADMSGEQMQAKITAARREAEGLKDKIRRRKDDLADTTLRDVAQNQTDALPRIGMKPRRT   60

Query:  61   LKGHLAKIYAMHWSTDRRHLVSASQDGKLIIWDAYTTNKVHAIPLRSSWVMTCAYAPSGN  120
             LKGHLAKIYAMHWSTDRRHLVSASQDGKLIIWDAYTTNKVHAIPLRSSWVMTCAYAPSGN
Sbjct:  61   LKGHLAKIYAMHWSTDRRHLVSASQDGKLIIWDAYTTNKVHAIPLRSSWVMTCAYAPSGN  120

Query: 121   YVACGGLDNICSIYNLSSREGPTRVARELSGHSGYLSCCRFINDRRIITSSGDMTCMLWD  180
             YVACGGLDNICSIYNLSSREGPTRVARELSGHSGYLSCCRFINDRRIITSSGDMTCMLWD
Sbjct: 121   YVACGGLDNICSIYNLSSREGPTRVARELSGHSGYLSCCRFINDRRIITSSGDMTCMLWD  180

Query: 181   IESGSKVTEFADHLGDVMSISINPTNQNVFVSGACDAFAKLWDIRTGKAVQTFAGHESDI  240
             IESGSKVTEFADH GDVMSISINPTNQN+FVSGACDAFAKLWDIRTGKAVQTFAGHESDI
Sbjct: 181   IESGSKVTEFADHIGDVMSISINPTNQNIFVSGACDAFAKLWDIRTGKAVQTFAGHESDI  240

Query: 241   NAIQFFPDGNAFGTGSDDTSCRLFDIRADRELNTYQSDQILCGITSVAFSVSGRLLFAGY  300
             NAIQFFPDGNAFGTGSDDT+CRLFDIRADR LNTYQSDQILCGITSV FSVSGRLLFAGY
Sbjct: 241   NAIQFFPDGNAFGTGSDDTICRLFDIRADRSLNTYQSDQILCGITSVGFSVSGRLLFAGY  300

Query: 301   DDFECKVWDVLRGDKVGSLSGHENRVSCLGVSNDGISLCTGSWDSLLKVWAW  352
             DDFECKVWDVLRGDKVGSLSGHENRVSCLGVSNDGISLCTGSWDSLLKVWAW
Sbjct: 301   DDFECKVWDVLRGDKVGSLSGHENRVSCLGVSNDGISLCTGSWDSLLKVWAW
```

```
Query:  29  VPSGWHHVEDAGSDHQISLSIALARKNLDQLESKLKDLSTPGESQYGQWLDQEDV-DTLF  87
            +P GW   + A  + ++SL+ AL ++N+++L   ++ +S P   QYG++L E+V D +
Sbjct:  31  LPPGWVSLGRADPEEELSLTFALRQQNVERLSELVQAVSDPSSPQYGKYLTLENVADLVR  90

Query:  88  PVA-SDKAVINWLRSANIT--HISRQGSLVNFATTVDKVNKLL-NATFAYYQSGSSQR--  141
            P   +  V WL +A     H        ++ +    LL  A F +Y  G ++
Sbjct:  91  PSPLTLHTVQKWLLAAGAQKCHSVITQDFLTCWLSIRQAELLLPGAEFHHYVGGPTETHV  150

Query:  142 LRTTE-YSIPDDLVDSIDLISPTTFFGKEKTTAGLNQRAQKIDNHVAKRSNSSSCADLIT  200
            +R+    Y +P   L +D +       F     T+ L QR +        + + +  +T
Sbjct:  151 VRSPHPYQLPQALAPHVDFVGGLHHF---PPTSSLRQRPE------PQVTGTVGLHLGVT  201

Query:  201 LSCLKEMYNFGNYTPSASSGSKLGFGSFLNESASY-SDLAKFEKLF--NLPSQSFSVELV  257
             S ++  YN  +                  E   + SDLA+F +LF  N   Q+ SV V
Sbjct:  202 PSVIRKRYNLTSQDVGSGTSNNSQACAQFLEQYFHDSDLAQFMRLFGGNFAHQA-SVARV  260

Query:  258 NGGVNDQNQSTASLTEADLDVELLVGVAHPLPVTEFITSGEPPFIPDPDEPSAADNENEP  317
              V Q +   A  + EA LDV+ L+    +     + +G           EP
Sbjct:  261 ---VGQQGRGRAGI-EASLDVQYLMSAGANISTWVYSSPGR-------------HEGQEP  303

Query:  318 YLQYYEYLLSKPNSALPQVISNSYGDDEQTVPEYYAKRVCNLTGLVGLRGISVLESSGDE  377
            +LQ++  +L    SALP V + SYGDDE  ++   Y +RV        RG+++L +SGD
Sbjct:  304 FLQW--LMLLSNESALPHVHTVSYGDDEDSLSSAYIQRVWTELMKAAARGLTLLFASGDS  361

Query:  378 GIGSGCRTTDGTNRTQFNPIFPATCPYVTAVGGTMSYAP-----EIAWEASGGFSNYFE  432
            G+GC + G R QF P FPA+ PYVT VGGT   P     EI   S GGFSN F
Sbjct:  362 --GAGCWSVSG--RHQFRPTFPASSPYVTTVGGTSFQEPFLITNEIVDYISGGGFSNVFP  417

Query:  433 RAWFQKEAVQNYLAHHITNETKQYYSQFANFSGRGFPDVAAHSFEPSYEVIFYGARYG-S  491
            R  +Q+EAV +L+         Y+   N SGR +PDVAA S    Y V+
Sbjct:  418 RPSYQEEAVTKFLSSSPHLPPSSYF----NASGRAYPDVAALS--DGYWVVSNRVPIPWV  471

Query:  492 GGTSAACPLFSALVGMLNDARLRAGKSTLGFLNPLLYSKGYRALTDVTGGQSIGCNGIDP  551
            GTSA+ P+F ++ ++N+ R+ +G+   LGFLNP LY +   L DVT G   C
Sbjct:  472 SGTSASTPVFGGILSLINEHRILSGRPPLGFLNPRLYQQHGAGLFDVTRGCHESC-----  526

Query:  552 QNDETVAGAGIIPWAHWNATVGWDPVTGLGLPDFEKLRQLVLS  594
             DE V G G     +    GWDPVTG G P+F L + +L+
Sbjct:  527 -LDEEVEGQGFC------SGPGWDPVTGWGTPNFPALLKTLLN  562
```

FIG. 6

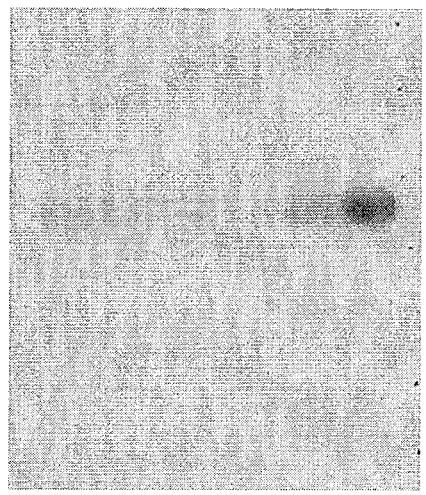

```
Query:   26 FTVNSPNVVYTDMEIRSQYAYHTTIDITRTADN---KLVATPKATNYHFKVDRKVGKVGVM  82
             F V SPNV YT+ EI S Y Y TT++   + N   + +  PK   Y FK D
Sbjct:    6 FKVESPNVKYTEGEIHSVYNYETTELVHESRNGTYQWIVKPKTVKYEFKTDTHVPKLGVM  65

Query:   83 MVGWGGNNGSTVT-QVSLPTAVVSNGRPRAMRASNYYGSVVMGSTIKLGTDAKTGEEINI 141
              ST+T V      +S       ++ +NY+GS+   S+I++G+     GEEI
Sbjct:   66 LVGWGGNNGSTLTGGVIANREGISWATKDKVQQANYFGSLTQASSIRVGS--FNGEEIYA 123

Query:  142 PFHDMLPMVHPNDLAIGGWDISSLNLADSMDRAQVLEPTLKQQVRKEMAEMKPLPSIYYP 201
             PF  +LPMV+P+D+  GGWDIS++NLAD+M RA+VL+   L++Q+R  M  M PLP IY P
Sbjct:  124 PFKSLLPMVNPDDVVFGGWDISNMNLADAMGRAKVLDIDLQKQLRPYMEHMVPLPGIYDP 183

Query:  202 DFIAANQEDRADNVLEGSKACWAHVEKIQQDIRDFKAQNGLDKVIVMWTANTERYADILP 261
             DFIAANQ  RA+NV++G+K      V++I +D+RDFK QN +DKV+V+WTANTERY+++
Sbjct:  184 DFIAANQGSRAMNVIKGTKK--EQVQQIIKDMRDFKEQNKVDKVVVLWTANTERYSNVVV 241

Query:  262 GVNDTADNLLNAIKTGHLEVSPSTVFAVACILDNVPFINGSPQNTFVPGAIQLAEQHKAF 321
             G+NDTA++L+ +++    E+SPST++A+AC+ +NVPFINGSPQNTFVPG I LA Q +
Sbjct:  242 GLNDTAESLMASVERNEAEISPSTLYAIACVFENVPFINGSPQNTFVPGLIDLAIQRNSL 301

Query:  322 IGGDDFKSGQTKMKSALVDFLINAGIKLTSIASYNHLGNMDGKNLSSQKQFRSKEISKSN 381
             IGGDDFKSGQTKMKS LVDFL+ AGIK TSI SYMHLGNMDG NLS+ + FRSKEISKSN
Sbjct:  302 IGGDDFKSGQTKMKSVLVDFLVGAGIKPTSIVSYMHLGNMDGMNLSAPQTFRSKEISKSN 361

Query:  382 VVDDMVAANKILYAEDEHPDHTVVIKYMPAVGDNKRALDEYYAEIFMGGHQTISLFNICE 441
             VVDDMVA+N ILY   EHPDH VVIKY+P VGD+KRA+DEY +EIFMGG  TI L N CE
Sbjct:  362 VVDDMVASNGILYEPGEHPDHIVVIKYVPYVGDSKRAMDEYTSEIFMGGKSTIVLHNTCE 421

Query:  442 DSLLASPLIIDLVLIAEMMTRISWKSDEAAEYKGFHSVLSVLSYMLKAPLTPPGTPVVNS 501
             DSLLA+P+I+DLVL+AE+ TRI K++   ++  FH V ++LSY+ KAPL PPGTPVVN+
Sbjct:  422 DSLLAAPIILDLVLLAELSTRIQLKAEGEGKFHSFHPVATILSYLTKAPLVPPGTPVVNA 481

Query:  502 LTKQRSALTNIFRACVGLQPESEMTLEHK 530
             L+KQR+ L NI RACVGL PE+ M LE+K
Sbjct:  482 LSKQRAMLENILRACVGLAPENMMILEYK 510
```

FIG. 4B

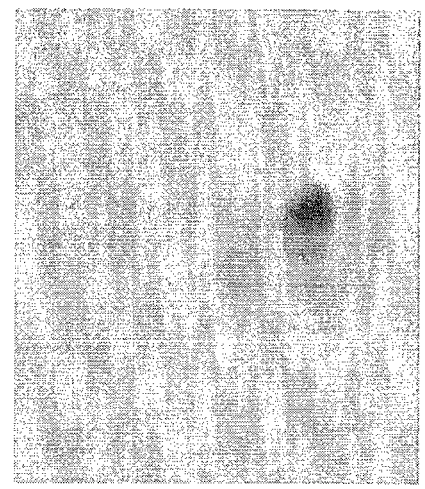

```
Query:   1   MAARPQNIGIKAIEVYFPRQCVDQSELEKFDGVSEGKYTIGLGQTKMSFCDDREDIYSIA 60
             MA RPQNIGIKAIE+YFP Q V+QSELEKFDGVS GKYTIGLGQTKM+FCDDREDIYS+A
Sbjct:   1   MATRPQNIGIKAIEIYFPSQYVEQSELEKFDGVSTGKYTIGLGQTKMAFCDDREDIYSLA 60

Query:  61   LTTFSSLLRKYNIDPNSIGRLEVGTETLLDKSKSVKSVLMQLLAPHGNTNVEGVDNVNAC 120
             LT  S LL+ Y ID N+IGRLEVGTETLLDKSKSVKSVLMQL     NTN+EGVD +NAC
Sbjct:  61   LTAVSRLLKNYEIDTNTIGRLEVGTETLLDKSKSVKSVLMQLFGE--NTNIEGVDTINAC 118

Query: 121   CGGTNAVFNSINWLESSAWDGRDAVVVCGDIALYAEGAARPTGGAGCVAMLIGPDAPIVF 180
               GGTNA FNS+NW+ESSAWDGRDA+VV GDIALYA+G ARPTGGAGCVAML+GP+API
Sbjct: 119   YGGTNAFFNSVNWIESSAWDGRDAIVVAGDIALYAKGNARPTGGAGCVAMLVGPNAPIAV 178

Query: 181   EPGLRASYVTHAYDFFKPDLTSEYPVVDGHFSLRCYTEAVNACYKAYNAREKTLKEKVQN 240
             EPGLR SY+ HAYDF+KPDLTSEYP VDGH+S+ CYTEA++  Y+AYN REK L    N
Sbjct: 179   EPGLRGSYMAHAYDFYKPDLTSEYPYVDGHYSVNCYTEALDGAYRAYNQREKLL----TN 234

Query: 241   GTNGTAQDDSQTALDRFEYLCYHAPTCKLVQKSFARMLYNDYLTNPTHPAFAEVAPELRD 300
             G NG ++D ++T LDRF+YL +HAPTCKLVQKS +AR+LY+DYL NP   P FA+V PE+RD
Sbjct: 235   GVNGHSEDSTKTPLDRFDYLAFHAPTCKLVQKSYARLLYHDYLANPESPVFADVPPEVRD 294

Query: 301   LDYATSLTDKNVEKTFMGLTKKRFAERVKPALEVATLCGNMYTATVWAGLASLISHVPFD 360
             +DY  SLTDK VEKTFM LTKKRF ERV PA++V TLCGNMY  +VW GLAS+I HV
Sbjct: 295   MDYKKSLTDKVVEKTFMTLTKKRFQERVNPAIQVPTLCGNMYCGSVWGGLASIIGHVDSA 354

Query: 361   ASESKRIGLFSYGSGLASSLLSVKIVGDVSNLVEKLDLKNRLSNRNVLPPQSYVDMCALR 420
                E KRIGLFSYGSGLA+S   ++  G   L + L+L  RL+ R  +PP+SY MC LR
Sbjct: 355   QLEGKRIGLFSYGSGLAASFCSFRVTGSTEKLAKTLNLPARLAARRAVPPESYDAMCDLR 414

Query: 421   EHAHLKKNFKPSGNTETLYPGTYYLTEVDDMFRRKYDVKA 460
             + AHL+KN+ P G   TL PGTYYL VDDMF+R Y +KA
Sbjct: 415   KQAHLQKNYTPKGEVSTLEPGTYYLENVDDMFKRTYSIKA 454
```

```
Query:    70 VLRLRGGMQIFVKTLTGKTITLEVESSDTIDNVKTKIQDKEGIPPDQQRLIFAGKQLEDG 129
             VLR    + +  VKTLTGKTITLEVESSDTIDNVKTKIQDKEGIPPDQQRLIFAGKQLEDG
Sbjct: 68711 VLRHANNLAV-VKTLTGKTITLEVESSDTIDNVKTKIQDKEGIPPDQQRLIFAGKQLEDG 68535

Query:   130 RTLSDYNIQKESTLHLVLRLRGGMQIFVKTLTGKTITLEVESSDTIDNVKTKIQDKEGIP 189
             RTLSDYNIQKESTLHLVLRLRGGMQIFVKTLTGKTITLEVESSDTIDNVK+KIQDKEGIP
Sbjct: 68534 RTLSDYNIQKESTLHLVLRLRGGMQIFVKTLTGKTITLEVESSDTIDNVKSKIQDKEGIP 68355

Query:   190 PDQQRLIFAGKQLEDGRTLSDYNIQKESTLHLVLRLRGGMQIFVKTLTGKTITLEVESSD 249
             PDQQRLIFAGKQLEDGRTLSDYNIQKESTLHLVLRLRGGMQIFVKTLTGKTITLEVESSD
Sbjct: 68354 PDQQRLIFAGKQLEDGRTLSDYNIQKESTLHLVLRLRGGMQIFVKTLTGKTITLEVESSD 68175

Query:   250 TIDNVKTKIQDKEGIPPDQQRLIFAGKQLEDGRTLSDYNIQKESTLHLVLRLRGGN 305
             TIDNVKTKIQDKEGIPPDQQRLIFAGKQLEDGRTLSDYNIQKESTLHLVLRLRGGN
Sbjct: 68174 TIDNVKTKIQDKEGIPPDQQRLIFAGKQLEDGRTLSDYNIQKESTLHLVLRLRGGN 68007
```

FIG. 17

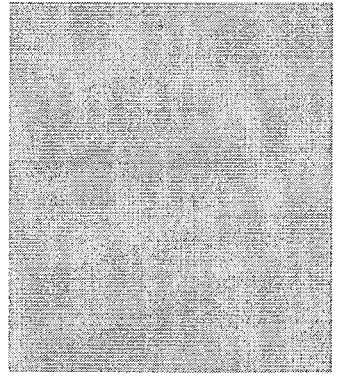

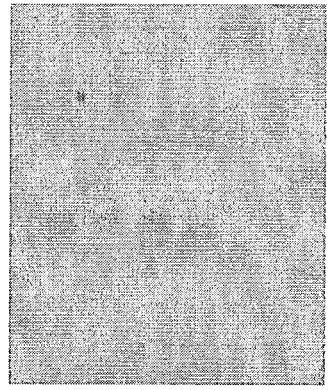

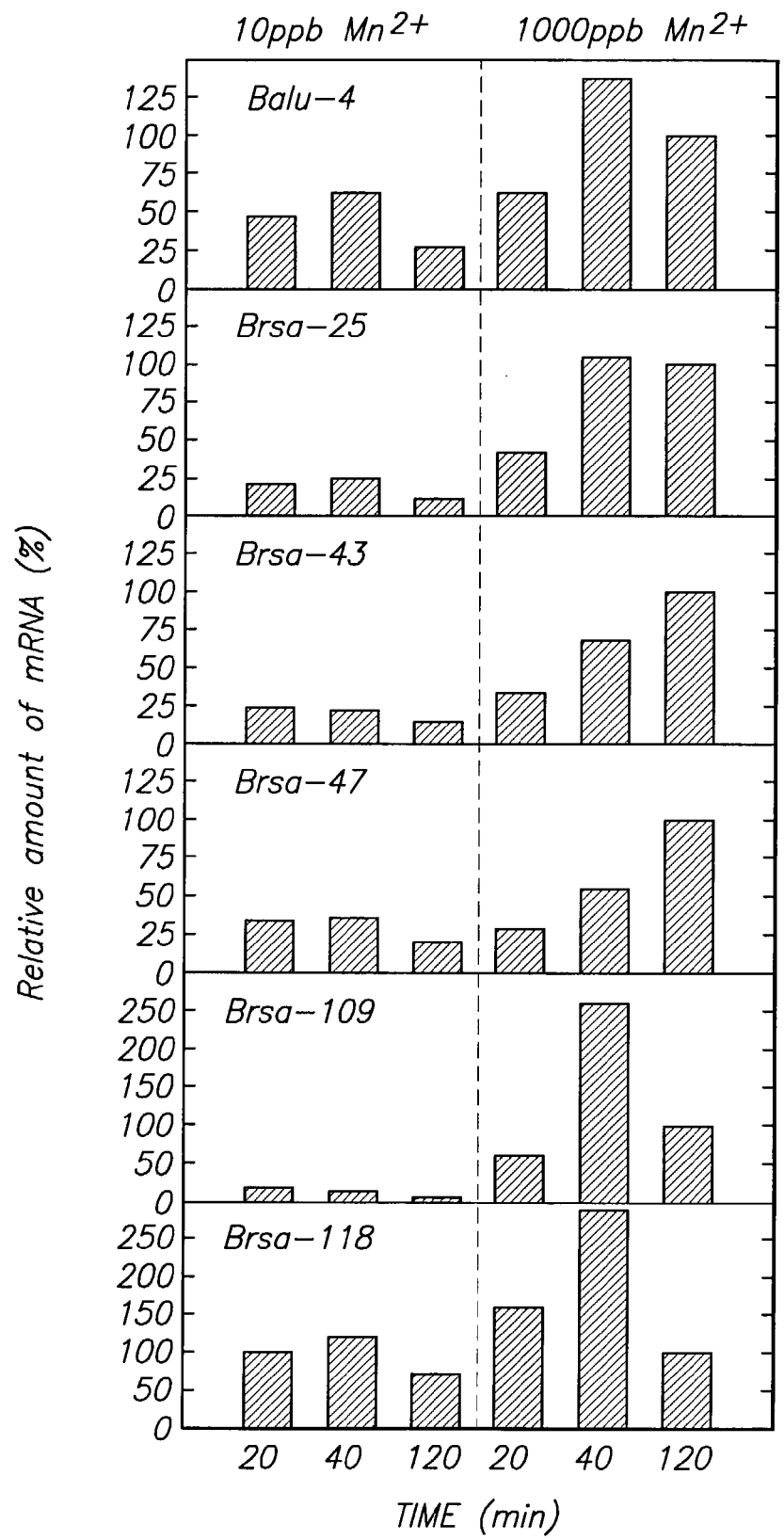

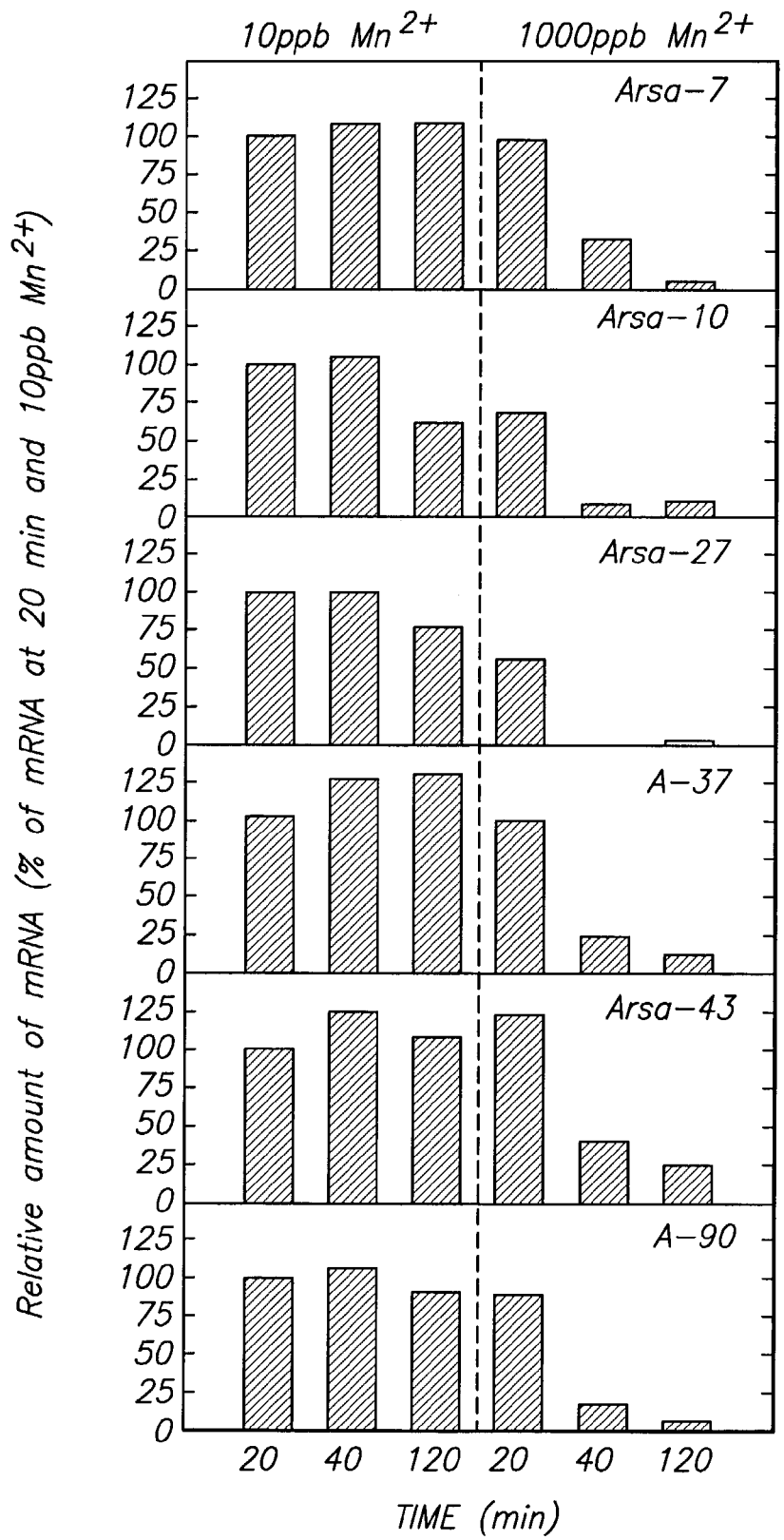

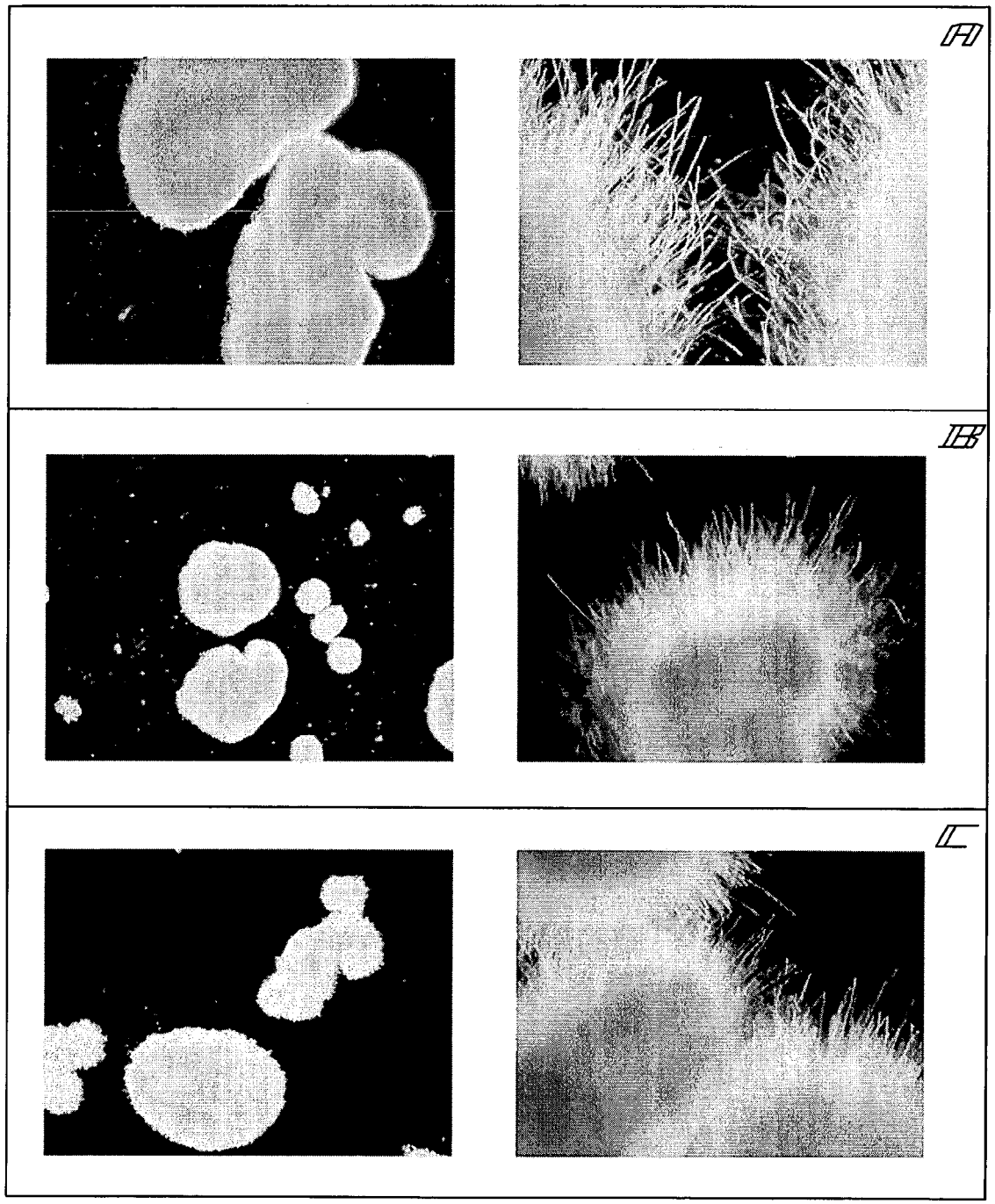

US 7,439,067 B2

ISOLATED POLYNUCLEOTIDES AND METHODS OF PROMOTING A MORPHOLOGY IN A FUNGUS

RELATED PATENT DATA

This patent claims benefit of priority under 35 U.S.C. §119 to U.S. Provisional Patent Ser. No. 60/382,132, which was filed May 20, 2002.

CONTRACTUAL ORIGIN OF THE INVENTION

This invention was made with Government support under contract DE-AC0676RLO-1830, awarded by the U.S. Department of Energy. The Government has certain rights in this invention.

TECHNICAL FIELD

The invention pertains to isolated polynucleotide molecules, recombinant polynucleotide constructs, and methods of promoting a morphology in a fungus.

BACKGROUND OF THE INVENTION

Fungi are becoming increasingly utilized for production of numerous commercially useful products. A type of fungi known as "filamentous" fungi are currently used for the industrial scale production of metabolites such as antibiotics (penicillins and cephalosporins, for example) and organic acids (citric and fumaric acids for example). Filamentous fungi are additionally useful for the industrial production of enzymes such as, for example, proteases and lipases.

Utilization of a filamentous fungus species for production of desired compounds often involves growing submerged cultures of the fungus. Filamentous fungi can exhibit numerous morphologies in submerged cultures, one of which is the filamentous morphology. When fungi in culture exhibit a filamentous morphology, the filamentous growth can increase the viscosity of the culture medium. The increased viscosity can affect the mass transfer and aeration properties of the culture, can cause mixing problems in a bioreactor, and can typically be accompanied by decreased productivity.

Alternatively, "filamentous" fungi can exhibit a pellet morphology. In contrast to cultures of fungi exhibiting a filamentous morphology, the viscosity of cultures of fungi exhibiting a pellet morphology can be relatively low and can utilize less power for mixing and aeration of the culture. For many products, for example citric acid, itaconic acid, statins, penicillins, and various enzymes, productivity can be enhanced utilizing fungus exhibiting a pellet morphology relative to fungus exhibiting a filamentous morphology. However, at least in certain fungal species, production of peptic enzyme or fumaric acid, for example, can be enhanced by utilizing a fungus exhibiting a filamentous morphology.

It would be desirable to develop methods to promote a desired morphology in a fungus and to develop methods for influencing or controlling morphologies exhibited by a fungus in a culture to optimize productivity.

SUMMARY OF THE INVENTION

In one aspect, the invention encompasses an isolated polynucleotide molecule that is differentially expressed in a native fungus exhibiting a pellet morphology relative to the native fungus exhibiting a filamentous morphology.

In one aspect, the invention encompasses a method of enhancing a bioprocess utilizing a fungus. A transformed fungus is produced by transforming a fungus with a recombinant polynucleotide molecule. The recombinant polynucleotide molecule contains an isolated polynucleotide sequence linked operably to a promoter. A polypeptide encoded by the polynucleotide sequence is expressed to promote a pellet morphology. The pellet morphology of the transformed fungus enhances a bioprocess relative to the bioprocess utilizing a filamentous morphology of the transformed fungus.

In one aspect, the invention encompasses a method of promoting a morphology of a fungus and enhancing productivity of a bioprocess. A fungus is transformed with an antisense oriented polynucleotide sequence complimentary to a gene sequence. A transcription product of the polynucleotide sequence hybridizes to an mRNA and thereby suppresses expression of the gene. The gene suppression promotes a morphology and enhances a bioprocess relative to the bioprocess in an alternative fungal morphology.

BRIEF DESCRIPTION OF THE DRAWINGS

Preferred embodiments of the invention are described below with reference to the following accompanying drawings.

FIG. 1 shows the results of Northern blot analysis of the transcriptional level of the native *A. niger* gene corresponding to the Balu-4 cDNA sequence set forth in SEQ ID NO.:1. Lanes 1, 2 and 3 reflect transcription levels in the pellet morphology. Transcription levels in the filamentous morphology are shown at 20 minutes (lane 4), 40 minutes (lane 5) and 120 minutes (lane 6) after inducing the filamentous morphology.

FIG. 2 shows the alignment and comparison of the predicted amino acid sequence of *A. niger* Balu-4, SEQ ID NO.:2 (top sequence) and the amino acid sequence of *Emericella nidulans* G-protein beta subunit, SEQ ID NO.:3 (bottom sequence).

FIG. 6 shows the alignment and comparison of the predicted amino acid sequence of *A. niger* Brsa-43, SEQ ID NO.:10 (top sequence), and the amino acid sequence of the *Homo sapiens* lysosomal pepstatin insensitive protease, SEQ ID NO.:11 (bottom sequence).

FIG. 7 shows the results of Northern blot analysis of transcription levels of the native *A. niger* gene corresponding to the Brsa-47 cDNA sequence set forth in SEQ ID NO.:12. Lanes 1, 2 and 3 reflect transcription levels in the pellet morphology. Transcription levels in the filamentous morphology are shown at 20 minutes (lane 4), 40 minutes (lane 5) and 120 minutes (lane 6) after inducing the filamentous morphology.

FIG. 8 shows the alignment and comparison of the predicted amino acid sequence of *A. niger* Brsa-47, SEQ ID NO.:14 (top sequence), and the amino acid sequence of *Sesamum indicum* Myo-inositol 1-phosphate synthase, SEQ ID NO.:15 (bottom sequence).

FIG. 9 shows the results of Northern blot analysis of transcription levels of the native *A. niger* gene corresponding to the Brsa-109 cDNA sequence set forth in SEQ ID NO.:16. Lanes 1, 2 and 3 reflect transcription levels in the pellet morphology. Transcription levels in the filamentous morphology are shown at 20 minutes (lane 4), 40 minutes (lane 5) and 120 minutes (lane 6) after inducing the filamentous morphology.

FIG. 10 shows the results of Northern blot analysis of transcription levels of the native *A. niger* gene corresponding to the Brsa-118 cDNA sequence set forth in SEQ ID NO.:18. Lanes 1, 2 and 3 reflect transcription levels in the pellet morphology. Transcription levels in the filamentous morphology are shown at 20 minutes (lane 4), 40 minutes (lane 5) and 120 minutes (lane 6) after inducing the filamentous morphology.

FIG. 11 shows the alignment and comparison of the predicted amino acid sequence of *A. niger* Brsa-118, SEQ ID NO.:20 (top sequence), and the *Neurospora crassa* probable hydroxymethylglutaryl-CoA synthase, SEQ ID NO.:21 (bottom sequence).

FIG. 17 shows the alignment and comparison of the predicted amino acid sequence of *A. niger* Arsa-43, SEQ ID NO.:34 (top sequence), and the *Aspergillus nidulans* polyubiquitin protein, SEQ ID NO.:35 (bottom sequence).

FIG. 18 shows the results of Northern blot analysis of transcription levels of the native *A. niger* gene corresponding to the Arsa-10 cDNA partial sequence set forth in SEQ ID NO.:36. Lanes 1, 2 and 3 reflect transcription levels in the pellet morphology. Transcription levels in the filamentous morphology are shown at 20 minutes (lane 4), 40 minutes (lane 5) and 120 minutes (lane 6) after inducing the filamentous morphology.

FIG. 19 shows the results of Northern blot analysis of transcription levels of the native *A. niger* gene corresponding to the Arsa-27 cDNA partial sequence set forth in SEQ ID NO.:37. Lanes 1, 2 and 3 reflect transcription levels in the pellet morphology. Transcription levels in the filamentous morphology are shown at 20 minutes (lane 4), 40 minutes (lane 5) and 120 minutes (lane 6) after inducing the filamentous morphology.

FIG. 20 shows a comparison of enhanced expression levels in filamentous morphology (right) relative to the pellet morphology (left) of native *A. niger* for each of the Balu-4, Brsa-25, Brsa-43, Brsa-47, Brsa-109, and Brsa-118 genes.

FIG. 26 shows suppression results for *A. niger* transformed with antisense oriented polynucleotide sequences complimentary to cDNAs corresponding to Arsa-7 (Panel A), A-37 (Panel B) and A-90 (Panel C). Each panel compares morphologies of control *A. niger* (left) and transformed *A. niger* (right) grown in 12 ppb $Mn^{2+}$ medium.

FIG. 27 shows the citric acid production of control *A. niger* and transformed *A. niger* containing antisense polynucleotide sequence complimentary to Balu-42 (strain 2805) or complimentary to Brsa-118 (strain 2808). Panel (A) shows measured citric acid production for individual transformation experiments. Panel (B) shows averaged values of the data depicted in Panel (A).

DETAILED DESCRIPTION OF THE PREFERRED EMBODIMENTS

Figure 3:
FIG. 3 shows the results of Northern blot analysis of transcription levels of the native *A. niger* gene corresponding to the Balu-42 cDNA sequence set forth in SEQ ID NO.:4. Lanes 1, 2 and 3 reflect transcription levels in the pellet morphology. Transcription levels in the filamentous morphology are shown at 20 minutes (lane 4), 40 minutes (lane 5) and 120 minutes (lane 6) after inducing the filamentous morphology.

The invention encompasses polynucleotides that can have differential expression in a native fungus. For purposes of the present description the term "expression" of a polynucleotide sequence can refer to the combined processes of transcription and translation, or can refer to a portion of the combined transcription and translation process. The term "differential expression" can refer to two or more differing levels of expression, or can refer to an absence in expression in a first instance relative to a presence of expression in a second instance.

The invention includes isolated polynucleotide molecules that can include a polynucleotide sequence that is differentially expressed in different morphologies exhibited by a native fungus. For purposes of the present description, the term "native" can refer to an organism that has not been genetically manipulated. The term "isolated" can refer to a naturally occurring molecule such as, for example, a polynucleotide or a polypeptide that has been recovered from the organism which produced it, or alternatively can refer to a synthetic molecule.

An isolated polynucleotide molecule according to the present invention can comprise a polynucleotide sequence that has an increased expression in a fungus exhibiting a pellet morphology relative to a lower level or an absence of expression in the filamentous morphology of the fungus. Alternatively, a polynucleotide molecule according to the present invention can comprise polynucleotide sequence having an increased expression level in a filamentous morphology of a native fungus relative to a lower level or absence of expression in the pellet morphology.

Isolated polynucleotides encompassed by the present invention can be isolated from any source fungus that is capable of exhibiting a filamentous morphology and a pellet morphology. A source fungus is not limited to a specific group of fungi and can be a member any of the three major fungi groups. An exemplary member of the Basidiomycetes group is *Phanerochaete chrysosporium*. Exemplary members of the group of Ascomycetes and Imperfect Fungus include *Aspergillus niger, Aspergillus oryzae, Aspergillus terreus, Emericella nidulans, Neurospora crassa, Fusarium oxysporum, Penicillium chrysogenum*, and *Trichoderma reesei*. Exemplary members of the Zygomycetes group include *Rhizomucor miehei* and *Rhizopus oryzae*.

An exemplary isolated polynucleotide molecule encompassed by the present invention can comprise a polynucleotide sequence isolated from *A. niger* that is differentially expressed in the filamentous morphology of native-*A. niger* relative to the pellet morphology of native *A. niger*. The differentially expressed polynucleotide sequence can comprise, for example, a sequence as set forth in any of SEQ ID NOs.:1, 4, 6, 8, 12, 16, 18, 22, 24, 26, 28, 33, 36 and 37, or can comprise a sequence complimentary to any of those sequences. Each of the polynucleotide sequences set forth in SEQ ID NOs.:1, 4, 6, 8, 12, 16, 18, 22, 24, 26, 28, 33, 36 and 37, corresponds to the sequence determined from a full-length cDNA molecule prepared according to methods discussed below, with SEQ ID NOs.:36 and 37 being partial sequences determined from full length cDNA. It is to be understood that the isolation methods and techniques discussed herein are exemplary and that numerous conventional techniques can be utilized for producing the isolated polynucleotide molecules of the present invention.

Full-length cDNA molecules comprising the polynucleotide sequences set forth in SEQ ID NOs.:1, 4, 6, 8, 12, 16, 18, 22, 24, 26, 28, 33, 36 and 37, are obtained from *A. niger* strain ATCC11414 utilizing suppression subtractive hybridization techniques (Diatchenko et al., *Proceedings National Academy of Science U.S.A.* Vol. 93, pp. 6025-6030, 1996), in conjunction with PCR-SELECT™ cDNA subtraction kit (CLONTECH, Palo Alto, Calif.). Two suppression subtractive cDNA libraries are constructed. A first cDNA library is constructed utilizing cDNA obtained from *A. niger* exhibiting the pellet type morphology as tester and cDNA obtained from *A. niger* exhibiting the filamentous morphology as a driver. The driver/tester ratio is increased threefold over the ratio suggested by the subtraction kit manual.

A second suppression subtractive cDNA library is created utilizing cDNA obtained from *A. niger* exhibiting the filamentous morphology as tester and utilizing cDNA obtained from *A. niger* exhibiting pellet morphology as driver. A first cDNA pool is generated from the first library and a second cDNA pool is generated from the second library. Differentially expressed cDNAs that are specifically present or enhanced in the pellet morphology are isolated from the first cDNA library by hybridization utilizing the first cDNA pool as probes and independently hybridizing utilizing the second cDNA pool as probes. Isolation of cDNA that is enhanced or specific to the filamentous morphology of *A. niger* is achieved by independently hybridizing the second cDNA library utilizing the first cDNA pool and the second cDNA pool as probes.

The segments of differentially expressed cDNAs that are isolated by suppression subtractive hybridization are selected for DNA sequencing. Sequencing of the segments is performed utilizing single pass sequencing with the T7-2 primer. The DNA fragments isolated by the suppression subtractive hybridization are used to design pairs of gene specific primers for utilization in isolating full-length cDNAs.

Full-length cDNA isolation is achieved utilizing the marathon cDNA amplification kit and the ADVANTAGE® cDNA polymerase (CLONTECH, Palo Alto, Calif.). The gene specific primers designed from the suppression subtractive hybridization clones are utilized for performing rapid amplification of cDNA ends PCR (RACE-PCR). The sequence of full-length cDNAs is determined using conventional automated DNA sequencing methods.

Twelve full-length cDNA clones and two partial-length cDNA clones are produced and sequenced according to the methods discussed above. The resulting sequences are presented as follows. The sequence of the Balu-4 cDNA is set forth in SEQ ID NO.:1; the sequence of the Balu-42 cDNA is set forth in SEQ ID NO.:4; the sequence of the Brsa-25 cDNA is set forth in SEQ ID NO.:6; the sequence of the Brsa-43 cDNA is set forth in SEQ ID NO.:8; the sequence of the Brsa-47 cDNA is set forth in SEQ ID NO.:12; the sequence of the Brsa-109 cDNA is set forth in SEQ ID NO.:16; the sequence of the Brsa-118 cDNA is set forth in SEQ ID NO.:

18; the sequence of the Arsa-7 cDNA is set forth in SEQ ID NO.:22; the sequence of the Arsa-48 cDNA is set forth in SEQ ID NO.:24; the sequence of the A-37 cDNA is set forth in SEQ ID NO.:26; the sequence of the A-90 cDNA is set forth in SEQ ID NO.:28; the sequence of the Arsa-43 cDNA is set forth in SEQ ID NO.:33; the partial sequence of the Arsa-10 cDNA is set forth in SEQ ID NO.:36; and the partial sequence of the Arsa-27 cDNA is set forth in SEQ ID NO.:37.

The amino acid sequence of each of the fourteen determined polynucleotide sequences is predicted utilizing the known genetic code. Homology searches are performed utilizing BLASTP to investigate homology between a predicted amino acid sequence and the sequences in the NCBI non-redundant GenBank CDS. All homology searches are conducted utilizing a threshold E value of E=0.005. Accordingly, the results of each BLAST homology search (discussed below) are based upon this initial threshold value.

Northern blot analysis is utilized to analyze the expression levels of the genes in native *A. niger* corresponding to each of the fourteen cDNA clones. The expression of each gene by *A. niger* exhibiting filamentous morphology is compared to the expression of the same gene in *A. niger* exhibiting the pellet morphology. For expression analysis, *A. niger* is initially grown in a culture medium containing less than or equal to about 12 parts per billion (ppb) $Mn^{2+}$ for 12 hours. After the initial 12 hours of growth the culture is divided into two halves, the first half is maintained at low $Mn^{2+}$ concentration (less than or equal to about 12 ppb) and the other half is brought to a final concentration of approximately 1000 ppb $Mn^{2+}$ (or in some instances to a final concentration of greater than or equal to about 15 ppb $Mn^{2+}$). *A. niger* can be extremely sensitive to $Mn^{2+}$ concentration. At $Mn^{2+}$ concentrations at or below about 12 ppb, native *A. niger* exhibits the pelleted morphology, while at $Mn^{2+}$ concentrations higher than about 12 ppb, native *A. niger* exhibits filamentous morphology. To simplify the present description, the point at which the culture is divided into two halves (after 12 hours of initial growth) can be referred to as time zero (t=0). Additionally, since the addition of $Mn^{2+}$ to a final concentration of above 12 ppb promotes the filamentous morphology, the addition of $Mn^{2+}$ can be referred to as filament induction.

Culture samples are collected at 20, 40, 60 and 120 minutes after time zero from both the non-induced culture (pellet morphology) and the induced culture (filamentous morphology). The samples are centrifuged to form culture pellets which are frozen with liquid nitrogen and stored at –80° C. for future total RNA extraction.

Total RNA can be isolated from the frozen culture pellets utilizing conventional methods. After size fractionation of the total RNA sample by conventional gel electrophoresis techniques and subsequent transfer to a blotting membrane, the total RNA samples collected at each time point are analyzed using hybridization of probes that are synthesized by randomly priming the isolated suppression subtractive hybridization cDNA fragments or by randomly priming fragments of full-length cDNA digested with restricting endonuclease. Probe synthesis includes incorporation of [$^{32}$P]-α-dCTP. Hybridization results of the Northern blots can be visualized by exposing the blots to x-ray film.

FIG. 1 shows the x-ray film exposure of a Northern blot analysis of the expression of the *A. niger* gene corresponding to Balu-4 SEQ ID NO.:1. Increased hybridization is apparent in mRNA samples taken from filamentous cultures (lanes 4, 5 and 6) relative to mRNA produced in pellet morphology (lanes 1-3). Fifteen micrograms (μg) of total RNA is used for each lane. The RNA samples utilized are obtained from post t=0 pellet cultures at t=20 minutes (lane 1), t=40 minutes (lane 2) and t=120 minutes (lane 3); and from post-induction filamentous cultures at t=20 minutes (lane 4), t=40 minutes (lane 5) and t=120 minutes (lane 6). The total RNA used for each lane and the lane identification for each of the Northern blots discussed below is the same as that set forth for FIG. 1. The results shown in FIG. 1 indicate that Balu-4 is differentially expressed in native *A. niger*, with an increased level of expression detected in the filamentous morphology.

The predicted amino acid sequence of Balu-4 is set forth in SEQ ID NO.:2. The Balu-4 amino acid sequence is predicted from the Balu-4 cDNA sequence (SEQ ID NO.:1). As shown in FIG. 2, an amino acid sequence homology search utilizing BLASTP indicates that SEQ ID NO.:2 (top sequence) has a 97% identity with the amino acid sequence of a G-protein beta subunit of *Emericella nidulans*, SEQ ID NO.:3 (bottom sequence). Positions of sequence identity are indicated by the placement of the corresponding identical amino acid symbol between SEQ ID NO.:2 (top) and SEQ ID NO.:3 (bottom). The symbol "+" shown intermediate SEQ ID NO.:2 and SEQ ID NO.:3 indicates a conservative amino acid difference. For purposes of the present invention a conservative amino acid difference or a conservative amino acid substitution can refer to a substitution of one amino acid by another amino acid with similar chemical properties. Additionally, the term "homology" can, in some instances, refer to an identical or a conservative amino acid.

The appearance of an open space between corresponding positions in SEQ ID NO.:2 and SEQ ID NO.:3 in FIG. 2 indicates a non-conservative amino acid difference between the two aligned sequences. Three sections of SEQ ID NO.:2 having relatively minimal identity with SEQ ID NO.:3 are set forth as SEQ ID NOs.:30, 31 and 32. SEQ ID NO.:30 corresponds to amino acids 28-49 of SEQ ID NO.:2. SEQ ID NO.:31 corresponds to amino acids 194-209 of SEQ ID NO.:2. SEQ ID NO.:32 corresponds to amino acids 260-288 of SEQ ID NO.:2.

FIG. 3 shows the results of Northern blot analysis of the expression of the native gene corresponding to Balu-42, SEQ ID NO.:4. The increased detection of mRNA corresponding to Balu-42 in the filamentous morphology indicates that Balu42 is differentially expressed with increased expression in filaments relative to the pellet morphology of native *A. niger*.

SEQ ID NO.:5 corresponds to the Balu-42 amino acid sequence predicted from SEQ ID NO.:4. A BLASTP homology search is unable to identify homology between SEQ ID NO.:5 and any sequence in the searched database.

Figure 4:
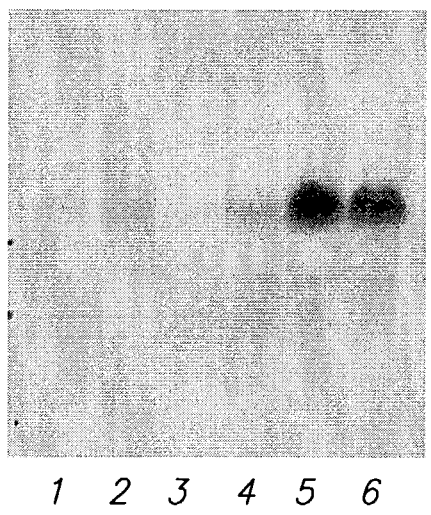
FIG. 4 shows the results of Northern blot analysis of transcription levels of the native *A. niger* gene corresponding to the Brsa-25 cDNA sequence set forth in SEQ ID NO.:6. Lanes 1, 2 and 3 reflect transcription levels in the pellet morphology. Transcription levels in the filamentous morphology are shown at 20 minutes (lane 4), 40 minutes (lane 5) and 120 minutes (lane 6) after inducing the filamentous morphology.

FIG. 4 shows the results of Northern blot analysis of the expression of the native gene corresponding to the Brsa-25 cDNA sequence set forth in SEQ ID NO.:6. The results indicate that Brsa-25 is differentially expressed with increased expression in the filamentous morphology of native *A. niger* relative to the pellet morphology.

The predicted amino acid sequence of Brsa-25 SEQ ID NO.:6 is set forth in SEQ ID NO.:7. A BLASTP homology search was unable to identify homology between SEQ ID NO.:7 and any sequence in the searched database.

Figure 5:
FIG. 5 shows the results of Northern blot analysis of transcription levels of the native *A. niger* gene corresponding to the Brsa-43 cDNA sequence set forth in SEQ ID NO.:8. Lanes 1, 2 and 3 reflect transcription levels in the pellet morphology. Transcription levels in the filamentous morphology are shown at 20 minutes (lane 4), 40 minutes (lane 5) and 120 minutes (lane 6) after inducing the filamentous morphology.

FIG. 5 shows results of the Northern blot analysis of the expression of the native gene corresponding to the Brsa-43 cDNA set forth in SEQ ID NO.:8. The Northern blot results indicate that Brsa-43 is differentially expressed with increased expression in the filamentous morphology of native *A. niger* relative to the pellet morphology.

The Brsa-43 amino acid sequence predicted from SEQ ID NO.: 8 is set forth in SEQ ID NO.: 9. SEQ ID NO.:10 corresponds to amino acids 29-594 of SEQ ID NO.:9. FIG. 6 shows the BLASTP alignment and comparison of Brsa-43 SEQ ID NO.:10 (top sequence) which has 31% identity to the amino acid sequence of human tripeptidyl-peptidase I precursor (lysosomal pepstatin insensitive protease), SEQ ID NO.:11 (bottom sequence). Indication of identity and homology between sequences is as discussed above with respect to FIG. 2.

FIG. 7 shows the results of Northern blot analysis of the expression of the native Brsa-47 gene corresponding to the cDNA sequence set forth in SEQ ID NO.:12. The results indicate that Brsa-47 is differentially expressed; with increased expression levels apparent in the filamentous morphology relative to the pellet morphology of native A. niger.

The amino acid sequence of Brsa-47 as predicted from SEQ ID NO.:12 is set forth in SEQ ID NO.:13. FIG. 8 shows the BLASTP homology search results for SEQ ID NO.:14 (top sequence) which corresponds to amino acids 26-530 of SEQ ID NO.:13. The BLASTP results indicate that SEQ ID NO.:14 has a 56% identity with the amino acid sequence of Myo-inositol 1-phosphate synthase from *Sesamum indicum*, SEQ ID NO.:15 (bottom sequence).

The results of Northern blot analysis of the expression of the Brsa-109 gene in native *A. niger* corresponding to the cDNA sequence set forth in SEQ ID NO.:16 is shown in FIG. 9. The results indicate that the Brsa-109 gene is differentially expressed, with increased expression detected in the filamentous morphology relative to the pellet morphology.

The Brsa-109 amino acid sequence predicted from SEQ ID NO.: 16, is set forth in SEQ ID NO.:17. A BLASTP homology search is unable to identify homology between SEQ ID NO.: 19 and any sequence in the database.

FIG. 10 shows the results of Northern blot analysis of the expression of the Brsa-118 gene in native *A. niger* corresponding to the cDNA sequence set forth in SEQ ID NO.:18. The results indicate that the Brsa-118 gene is differentially expressed, with increased expression in the filamentous morphology relative to the pellet morphology.

The amino acid sequence of Brsa-118 predicted from SEQ ID NO.:18 is set forth in SEQ ID NO.:19. FIG. 11 shows the BLASTP homology search results for Brsa-118. The results show that the predicted amino acid sequence of Brsa-118, SEQ ID NO.:20 (top sequence), has 66% identity with the amino acid sequence of probable hydroxymethylglutaryl-CoA synthase from *Neurospora crassa*, SEQ ID NO.:21 (bottom sequence).

Figure 12:
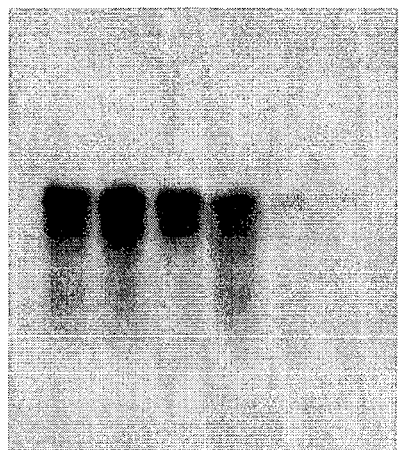
FIG. 12 shows the results of Northern blot analysis of transcription levels of the native *A. niger* gene corresponding to the Arsa-7 cDNA sequence set forth in SEQ ID NO.:22. Lanes 1, 2 and 3 reflect transcription levels in the pellet morphology. Transcription levels in the filamentous morphology are shown at 20 minutes (lane 4), 40 minutes (lane 5) and 120 minutes (lane 6) after inducing the filamentous morphology.

FIG. 12 shows the results of Northern blot analysis of the expression of the Arsa-7 gene in native *A. niger* corresponding to the cDNA sequence set forth in SEQ ID NO.:22. The results indicate that the Arsa-7 gene is differentially expressed, with increased expression levels in the pellet morphology relative to expression levels in the filamentous morphology.

The amino acid sequence of Arsa-7 as predicted from SEQ ID NO.: 22 is set forth in SEQ ID NO.:23. BLAST homology search results were unable to identify any sequences with homology to the predicted amino acid sequence of Arsa-7.

Figure 13:
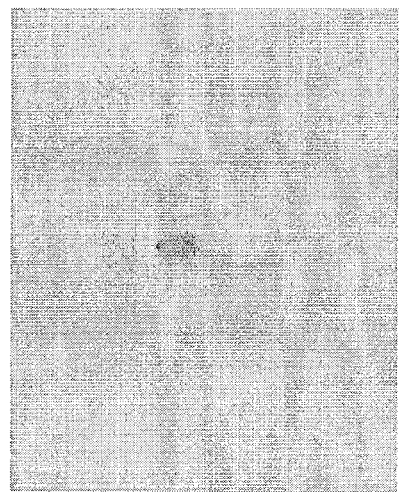
FIG. 13 shows the results of Northern blot analysis of transcription levels of the native *A. niger* gene corresponding to the Arsa-48 cDNA sequence set forth in SEQ ID NO.:24. Lanes 1, 2 and 3 reflect transcription levels in the pellet morphology. Transcription levels in the filamentous morphology are shown at 20 minutes (lane 4), 40 minutes (lane 5) and 120 minutes (lane 6) after inducing the filamentous morphology.

FIG. 13 shows the results of Northern blot analysis and the expression of the Arsa-48 gene in native *A. niger* corresponding to the cDNA sequence set forth in SEQ ID NO.:24. The results indicate the Arsa-48 gene is differentially expressed, with increased expression levels occurring in the pellet morphology relative to the filamentous morphology.

The Arsa-48 amino acid sequence as predicted from SEQ ID NO.:24, is set forth in SEQ ID NO.:25. A BLASTP homology search was unable to identify homology between the Arsa-48 amino acid sequence and any other amino acid sequence in the searched database.

Figure 14:
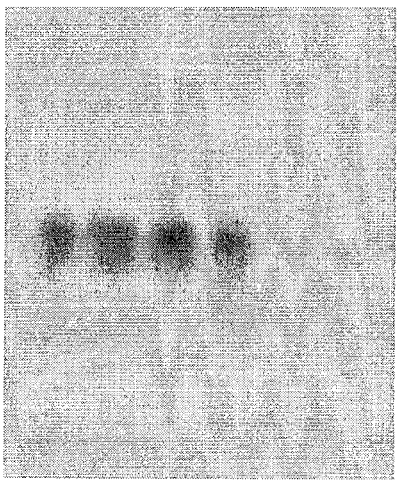
FIG. 14 shows the results of Northern blot analysis of transcription levels of the native *A. niger* gene corresponding to the A-37 cDNA sequence set forth in SEQ ID NO.:26. Lanes 1, 2 and 3 reflect transcription levels in the pellet morphology. Transcription levels in the filamentous morphology are shown at 20 minutes (lane 4), 40 minutes (lane 5) and 120 minutes (lane 6) after inducing the filamentous morphology.

FIG. 14 shows the results of a Northern blot analysis of the expression of the A-37 gene in native *A. niger* corresponding to the cDNA sequence set forth in SEQ ID NO.:26. The results indicate that the A-37 gene is differentially expressed with increased expression occurring in the pellet morphology relative to the expression level detected in the filamentous morphology.

The A-37 amino acid sequence as predicted from SEQ ID NO.:26, is set forth in SEQ ID NO.:27. The BLASTP homology search was unable to detect any homology between the predicted A-37 amino acid sequence and other amino acid sequences in the searched database.

Figure 15:
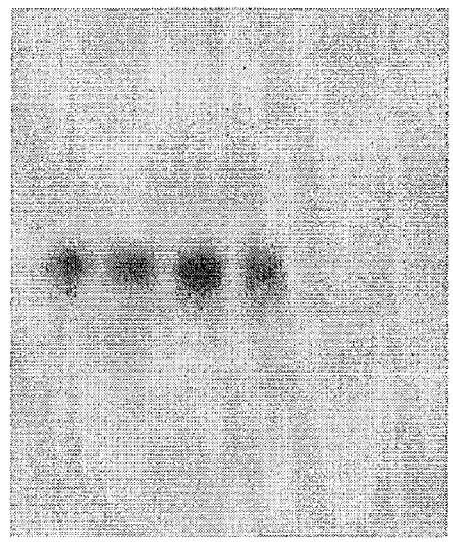
FIG. 15 shows the results of Northern blot analysis of transcription levels of the native *A. niger* gene corresponding to the A-90 cDNA sequence set forth in SEQ ID NO.:28. Lanes 1, 2 and 3 reflect transcription levels in the pellet morphology. Transcription levels in the filamentous morphology are shown at 20 minutes (lane 4), 40 minutes (lane 5) and 120 minutes (lane 6) after inducing the filamentous morphology.

FIG. 15 shows the result of Northern blot analysis of the expression of the A-90 gene in native *A. niger* corresponding to the cDNA sequence set forth in SEQ ID NO.:28. The results indicate that A-90 is differentially expressed with an increased expression level occurring in the pellet morphology relative to the expression level detected in the filamentous morphology.

The amino acid sequence of A-90 as predicted from SEQ ID NO.:28, is set forth in SEQ ID NO.:29. A BLASTP homology search performed on SEQ ID NO.:29, is unable to detect any homology with any other amino acid sequence in the database.

Figure 16:
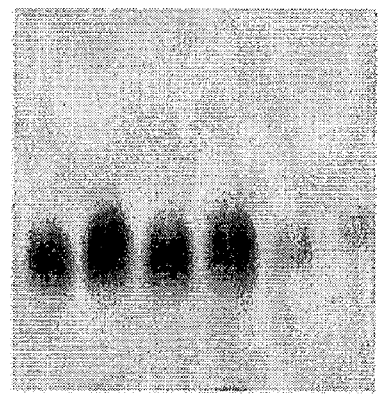
FIG. 16 shows the results of Northern blot analysis of transcription levels of the native *A. niger* gene corresponding to the Arsa-43 cDNA sequence set forth in SEQ ID NO.:33. Lanes 1, 2 and 3 reflect transcription levels in the pellet morphology. Transcription levels in the filamentous morphology are shown at 20 minutes (lane 4), 40 minutes (lane 5) and 120 minutes (lane 6) after inducing the filamentous morphology.

FIG. 16 shows the results of Northern blot analysis of the expression of the Arsa-43 gene in native *A. niger* corresponding to the cDNA sequence set forth in SEQ ID NO.:33. The results indicate that the Arsa-43 gene is differentially expressed, with increased expression in the pellet morphology relative to the filamentous morphology.

The amino acid sequence of Arsa-43 predicted from SEQ ID NO.:33, is set forth in SEQ ID NO.:34. FIG. 17 shows the BLASTP homology search results for Arsa-43. The results show that the predicted amino acid sequence of Arsa-43, SEQ ID NO.:34 (top sequence), has 96% identity with the amino acid sequence of the polyubiquitin protein from *Aspergillus nidulans*, SEQ ID NO.:35 (bottom sequence).

FIG. 18 shows the results of Northern blot analysis of the expression of the Arsa-10 gene in native *A. niger* corresponding to the cDNA partial sequence set forth in SEQ ID NO.:36. The results indicate that the Arsa-43 gene is differentially expressed, with increased expression in the pellet morphology relative to the filamentous morphology. Homology searching is unable to detect any homology between SEQ ID NO.:36 and other polynucleotide sequences in the searched database FIG. 19 shows the results of Northern blot analysis of the expression of the Arsa-27 gene in native *A. niger* corresponding to the cDNA sequence set forth in SEQ ID NO.:37. The results indicate that the Arsa-43 gene is differentially expressed, with increased expression in the pellet morphology relative to the filamentous morphology. Homology searching is unable to detect any homology between SEQ ID NO.:37 and other polynucleotide sequences in the searched database.

Figure 21:
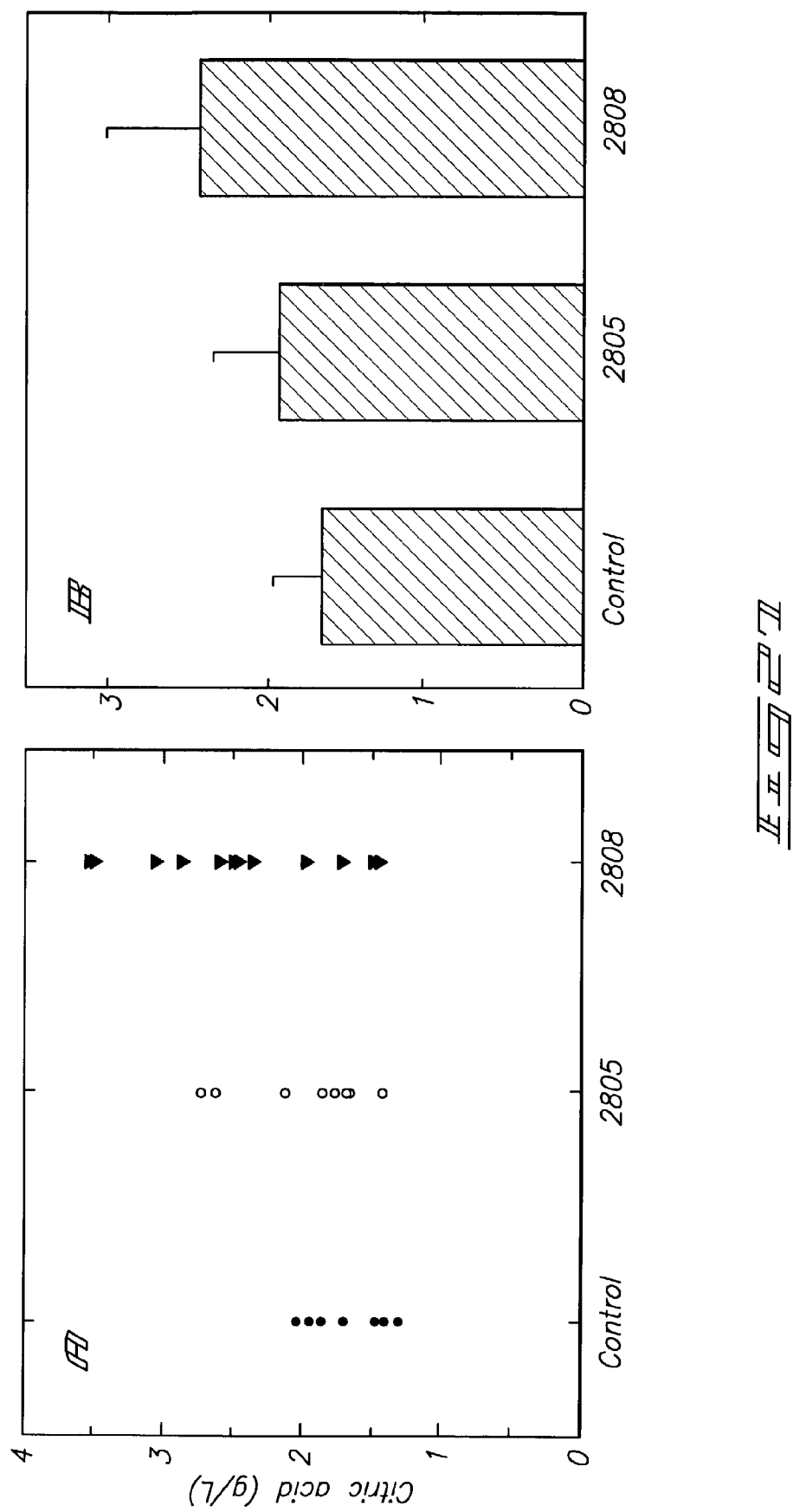
FIG. 21 shows a comparison of enhanced expression levels in the pellet morphology (left) relative to filamentous morphology (right) of native *A. niger* for each of the Arsa-7, Arsa-10, Arsa-27, A-27, Arsa-43 and A-90 genes.

Referring to FIGS. 20 and 21, such show bar-chart comparison of differential expression of various *A. niger* genes. FIG. 20 shows transcript levels for genes Balu-4. Brsa-25, Brsa-43, Brsa-47, Brsa-109 and Brsa-118, which show increased expression in filamentous *A. niger*. FIG. 21 shows transcript levels for genes Arsa-7, Arsa-10, Arsa-27, A-37, Arsa-43, and A-90, which show increased expression in the pellet morphology of *A. niger*.

Figure 22:
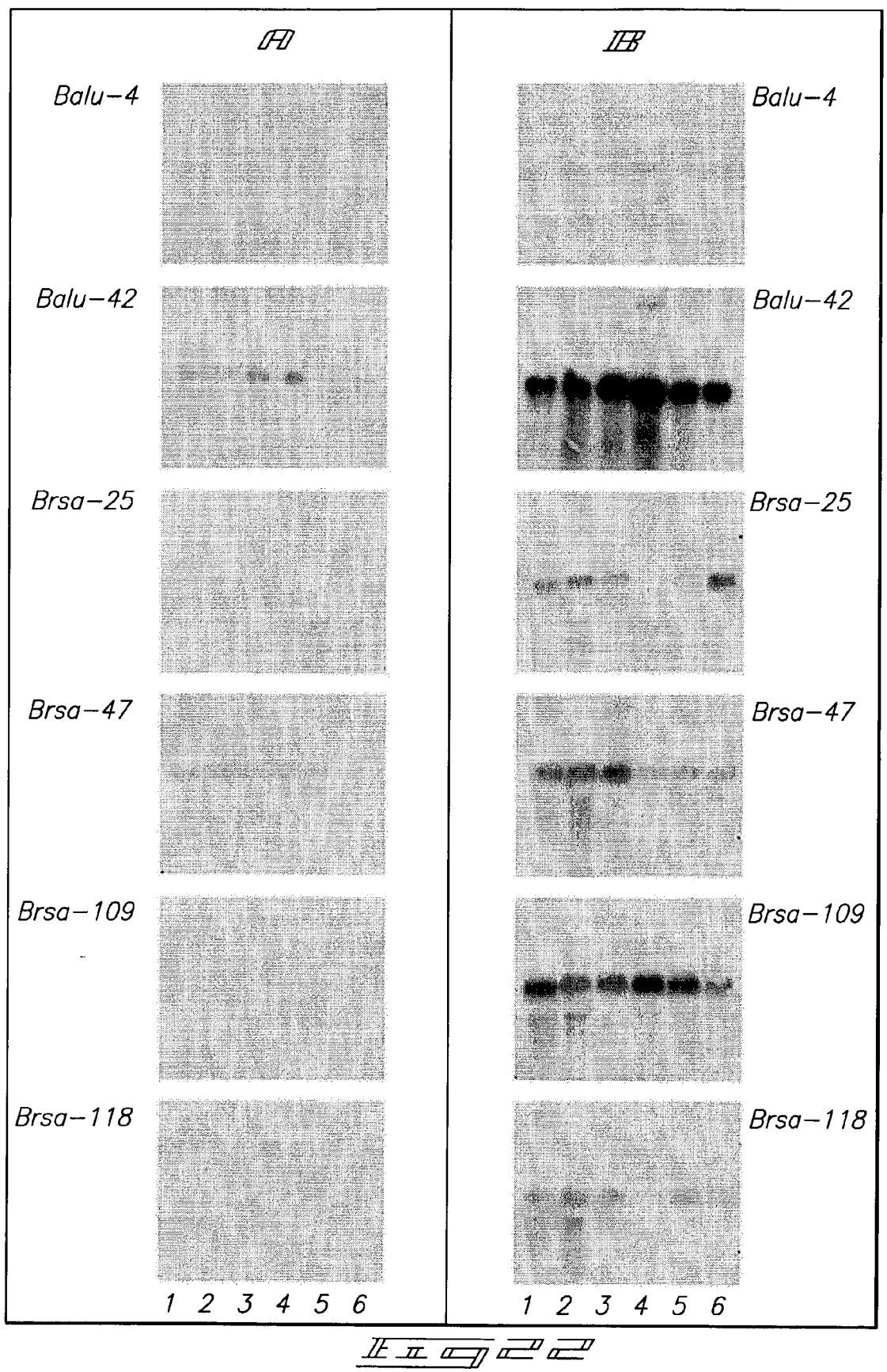
FIG. 22 shows the results of Northern blot analysis of transcription levels of the native *A. niger* genes corresponding to the Balu-4, Balu-42, Brsa-25, Brsa-47, Brsa-109, and Brsa-118 cDNA sequences set forth in SEQ ID NOs.:1, 4, 6, 12, 16 and 18, respectively. Panel (A) shows transcription levels in native *A. niger* grown in 10 ppb $Mn^{2+}$ (pellet morphology) for 14 hr (lane 1), 24 hr (lane 2), 48 hr (lane 3), 72 hr (lane 4), 96 hr (lane 5) and 120 hr (lane 6). Panel (B) shows transcription levels in native *A. niger* grown in 1000 ppb $Mn^{2+}$ (filamentous morphology) for 1 hr (lane 1), 2 hr (lane 2), 24 hr (lane 3), 36 hr (lane 4), 72 hr (lane 5) and 108 hr (lane 6).
Figure 23:
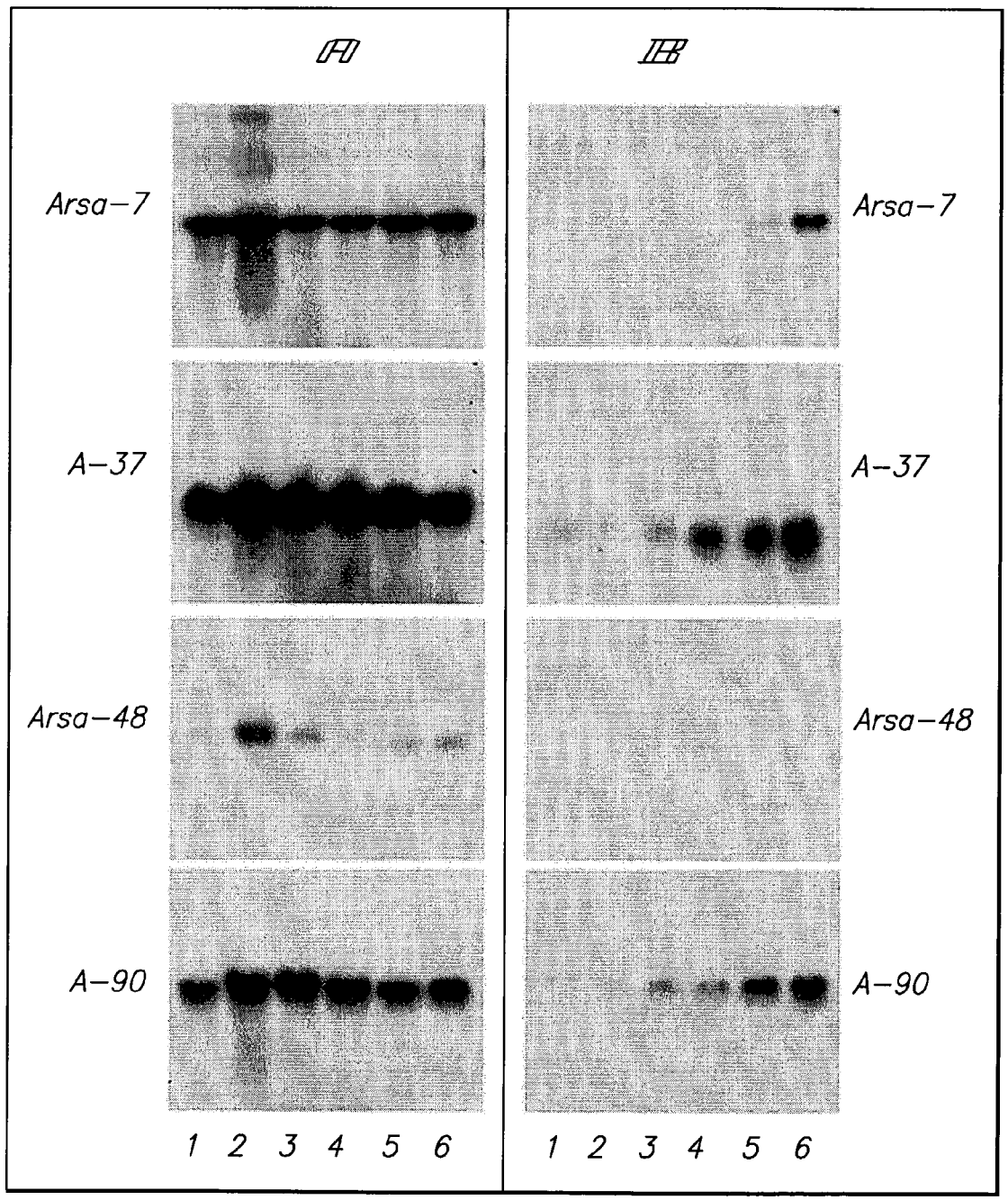
FIG. 23 shows the results of Northern blot analysis of transcription levels of the native *A. niger* genes corresponding to the Arsa-7, A-37, Arsa-48, and A-90 cDNA sequences set forth in SEQ ID NOs.:22, 24, 26 and 28, respectively. Panel (A) shows transcription levels in native *A. niger* grown in 10 ppb $Mn^{2+}$ (pellet morphology) for 14 hr (lane 1), 24 hr (lane 2), 48 hr (lane 3), 72 hr (lane 4), 96 hr (lane 5) and 120 hr (lane 6). Panel (B) shows transcription levels in native *A. niger* grown in 1000 ppb $Mn^{2+}$ (filamentous morphology) for 1 hr (lane 1), 2 hr (lane 2), 24 hr (lane 3), 36 hr (lane 4), 72 hr (lane 5) and 108 hr (lane 6).

Additional expression analysis is conducted utilizing cultures grown for up to 5 days post t=0 (as defined above). Referring to FIG. 22, such shows the increased transcript levels for genes Balu-4, Balu-42, Brsa-25, Brsa-47, Brsa-109, and Brsa-118 in native *A. niger* grown in filamentous conditions (Panel B) as compared to transcript levels in *A. niger* grown in pellet conditions (Panel A). Referring to FIG. 23, such shows the increased transcript levels for genes Arsa-7, A-37, Arsa-48 and A-90 in native *A. niger* grown in pellet conditions (Panel A), as compared to levels of the corresponding transcript in filamentous cultures (Panel B).

In particular embodiments, the present invention encompasses isolated polypeptide molecules comprising an amino acid sequence set forth in any of SEQ ID NOs.:2, 5, 7, 9, 13, 17, 19, 23, 25, 27, 29 and 34, and functional equivalents thereof. For purposes of the present description, the term functional equivalent can refer to a truncated version or a conservatively substituted version of an amino acid sequence having substantially equivalent functional properties and/or biological activity relative to the non-truncated, non-substituted polypeptide. As will be understood by those skilled in the art, conventional methods can be utilized for truncating or introducing conservative amino acid substitutions into the amino acid sequences set forth in the sequence listing. Conventional methods are available that can be utilized for producing of the isolated polypeptides of the present invention.

In addition to the isolated polynucleotide molecules discussed above, the present invention encompasses polynucleotides comprising alternative polynucleotide sequences that encode the amino acid sequences set forth in SEQ ID NOs.:2, 5, 7, 9, 13, 17, 19, 23, 25, 27, 29 and 34, or that encode functional equivalents of those amino acid sequences. The invention also encompasses amino acid sequences encoded by SEQ ID NOs.:36 and 37, and functional equivalents, and alternate polynucleotide sequences encoding the amino acid sequences encoded by SEQ ID NOs.:36 and 37. As will be under stood by those skilled in the art, various modifications can be introduced into a polynucleotide sequence without affecting the resulting amino acid sequence due to the degenerative nature of the genetic code.

Various recombinant polynucleotide constructs are encompassed by the present invention. In particular embodiments, a recombinant polynucleotide construct according to the present invention can comprise any of the isolated polynucleotide sequences discussed above. All or part of any of the polynucleotide sequences discussed herein can be linked to a promoter, preferably operably linked to a promoter. Operable linkage of a polynucleotide to a promoter to form a recombinant polynucleotide construct can allow expression of the polynucleotide sequence to be controlled by the promoter. Alternatively, a sequence complimentary to at least a part of a sequence set forth in any one of SEQ ID NO.:1, 4, 6, 8, 12, 16, 18, 22, 24, 26, 28, 33, 36 and 37, can be utilized to form a recombinant polynucleotide, and can be incorporated in antisense orientation.

In particular aspects, the complementary sequence can comprise a portion of complementary sequence of sufficient length to enable suppression hybridization (discussed below). Although utilization of polynucleotide sequences of fewer than 30 nucleotides is contemplated, suppression hybridization can typically involve utilization of one or more polynucleotides having a length of greater than or equal to 30 nucleotides. Accordingly, the invention encompasses polynucleotide sequences comprising a fragment of any of the sequences set forth in any one of SEQ ID NO.:1, 4, 6, 8, 12, 16, 18, 22, 24, 26, 28, 33, 36 and 37, and complimentary fragments. Such fragments can preferably comprise a length of at least 30 nucleotides of the corresponding sequence, or complimentary sequence.

The invention also encompasses a vector comprising any of the isolated polynucleotide sequences discussed above. Vectors encompassed by the present invention are not limited to a particular type of vector and can be, for example, a plasmid, a cosmid or a viral vector. Vectors according to the present invention can be utilized for introducing into a host cell one or more of the isolated polynucleotide molecules discussed. The host cell is not limited to a particular cell type and can be, for example, a bacterium, a fungus, or a higher-eukaryotic cell. Additionally, vectors encompassed by the present invention can be cloning vectors, expression vectors and/or integration vectors.

The invention also encompasses a transformed host cell and cell cultures which have been transformed to comprise any of the isolated polynucleotide molecules discussed above. Conventional cell transformation techniques can be utilized for introduction of the isolated polynucleotide into a desired host cell.

The present invention encompasses methods for promoting a morphology in a fungus. A process for promoting a morphology in a fungus is described with reference to a flowchart in FIG. 24. At initial step 100, an isolated polynucleotide is provided. The isolated polynucleotide from step 100 can comprise any of the isolated polynucleotides discussed above.

The isolated polynucleotide from step 100 can be used to form a recombinant polynucleotide in step 110. As discussed above, formation of the recombinant polynucleotide can comprise operably linking a promoter and the isolated polynucleotide sequence. Additionally, formation of a recombinant nucleotide step 110 can comprise formation of a vector which can be utilized to transform a fungus in step 120. Numerous fungi are available for utilization in transformation step 120. Preferably the fungus to be transformed is capable of exhibiting a filamentous morphology and is additionally capable of exhibiting a pellet morphology. Exemplary fungi for purposes of step 120 can be, for example, any of the fungi discussed above with respect to source fungi.

After transformation step 120, a polypeptide encoded by the recombinant polynucleotide can be expressed from the transformed fungus in step 130. The expression in step 130 can promote a particular morphology of the fungus. The particular morphology promoted by the expression can be determined by the sequence of the isolated polynucleotide provided in step 100. For example, a filamentous morphology can be promoted by providing an isolated polynucleotide encoding a polypeptide comprising an amino acid sequence set forth in any one of SEQ ID NOs.: 2, 5, 7, 9, 13, 17, and 19, and functional equivalents thereof. Alternatively, a pellet morphology can be promoted by providing an isolated polynucleotide in step 100 that encodes a polypeptide comprising an amino acid sequence set forth in any one of SEQ ID NOs.:23, 25, 2729, and 34, or a functional equivalent thereof; or that encodes an amino acid sequence encoded by polynucleotide SEQ ID NO.: 36 or 37, or a functional equivalent thereof.

In an alternate embodiment of the present invention, a recombinant polynucleotide comprising an antisense oriented complimentary sequence (discussed above) can be utilized for transformation step 120. In a suppression step 140, the RNA produced from transcription of the antisense DNA can form an RNA duplex (dsRNA) with the native mRNA and thereby promote RNA degradation and/or inhibit or block translation of the mRNA. Accordingly, recombinant antisense constructs introduced in step 120 can suppress or block expression of the complimentary gene to promote a desired morphology. For example, a polynucleotide construct comprising, a sequence complimentary to a fragment or an entirety of any of SEQ ID NOs.:1, 4, 6, 8, 12, 16 or 18 can be introduced in step 120. In step 140, the transcript produced from the antisense complimentary sequence can hybridize to mRNA transcribed from genes Balu-4, Balu-42, Brsa-25, Brsa-43, Brsa-47, Brsa-109 or Brsa-118, respectively, and inhibit or block production of the corresponding protein product. Suppression of one or more of Balu-4, Balu-42, Brsa-25, Brsa-43, Brsa-47, Brsa-109 or Brsa-118 by methods in accordance with the present invention can promote pellet morphology in the transformed host. Similarly, polynucleotides having one or more sequences complimentary to a fragment or an entirety of any of SEQ ID NOs.: 22, 24, 26, 28, 33, 36, and 37, can be introduced in step 120, can inhibit or block expression of corresponding gene Arsa-7, Arsa-48, A-37, A-90, Arsa-43, Arsa-10 and Arsa-27. Suppression of one or more of Arsa-7, Arsa-48, A-37, A-90, Arsa-43, Arsa-10 and Arsa-27 in step 140 by methods in accordance with the present invention can promote filamentous morphology in the transformed host.

Figure 24:
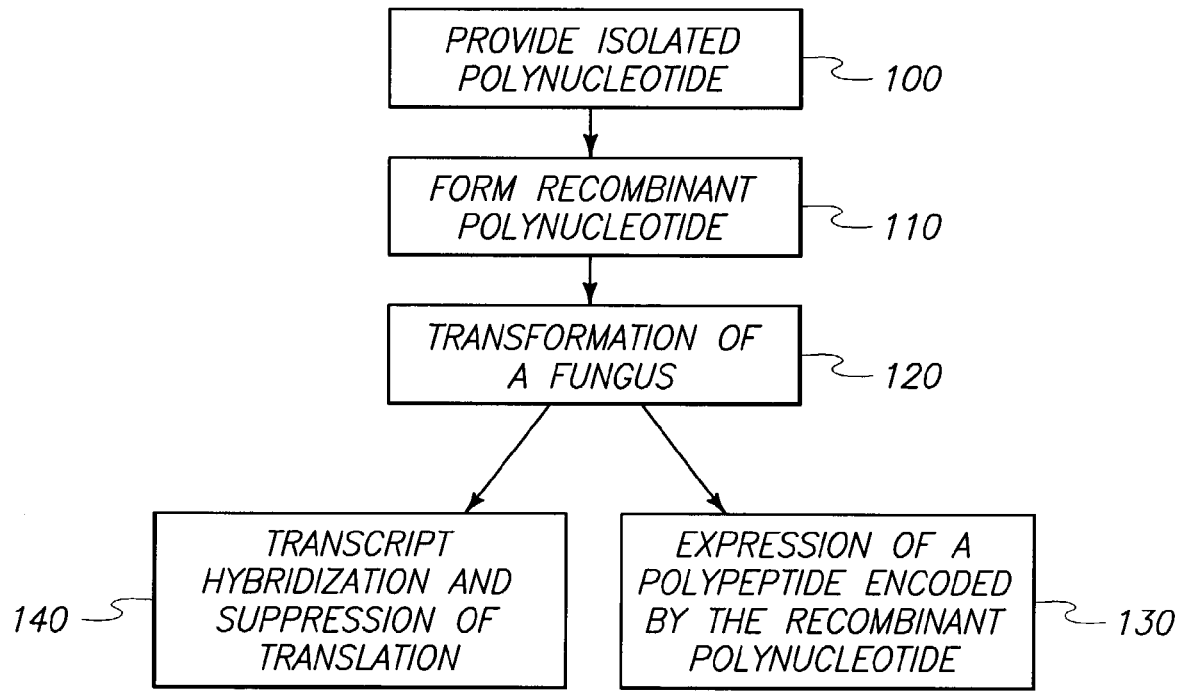
FIG. 24 is a flowchart diagram illustrating a particular aspect of the present invention.

Although the process shown in FIG. 24 was discussed in terms of providing a single isolated polynucleotide in step 100, it is to be understood that the invention encompasses providing two or more of the isolated polynucleotide sequences discussed above. Additionally, it is to be understood that isolated polynucleotide sequences can be provided in step 100 wherein at least one of the isolated polynucleotides provided can promote pellet morphology when expressed and at least one other provided isolated polynucleotide can promote filamentous morphology when expressed. By operably linking differing isolated polynucleotides to differing inducible promoters in step 110, and using multiple recombinant polynucleotides for transformation step 120, it can be possible to selectively promote either the filamentous morphology or the pellet morphology by inducing expression in step 130 or 140.

It can be advantageous to promote a particular morphology in a fungus since utilization of a particular fungus morphology can enhance a bioprocess in a fungus culture. For example, utilization of a pellet form of a fungus can enhance various bioprocesses such as, for example, expressing hemicellulase, expressing cellulase, expressing lignase, converting biomass to alcohol, producing organic acids, producing glucoamylase, producing penicillin and producing lovastatin. Alternatively, utilization of filamentous fungal cultures can enhance bioprocesses such as fumaric acid production or peptic enzyme production.

The process shown in FIG. 24 can be utilized to produce a transformed fungus and to promote a pellet morphology in the transformed fungus which can be utilized to enhance production of a desired product in a culture containing the transformed fungus relative to non-transformed fungus cultures under otherwise identical conditions. Alternatively, the process can be utilized to produce a transformed fungus and to promote a filament morphology in the transformed fungus. The promoted filament morphology can enhance production of a desired product in a culture containing the transformed fungus relative to non-transformed fungus culture under otherwise substantially identical conditions.

The invention also contemplates co-introduction of one or more polynucleotides encoding one or more proteins of interest along with the morphology promoting constructs discussed above. The protein of interest can be native to the host or can be from a different fungal or non-fungal species. Where the protein(s) of interest have increased expression and/or activity in a first morphology relative to a second morphology, the morphology promoting construct co-introduced can preferably promote the first morphology. A protein of interest may be one that can be collected from the culture or can be one that is involved in a bioprocess that produces a desired product or compound.

EXAMPLES

Example 1

General Methods for DNA Isolation and Functional Analysis

*Escherichia coli* (*E. coli*) strains DH5α and JM109 are used as hosts for cloning experiments. *Agrobacterium tumefaciens* strain AGL0 is utilized as host for binary vectors and transformation of *A. niger*.

For isolation of morphology associated genes by suppression subtractive hybridization (SSH), total RNA is isolated from *A. niger* according to the modified acid phenol-guanidinium isothiocyanate-chloroform extraction method described by Chomczynski and Sacch (Anal. Biochem. 162: 156-159 (1987)). The SSH is performed utilizing the PCR-SELECT™ cDNA subtraction kit (CLONTECH, Palo Alto Calif.) as described by the manufacturer, with the exception that the amount of amount of driver cDNA relative to tester utilized was tripled for each of the first and the second hybridizations.

Morphology associated clones are identified by differential screening of SSH cDNA libraries. Two oligonucleotides are designed against each newly isolated clone sequence. Rapid amplification of cDNA and PCR (RACE-PCR) is performed to isolate the 5'-end and the 3'-end of each cDNA clone.

Fungal transformation is achieved utilizing the Bgl II/Xba I pGpdA-hph-TtrpC fragment in pAN7-1 (Punt and van der Hondel, Methods Enzymol. 216: 447-57 (1992)), inserted into binary vector pGA482 (An et al., Binary Vectors" in *Plant Molecular Biology Manual*, Gelvin and Schilperolands (1988), at pp A3/1-19). Introduction of constructs based on pGA482 into *Agrobacterium tumefaciens* strain AGL0 is conducted utilizing the freeze-and-thaw method (Ebert et al., Proc. Natl. Acad. Sci., USA 84: 5745-5749 (1987)). Plasmids are isolated from the transformed *A. tumefaciens*, are digested with various restriction enzymes, and are analyzed utilizing agarose gel electrophoresis to confirm transformation. Fungal transformations are performed as described by Groot et al. (Nat. Biotechnol. 18: 839-42 (1998). At least fifteen independently transformed fungi are selected and grown on agar minimum media containing 250 μg/ml of hygromycin, and 250 μg/ml cefotaxin for each transgenic event.

Example 2

Promoting a Morphology Using Antisense Expression

Individual transgene expression vectors are constructed to comprise polynucleotide sequence complimentary to one the following: Balu-42 (SEQ ID No. 4); Brsa-25 (SEQ ID No.:6); Brsa-118 (SEQ ID No.:18); Arsa-7 (SEQ ID No.:22); A-37 (SEQ ID No.:26); and A-90 (SEQ ID No.:28). The complimentary sequences are incorporated into the vectors in antisense orientation under the control of *A. nidulans* phosphoglyceral dehydrogenase (gpdA) promoter and *A. nidulans* trpC terminator. The constructed vectors are independently introduced into *A. niger* utilizing *Agrobacterium tumefaciens* mediated transformation. Control *A. niger* is prepared by transformation with binary vector without incorporated antisense sequence.

Figure 25:
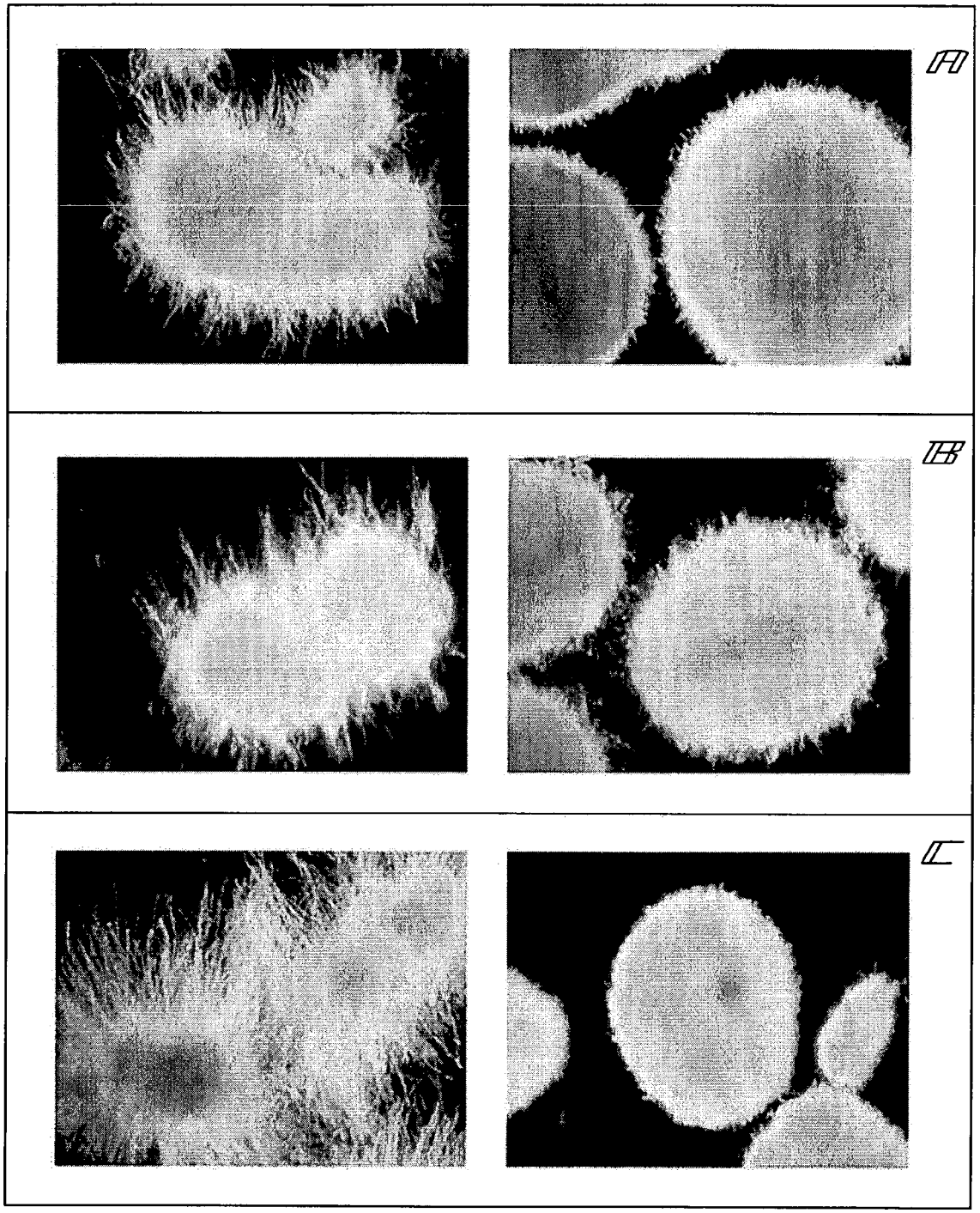
FIG. 25 shows suppression results for *A. niger* transformed with antisense oriented polynucleotide sequences complimentary to Balu-42 (Panel A), Brsa-25 (Panel B) and Brsa-118 (Panel C). Each panel compares morphologies of control *A. niger* (left) and transformed *A. niger* (right) containing the corresponding antisense DNA construct grown in 15 ppb $Mn^{2+}$ medium.

Referring to FIG. 25, such shows the promotion of the pellet morphology in transgenic *A. niger* expressing antisense Balu-42, Brsa-25 and Brsa-118 (right), as compared to control *A. niger* cultured under identical conditions. FIG. 26 shows the promotion of filamentous morphology in transgenic *A. niger* expressing antisense Arsa-7, A-37 and A-90 (right), as compared to control *A. niger* cultured under identical conditions.

Example 3

Morphology Enhanced Bio-production

Transgenic *A. niger* comprising antisense complimentary Balu-42 (strain 2805) or Brsa-118 (strain 2808) is prepared as described in Example 1. Multiple independently transformed cultures of each strain and multiple control cultures (prepared as described above) were grown at 30° C. for about 50 hours. Referring to FIG. 27, Panel A shows the citric acid production for individual cultures of transformed strains 2805 (Balu-42) and 2808 (Brsa-118), and for control *A. niger*. Panel B shows the average citric acid production for cultures of strains 2805 and 2808 relative to control cultures.

The results indicate that the methods and sequences of the invention can be utilized to promote morphology in fungi. The promotion of a morphology by methodology of the invention can be used for enhancing production of protein and/or enhancing a bioprocess utilizing transgenic fungi.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A method of promoting a morphology in a fungus comprising:
   providing a recombinant polynucleotide comprising an antisense orientated sequence that is complementary to a gene coding region that is differentially expressed in a native fungus exhibiting a pellet morphology relative to said native fungus exhibiting a filament morphology wherein the complementary sequence is complementary to an entirety of SEQ ID NO.:4;
   transforming *Aspergillus niger;*
   transcribing the antisense oriented sequence to produce a transcription product of sufficient length to hybridize to a gene coding sequence transcription product to block translation; and
   suppressing expression of the gene coding region utilizing transcription products produced by expression of the recombinant polynucleotide, the suppression promoting a pellet morphology capable of being assumed by the fungi in its native form.

2. A method of enhancing a bioprocess utilizing a fungus, comprising:
   producing a transformed fungus by transforming *Aspergillus niger* with a recombinant polynucleotide molecule comprising a polynucleotide sequence complementary to the entirety of SEQ ID NO.: 4, linked operably to a promoter, the polynucleotide sequence being in antisense orientation;
   transcribing the polynucleotide sequence to produce polynucleotide transcripts; and
   hybridizing the transcripts to mRNA to suppress gene expression and promote pellet morphology, the pellet morphology enhancing a bioprocess relative to the bioprocess utilizing a filamentous morphology of the transformed fungus; the bioprocess comprising production of citric acid.

* * * * *

UNITED STATES PATENT AND TRADEMARK OFFICE
CERTIFICATE OF CORRECTION

PATENT NO.        : 7,439,067 B2                                              Page 1 of 1
APPLICATION NO. : 10/442017
DATED             : October 21, 2008
INVENTOR(S)       : Lasure et al.

It is certified that error appears in the above-identified patent and that said Letters Patent is hereby corrected as shown below:

Column 5, line 52 – Replace "member any of" with --member of any of--.

Column 10, line 44 – Replace "database" with --database.--.

Column 10, line 56 – Replace "Balu-4." with --Balu-4,--.

Column 11, line 31 – Replace "under stood" with --understood--.

Column 12, line 49 – Replace "2729" with --27, 29--.

Column 14, line 20 – Replace "amount of amount of" with --amount of--.

Column 14, line 41 – Replace "(1998)" with --(1989))--.

Column 14, line 52 – Replace "to one the" with --to one of the--.

Signed and Sealed this

Seventeenth Day of March, 2009

JOHN DOLL
*Acting Director of the United States Patent and Trademark Office*

SEQUENCE LISTING

```
<160> NUMBER OF SEQ ID NOS: 37

<210> SEQ ID NO 1
<211> LENGTH: 2208
<212> TYPE: DNA
<213> ORGANISM: Aspergillus niger

<400> SEQUENCE: 1
accgtcaact caatttctcc ccctcaggcc cgtcctccgt ttcacaattg acatcttccc      60
tctccagggg cttgttccgt caagatggcc gacatgtccg gcgaacagat gcaggctaag     120
attaccgcgg ctaggcgcga agccgaaggc ctgaaggaca agatcaagcg cagaaaggat     180
gagttggccg atacgactct ccgtcaagtc gcgcagaacc aaactgaaac cttgcctcgt     240
attggtatga agccccggcg gacgctcaag ggacatttgg ccaagatcta cgccatgcat     300
tggtcgaccg accgccgaca tctcgtctca gcctctcagg acggaaagct catcatctgg     360
gacgcctaca ccacgaacaa ggtccatgcg atcccgctga ggtcatcatg ggtcatgacc     420
tgtgcctatg ccccgagtgg aaactacgtc gcctgcggtg gtctcgacaa catttgctcg     480
atctacaacc tctcctctcg cgagggtccg acccgtgtcg cgcgtgagct ctccggacac     540
tctggctacc tctcttgctg ccggttcatc aacgatcgca gaatcatcac gtcttccggc     600
gacatgactt gcatgctgtg ggatatcgaa tcgggctcga aagttactga attcgctgat     660
caccttggcg acgtgatgtc aatcagcatc aacccgacaa accagaacgt tttcgtttcg     720
ggcgcctgtg atgccttcgc caagctgtgg gacattcgta ccggaaaggc ggtgcaaact     780
ttcgctggac acgaatccga catcaacgcc atccagttct tccccgacgg aaacgctttc     840 ggaacggggtt ccgacgacac ctcctgccgt ctgtttgaca tccgtgcgga tcgcgaactc     900
aacacctacc agagcgacca aatactgtgc ggtatcacct ccgttgcctt ctccgtctct     960
ggcagattgc tttttgctgg ttacgatgac ttcgagtgca aggtctggga tgttctgcgc    1020
ggagacaagg ttggatccct gagtggtcac gagaaccgcg taagctgcct gggagtcagc    1080
aacgatggca tcagcttgtg cactggatcc tgggattctc tgctcaaggt ctgggcttgg    1140
taaaaaagca aaacgaacaa aaacagcaaa gatacccgt ctcagtcttt tgcgacgtcc    1200
tcattccaag tttctctttt tttcctttt ctgcgccact aggctaaatg tccgccattg    1260
tacgataatc ttttcaccg ggagcaaatc ttgtcgccct tgctccataa tgtactatct    1320
cggagtaccg gcaaagttac cacgaaacga aaaaatcacg gggcagtcag ggtgcctaga    1380
```

-continued

```
catgtcgggg ttggggattc tgccgccttt cccagctggg tgtgacgaga aagaataagc    1440
caagaaaaga gcagaatgcc aacaagaacc gacaatgctc gaatactggt gcggtgggtt    1500
gtaataatgc tatttgatgt tgagacctcg ggatcgttgc acggatatca gtgcgttgct    1560
gggcaagagg cagcgcatct cacatgtcat cttttgagct tcgaatattt gcaggcccct    1620
gttcttatgt attcgcgggc ttgactttct acttatgttc cttttctctt cgatctcgct    1680
ttacccttca cccttactaa ccccatcccc ccctccttc gatgtcttgt tctttcttc     1740 aatttcttac ctcgattact accatgatcg agtattcttt tgttcacttt tcattgtttc    1800
cttctcttgc cccctctttt cttctctgac ctttcttact cactatcttc tgtactttt     1860 tgcgggtgat ggatggaaag ggagggaatg tttccggata ggccatgacg ttttctttc     1920 gactcttact gcgatcccct tctgttacta atcatcagcc tacgtcttga aagtgtcggt    1980
tgtgtcattt gagtgttttc aagcgggctt tttttctttt tatatccggt gttgaaatcg    2040
accatgtttc cagcaaatct ttcctttatc cctcgggggt ttcgcccac gatgtcatgt     2100 tccgcgacac tcttatgtcc cgacctggtg gtcagccaag gtgtggcaga gagttgttag    2160
gcagccacta gtacaaatga caggcaatac ttttggtaa aaaaaaaa                 2208
```

<210> SEQ ID NO 2
<211> LENGTH: 352
<212> TYPE: PRT
<213> ORGANISM: Aspergillus niger

<400> SEQUENCE: 2

```
Met Ala Asp Met Ser Gly Glu Gln Met Gln Ala Lys Ile Thr Ala Ala
1               5                   10                  15

Arg Arg Glu Ala Glu Gly Leu Lys Asp Lys Ile Lys Arg Arg Lys Asp
            20                  25                  30

Glu Leu Ala Asp Thr Thr Leu Arg Gln Val Ala Gln Asn Gln Thr Glu
        35                  40                  45

Thr Leu Pro Arg Ile Gly Met Lys Pro Arg Arg Thr Leu Lys Gly His
    50                  55                  60

Leu Ala Lys Ile Tyr Ala Met His Trp Ser Thr Asp Arg Arg His Leu
65                  70                  75                  80

Val Ser Ala Ser Gln Asp Gly Lys Leu Ile Ile Trp Asp Ala Tyr Thr
                85                  90                  95

Thr Asn Lys Val His Ala Ile Pro Leu Arg Ser Ser Trp Val Met Thr
            100                 105                 110

Cys Ala Tyr Ala Pro Ser Gly Asn Tyr Val Ala Cys Gly Gly Leu Asp
        115                 120                 125

Asn Ile Cys Ser Ile Tyr Asn Leu Ser Ser Arg Glu Gly Pro Thr Arg
    130                 135                 140

Val Ala Arg Glu Leu Ser Gly His Ser Gly Tyr Leu Ser Cys Cys Arg
145                 150                 155                 160

Phe Ile Asn Asp Arg Arg Ile Ile Thr Ser Ser Gly Asp Met Thr Cys
                165                 170                 175

Met Leu Trp Asp Ile Glu Ser Gly Ser Lys Val Thr Glu Phe Ala Asp
            180                 185                 190

His Leu Gly Asp Val Met Ser Ile Ser Ile Asn Pro Thr Asn Gln Asn
        195                 200                 205

Val Phe Val Ser Gly Ala Cys Asp Ala Phe Ala Lys Leu Trp Asp Ile
    210                 215                 220
```

```
Arg Thr Gly Lys Ala Val Gln Thr Phe Ala Gly His Glu Ser Asp Ile
225                 230                 235                 240

Asn Ala Ile Gln Phe Phe Pro Asp Gly Asn Ala Phe Gly Thr Gly Ser
            245                 250                 255

Asp Asp Thr Ser Cys Arg Leu Phe Asp Ile Arg Ala Asp Arg Glu Leu
        260                 265                 270

Asn Thr Tyr Gln Ser Asp Gln Ile Leu Cys Gly Ile Thr Ser Val Ala
        275                 280                 285

Phe Ser Val Ser Gly Arg Leu Leu Phe Ala Gly Tyr Asp Asp Phe Glu
    290                 295                 300

Cys Lys Val Trp Asp Val Leu Arg Gly Asp Lys Val Gly Ser Leu Ser
305                 310                 315                 320

Gly His Glu Asn Arg Val Ser Cys Leu Gly Val Ser Asn Asp Gly Ile
                325                 330                 335

Ser Leu Cys Thr Gly Ser Trp Asp Ser Leu Lys Val Trp Ala Trp
            340                 345                 350
```

<210> SEQ ID NO 3
<211> LENGTH: 352
<212> TYPE: PRT
<213> ORGANISM: Emericella nidulans

<400> SEQUENCE: 3

```
Met Ala Asp Met Ser Gly Glu Gln Met Gln Ala Lys Ile Thr Ala Ala
1               5                   10                  15

Arg Arg Glu Ala Glu Gly Leu Lys Asp Lys Ile Arg Arg Arg Lys Asp
            20                  25                  30

Asp Leu Ala Asp Thr Thr Leu Arg Asp Val Ala Gln Asn Gln Thr Asp
        35                  40                  45

Ala Leu Pro Arg Ile Gly Met Lys Pro Arg Arg Thr Leu Lys Gly His
    50                  55                  60

Leu Ala Lys Ile Tyr Ala Met His Trp Ser Thr Asp Arg Arg His Leu
65                  70                  75                  80

Val Ser Ala Ser Gln Asp Gly Lys Leu Ile Ile Trp Asp Ala Tyr Thr
                85                  90                  95

Thr Asn Lys Val His Ala Ile Pro Leu Arg Ser Ser Trp Val Met Thr
            100                 105                 110

Cys Ala Tyr Ala Pro Ser Gly Asn Tyr Val Ala Cys Gly Gly Leu Asp
        115                 120                 125

Asn Ile Cys Ser Ile Tyr Asn Leu Ser Ser Arg Glu Gly Pro Thr Arg
    130                 135                 140

Val Ala Arg Glu Leu Ser Gly His Ser Gly Tyr Leu Ser Cys Cys Arg
145                 150                 155                 160

Phe Ile Asn Asp Arg Arg Ile Ile Thr Ser Ser Gly Asp Met Thr Cys
                165                 170                 175

Met Leu Trp Asp Ile Glu Ser Gly Ser Lys Val Thr Glu Phe Ala Asp
            180                 185                 190

His Phe Gly Asp Val Met Ser Ile Ser Ile Asn Pro Thr Asn Gln Asn
        195                 200                 205

Ile Phe Val Ser Gly Ala Cys Asp Ala Phe Ala Lys Leu Trp Asp Ile
    210                 215                 220

Arg Thr Gly Lys Ala Val Gln Thr Phe Ala Gly His Glu Ser Asp Ile
225                 230                 235                 240

Asn Ala Ile Gln Phe Phe Pro Asp Gly Asn Ala Phe Gly Thr Gly Ser
            245                 250                 255
```

```
Asp Asp Thr Thr Cys Arg Leu Phe Asp Ile Arg Ala Asp Arg Ser Leu
        260                 265                 270

Asn Thr Tyr Gln Ser Asp Gln Ile Leu Cys Gly Ile Thr Ser Val Gly
    275                 280                 285

Phe Ser Val Ser Gly Arg Leu Leu Phe Ala Gly Tyr Asp Asp Phe Glu
    290                 295                 300

Cys Lys Val Trp Asp Val Leu Arg Gly Asp Lys Val Gly Ser Leu Ser
305                 310                 315                 320

Gly His Glu Asn Arg Val Ser Cys Leu Gly Val Ser Asn Asp Gly Ile
                325                 330                 335

Ser Leu Cys Thr Gly Ser Trp Asp Ser Leu Leu Lys Val Trp Ala Trp
                340                 345                 350

<210> SEQ ID NO 4
<211> LENGTH: 1149
<212> TYPE: DNA
<213> ORGANISM: Aspergillus niger

<400> SEQUENCE: 4
acgatttgac gtccctcgcg ttttcgccct ctcccacggt agtcactcct ttgcactaca      60
tacacgaagt cttacttcca gtcactcttt gaaaccactt ctcaatatcc ctacctctta     120
tcattcttta cttcacgcac aagacacgaa agtgaacctg taaaaatgcg tttcttcacc     180
accgccttg  tctctgccct tgcggccctg gcctctgcct acactcagcc cgactactct     240
cagaacccca ccggcaatgc catcctcacc cccgaactga accaggttgt tcctgctggc     300
aagcccttcg agatcacctg gaccccact  acctcgggca ctgtgtctct tgtccttctg     360
cgcggcccca gcaccaacgt cgtccccatc agaccattg  tcgaagacat cgacaactct     420
ggcagttact cttggactcc cagcaccacc ctcgagcctg acaccaccca ctacggtatc     480
ctccttgttg tcgagggcac tggccagtac cagtactccg tccagttcgg catctccaac     540
ccttactact cttcttcttc tctgttgcc  gctgctacta gcaccactgc cgccgccgct     600
gtgagctctg atgcttccga gactagcgtt atcatcagca agatcaccag cactatctgc     660
cccgagactg ccactgccac tgccgacgtc aagcccacct ccgtccctgt ggtcggtggc     720
aacaagccca ccagcttcgt cgttgctccc tctgcctccg gctctgccag ccttatccgc     780
agctctgcca ctccctccgg cactcctgct gccagcagct cctccgtctc tcccgttttc     840
accggtgctg ctgaccgcaa cgccatcagc ctcggcgccg tcgccgtcgg tgtcgctgcc     900
gtccttgctt tctaaatggg gcagccatcc ggcattctta ggaatttgta aagtgatgga     960
ggttgtacct agctgagaca gttgtatgta caagaacgcg caagcgcgag agagtgtgtt    1020
gagattattc atgtttgcag cgattcgatt cgattcgtcg actctttact tatgacaata    1080
taccccata  gttaatgagc aagggtaata ataagagcat tgtattatcc caaaaaaaa    1140
aaaaaaaa                                                            1149

<210> SEQ ID NO 5
<211> LENGTH: 249
<212> TYPE: PRT
<213> ORGANISM: Aspergillus niger

<400> SEQUENCE: 5

Met Arg Phe Phe Thr Thr Ala Leu Val Ser Ala Leu Ala Ala Leu Ala
1               5                   10                  15

Ser Ala Tyr Thr Gln Pro Asp Tyr Ser Gln Asn Pro Thr Gly Asn Ala
```

```
                    20                  25                  30
Ile Leu Thr Pro Glu Leu Asn Gln Val Val Pro Ala Gly Lys Pro Phe
            35                  40                  45

Glu Ile Thr Trp Asp Pro Thr Thr Ser Gly Thr Val Ser Leu Val Leu
    50                  55                  60

Leu Arg Gly Pro Ser Thr Asn Val Val Pro Ile Gln Thr Ile Val Glu
65                  70                  75                  80

Asp Ile Asp Asn Ser Gly Ser Tyr Ser Trp Thr Ser Thr Thr Leu
                85                  90                  95

Glu Pro Asp Thr Thr His Tyr Gly Ile Leu Val Val Glu Gly Thr
                100                 105                 110

Gly Gln Tyr Gln Tyr Ser Val Gln Phe Gly Ile Ser Asn Pro Tyr Tyr
            115                 120                 125

Ser Ser Ser Ser Ser Val Ala Ala Ala Thr Ser Thr Thr Ala Ala Ala
            130                 135                 140

Ala Val Ser Ser Asp Ala Ser Glu Thr Ser Val Ile Ile Ser Lys Ile
145                 150                 155                 160

Thr Ser Thr Ile Cys Pro Glu Thr Ala Thr Ala Thr Ala Asp Val Lys
                165                 170                 175

Pro Thr Ser Val Pro Val Val Gly Gly Asn Lys Pro Thr Ser Phe Val
                180                 185                 190

Val Ala Pro Ser Ala Ser Gly Ser Ala Ser Leu Ile Arg Ser Ser Ala
            195                 200                 205

Thr Pro Ser Gly Thr Pro Ala Ala Ser Ser Ser Val Ser Pro Val
    210                 215                 220

Phe Thr Gly Ala Ala Asp Arg Asn Ala Ile Ser Leu Gly Ala Val Ala
225                 230                 235                 240

Val Gly Val Ala Ala Val Leu Ala Phe
                245

<210> SEQ ID NO 6
<211> LENGTH: 2083
<212> TYPE: DNA
<213> ORGANISM: Aspergillus niger

<400> SEQUENCE: 6
aaagttcgtc ctctattctg tctcccttcg gcgattgtct tcgtcattcg ccttgcttta      60
ccatggccac agaaatcgag ccggccgaga tccctcccgt gctgggagtc ctcccagcat    120
acggacagga taaagaaacc ccctgaggat gatgccacg tgccgatggt gttcgcgctc     180
gcttagatcc gaacgtcacc ctcgaggagt acatgtactg ggccaagatc gagcgtcagc    240
tggaagagga agagaaccgc cagtacgtgc tggagcgcgg gcctctgacc gtcggcaagg    300
tcatccagaa ccgtttctcc aagggcgtcc accatgagaa ggagaagaaa ggcgcccaga    360
atagcccgca gatcgaaggt gaaaagggca tggtcgcatc cactccctca gattcgtccc    420
tagctgttac cgatgaggaa tggagaactg cagctcgcgc cctccgaaca gccagttggg    480
gtaccgtctt ctacttgatt accaccgacg tgctaggctg gcaaacgca ccgttcgtct     540 ttgcaagtgt gggatacggt cctgccgtgg ctttgttcat tgttttttggt tgcttcgccg   600 gcttcagtgg ctggattctg tggaaggtgt ttctagaact cgactcaacg cgctacccct    660
tgatcaactt tggtgacacc tactatcgtg ttttttggagc ttggagtcgt catttggtca   720
acatcggaca gtcgctgcag ctgctgatgt cggtgtccgt gcttgttctg ggtaacggcc    780
agatcctgtc gcagctgtcc aatgaaagta tctgtttcgt ggcgtgcatg attatccatg    840
```

-continued

```
atggtcatcg gcatggtact gtggaagcat tcggtccctt gcagcgtctc ggatggctga      900
ccaacgctgc cgtctggttg aacatcgcgg acttcatcat gatcatggtc gctgctggtg      960
gccactttgg tatcgactat caggccgtca tctcatccac cttgatccag gtcgtcgagc     1020
ccgtcaaggt cttcgctggg ccaccgcccg acaagtatca gattcaggcg acagggttct     1080
cgggacaatt cactggtgtc gaccagatgg tttacagcta cggtggtgct attttatttg     1140
ttgccttcct ggctgaaatg cgccatccgt gggacttctg gagggattg ttgtgcgccc      1200
agatgttcat ttgttttgtc tacatcttct tcggtgcctt tgtctacagc ttctacggcc     1260
aatactccat ctccaacctt tacaacgtgg ttgagccgaa aggtctacaa atggcagtaa     1320
atatagtcta cttttaaca tccattattg cctgcattct ctacttcaat atcggcatga      1380
agtccatcta ccaacaggtc tttatggagc ttctcaactt cccagatatc tccaccaccc     1440
gcggccgcat gctctggtac ggtctcggcc cgatctactg ggtgattgcg ttcgtcatcg     1500
ccgctgccgt gccaaacttt agtggaattt ccagcatggt cggcgcggcc ctgatcctca     1560
acttcaccta cacgctcccg ggtattctat acgttggttt ccgatgccag aaggatgctg     1620
cgctacccgg agaggggtat gatcctgcga ccggggagac ggtgcgccat gattccggca     1680
tgcagcggta tatccgtggg ttcaagaagc actgggtgct gaatcttttc tgtatcttct     1740
acttctgtgg tggattggcg tgttctggta tgggcatgtg ggctgccatt gagagtttga     1800
ttgaggtgtt tgggcccggg ggtacggtgg ctacgtcttt tgggtgtgct gcacctgttt     1860
agaggggaga ttaaaggaga gtgcactgtg gagtagatgg gcactcttga tgagactgtc     1920
tataatatta ttgttagtag atggtgatga tggtatatat gctctcatct ctgtatatgt     1980
ctgtgatggt gtcattatca tgtatggtac gacatggatg tgattttaat gttaatgcta     2040
tgatcttcta tccccaaaaa aaaaaaaaa aaaaaaaaa aaa                         2083
```

<210> SEQ ID NO 7
<211> LENGTH: 599
<212> TYPE: PRT
<213> ORGANISM: Aspergillus niger

<400> SEQUENCE: 7

```
Met Ala Thr Glu Ile Glu Pro Ala Glu Ile Pro Val Leu Gly Val
 1               5                  10                  15

Leu Pro Ala Tyr Gly Gln Asp Lys Glu Thr Pro Leu Arg Met Val Pro
                20                  25                  30

Arg Ala Asp Gly Val Arg Ala Arg Leu Asp Pro Asn Val Thr Leu Glu
            35                  40                  45

Glu Tyr Met Tyr Trp Ala Lys Ile Glu Arg Gln Leu Glu Glu Glu
        50                  55                  60

Asn Arg Gln Tyr Val Leu Glu Arg Gly Pro Leu Thr Val Gly Lys Val
 65                  70                  75                  80

Ile Gln Asn Arg Phe Ser Lys Gly Val His His Glu Lys Glu Lys Lys
                85                  90                  95

Gly Ala Gln Asn Ser Pro Gln Ile Glu Gly Glu Lys Gly Met Val Ala
            100                 105                 110

Ser Thr Pro Ser Asp Ser Ser Leu Ala Val Thr Asp Glu Glu Trp Arg
        115                 120                 125

Thr Ala Ala Arg Ala Leu Arg Thr Ala Ser Trp Gly Thr Val Phe Tyr
    130                 135                 140

Leu Ile Thr Thr Asp Val Leu Gly Trp Ala Asn Ala Pro Phe Val Phe
```

-continued

```
            145                 150                 155                 160
        Ala Ser Val Gly Tyr Gly Pro Ala Val Ala Leu Phe Ile Val Phe Gly
                        165                 170                 175

Cys Phe Ala Gly Phe Ser Gly Trp Ile Leu Trp Lys Val Phe Leu Glu
                        180                 185                 190

Leu Asp Ser Thr Arg Tyr Pro Leu Ile Asn Phe Gly Asp Thr Tyr Tyr
                        195                 200                 205

Arg Val Phe Gly Ala Trp Ser Arg His Leu Val Asn Ile Gly Gln Ser
                        210                 215                 220

Leu Gln Leu Leu Met Ser Val Ser Val Leu Val Leu Gly Asn Gly Gln
        225                 230                 235                 240

Ile Leu Ser Gln Leu Ser Asn Glu Ser Ile Cys Phe Ala Cys Met
                        245                 250                 255

Ile Ile His Asp Gly His Arg His Gly Thr Val Glu Ala Phe Gly Pro
                        260                 265                 270

Leu Gln Arg Leu Gly Trp Leu Thr Asn Ala Ala Val Trp Leu Asn Ile
                        275                 280                 285

Ala Asp Phe Ile Met Ile Met Val Ala Ala Gly Gly His Phe Gly Ile
                        290                 295                 300

Asp Tyr Gln Ala Val Ile Ser Ser Thr Leu Ile Gln Val Val Glu Pro
        305                 310                 315                 320

Val Lys Val Phe Ala Gly Pro Pro Asp Lys Tyr Gln Ile Gln Ala
                        325                 330                 335

Thr Gly Phe Ser Gly Gln Phe Thr Gly Val Asp Gln Met Val Tyr Ser
                        340                 345                 350

Tyr Gly Gly Ala Ile Leu Phe Val Ala Phe Leu Ala Glu Met Arg His
                        355                 360                 365

Pro Trp Asp Phe Trp Lys Gly Leu Leu Cys Ala Gln Met Phe Ile Cys
                        370                 375                 380

Phe Val Tyr Ile Phe Phe Gly Ala Phe Val Tyr Ser Phe Tyr Gly Gln
        385                 390                 395                 400

Tyr Ser Ile Ser Asn Leu Tyr Asn Val Val Glu Pro Lys Gly Leu Gln
                        405                 410                 415

Met Ala Val Asn Ile Val Tyr Phe Leu Thr Ser Ile Ile Ala Cys Ile
                        420                 425                 430

Leu Tyr Phe Asn Ile Gly Met Lys Ser Ile Tyr Gln Gln Val Phe Met
                        435                 440                 445

Glu Leu Leu Asn Phe Pro Asp Ile Ser Thr Thr Arg Gly Arg Met Leu
                        450                 455                 460

Trp Tyr Gly Leu Gly Pro Ile Tyr Trp Val Ile Ala Phe Val Ile Ala
        465                 470                 475                 480

Ala Ala Val Pro Asn Phe Ser Gly Ile Ser Ser Met Val Gly Ala Ala
                        485                 490                 495

Leu Ile Leu Asn Phe Thr Tyr Thr Leu Pro Gly Ile Leu Tyr Val Gly
                        500                 505                 510

Phe Arg Cys Gln Lys Asp Ala Ala Leu Pro Gly Glu Gly Tyr Asp Pro
                        515                 520                 525

Ala Thr Gly Glu Thr Val Arg His Asp Ser Gly Met Gln Arg Tyr Ile
                        530                 535                 540

Arg Gly Phe Lys Lys His Trp Val Leu Asn Leu Phe Cys Ile Phe Tyr
        545                 550                 555                 560

Phe Cys Gly Gly Leu Ala Cys Ser Gly Met Gly Met Trp Ala Ala Ile
                        565                 570                 575
```

Glu Ser Leu Ile Glu Val Phe Gly Pro Gly Gly Thr Val Ala Thr Ser
            580                 585                 590

Phe Gly Cys Ala Ala Pro Val
        595

<210> SEQ ID NO 8
<211> LENGTH: 2006
<212> TYPE: DNA
<213> ORGANISM: Aspergillus niger

<400> SEQUENCE: 8

| | | | | | |
|---|---|---|---|---|---|
| gtgtgttgtc | cctctcaagg | tctccagcat | gcgttcttcc | ggtctctaca | cagcactcct | 60 |
| gtgctccctg | ccgcctcga | ccaacgcgat | tgtccatgaa | aagctcgccg | cggtcccctc | 120 |
| cggctggcat | cacgtcgaag | atgctggctc | cgaccaccag | atcagcctgt | cgatcgcgct | 180 |
| ggcacgcaag | aacctcgatc | agcttgaatc | caagctgaaa | gacttgtcaa | cacctggcga | 240 |
| atcgcaatac | ggccagtggc | tggaccagga | ggatgtcgac | acgctgttcc | cagtggccag | 300 |
| cgacaaggct | gtgattaact | ggctgcgcag | cgccaatatc | cccatatttt | ccgccaggg | 360 |
| cagcttggtg | aactttgcga | ccacggtcga | taaggtgaac | aagcttctca | cgccacctt | 420 |
| tgcctactac | caaagcggct | cttcccagag | attgcgcaca | acagagtact | ccatcccgga | 480 |
| tgatttggtc | gactcaatcg | acctcatctc | cccaacgacg | ttcttcggca | aggaaaagac | 540 |
| tactgctggt | ttgaaccagc | gggcgcaaaa | gattgacaac | catgtggcca | aacgttccaa | 600 |
| cagctcgtcc | tgtgccgatc | tcattacgct | gtcctgcctg | aaggagatgt | acaactttgg | 660 |
| caactacact | cccagcgctt | cgtcgggcag | caagctgggc | ttcggcagct | tcctgaacga | 720 |
| atccgcctcg | tattctgacc | ttgccaagtt | cgagaagctg | tttaacctgc | cctctcagag | 780 |
| cttttccgtg | gagttggtca | acggcggcgt | caatgatcag | aatcaatcga | cggcttcctt | 840 |
| gaccgaggcg | gacctcgatg | tggaattgct | cgtcggagtt | gctcatcccc | tccctgtgac | 900 |
| tgagttcatc | acttctggcg | aacctccttt | cattcccgac | ccgatgagc | cgagtgccgc | 960 |
| cgacaacgag | aacgagcctt | acctccagta | ctatgagtac | ctcctctcca | agcccaactc | 1020 |
| ggctctgccc | caagtgattt | ccaactccta | tggtgacgac | gaacagaccg | ttcccgagta | 1080 |
| ctacgccaag | cgagtctgca | acctgaccgg | acttgttggc | ctgcgcggca | tcagtgtcct | 1140 |
| cgagtcgtcc | ggtgacgaag | gtattggatc | cggctgccga | accaccgacg | gcaccaaccg | 1200 |
| aacccaattc | aacccatct | tcccggccac | ctgtccctac | gtgaccgccg | tgggagggac | 1260 |
| aatgtcctat | gccccgaga | tcgcctggga | agccagttcc | ggcggattca | gcaactactt | 1320 |
| cgagcgggcg | tggttccaga | aggaagctgt | gcagaactac | ctggcgcacc | acatcaccaa | 1380 |
| cgagacgaag | cagtactact | cgcaattcgc | caactttagc | ggtcgcggat | ccctgacgt | 1440 |
| tgctgcccat | agcttcgagc | cttcatatga | ggtgatcttc | tacggcgccc | gctacggctc | 1500 |
| cggcggtacc | tcagccgcgt | gtcccctttt | ctctgcgcta | gtgggcatgt | tgaacgatgc | 1560 |
| tcgtctgcgg | gcgggcaagt | ccacgctggg | tttcttgaac | ccctgctct | acagcaaggg | 1620 |
| gtacagagcg | ttgactgatg | tgacgggggg | ccagtcgatc | ggatgcaatg | gcattgatcc | 1680 |
| gcagaatgat | gagactgttg | ccggcgcggg | cattatcccg | tgggcgcact | ggaacgccac | 1740 |
| ggtcggatgg | gatccggtga | ctggattggg | acttcctgac | tttgagaagt | tgaggcagtt | 1800 |
| ggtgctgtcg | ttgtagatgt | atactatgta | tatggtatga | gatttgtgt | gtgatgtgtg | 1860 |
| atcttatatg | agagagaatg | gtttagactg | tgcgtgatat | acatggacag | ttcatttct | 1920 |

```
catttaatga gacccttcat acggtagggg tcttagaggt cctcccattg ttatgcaaaa   1980
aaaaaaaaaa aaaaaaaaaa aaaaaa                                       2006

<210> SEQ ID NO 9
<211> LENGTH: 595
<212> TYPE: PRT
<213> ORGANISM: Aspergillus niger

<400> SEQUENCE: 9

Met Arg Ser Ser Gly Leu Tyr Thr Ala Leu Leu Cys Ser Leu Ala Ala
1               5                   10                  15

Ser Thr Asn Ala Ile Val His Glu Lys Leu Ala Val Pro Ser Gly
            20                  25                  30

Trp His His Val Glu Asp Ala Gly Ser Asp His Gln Ile Ser Leu Ser
        35                  40                  45

Ile Ala Leu Ala Arg Lys Asn Leu Asp Gln Leu Glu Ser Lys Leu Lys
    50                  55                  60

Asp Leu Ser Thr Pro Gly Glu Ser Gln Tyr Gly Gln Trp Leu Asp Gln
65                  70                  75                  80

Glu Asp Val Asp Thr Leu Phe Pro Val Ala Ser Asp Lys Ala Val Ile
                85                  90                  95

Asn Trp Leu Arg Ser Ala Asn Ile Thr His Ile Ser Arg Gln Gly Ser
            100                 105                 110

Leu Val Asn Phe Ala Thr Thr Val Asp Lys Val Asn Lys Leu Leu Asn
        115                 120                 125

Ala Thr Phe Ala Tyr Tyr Gln Ser Gly Ser Ser Gln Arg Leu Arg Thr
    130                 135                 140

Thr Glu Tyr Ser Ile Pro Asp Asp Leu Val Asp Ser Ile Asp Leu Ile
145                 150                 155                 160

Ser Pro Thr Thr Phe Phe Gly Lys Glu Lys Thr Thr Ala Gly Leu Asn
                165                 170                 175

Gln Arg Ala Gln Lys Ile Asp Asn His Val Ala Lys Arg Ser Asn Ser
            180                 185                 190

Ser Ser Cys Ala Asp Leu Ile Thr Leu Ser Cys Leu Lys Glu Met Tyr
        195                 200                 205

Asn Phe Gly Asn Tyr Thr Pro Ser Ala Ser Ser Gly Ser Lys Leu Gly
    210                 215                 220

Phe Gly Ser Phe Leu Asn Glu Ser Ala Ser Tyr Ser Asp Leu Ala Lys
225                 230                 235                 240

Phe Glu Lys Leu Phe Asn Leu Pro Ser Gln Ser Phe Ser Val Glu Leu
                245                 250                 255

Val Asn Gly Gly Val Asn Asp Gln Asn Gln Ser Thr Ala Ser Leu Thr
            260                 265                 270

Glu Ala Asp Leu Asp Val Glu Leu Leu Val Gly Val Ala His Pro Leu
        275                 280                 285

Pro Val Thr Glu Phe Ile Thr Ser Gly Glu Pro Phe Ile Pro Asp
    290                 295                 300

Pro Asp Glu Pro Ser Ala Ala Asp Glu Asn Glu Pro Tyr Leu Gln
305                 310                 315                 320

Tyr Tyr Glu Tyr Leu Leu Ser Lys Pro Asn Ser Ala Leu Pro Gln Val
                325                 330                 335

Ile Ser Asn Ser Tyr Gly Asp Asp Glu Gln Thr Val Pro Glu Tyr Tyr
            340                 345                 350

Ala Lys Arg Val Cys Asn Leu Thr Gly Leu Val Gly Leu Arg Gly Ile
```

-continued

```
                355                 360                 365
Ser Val Leu Glu Ser Ser Gly Asp Glu Gly Ile Gly Ser Gly Cys Arg
    370                 375                 380

Thr Thr Asp Gly Thr Asn Arg Thr Gln Phe Asn Pro Ile Phe Pro Ala
385                 390                 395                 400

Thr Cys Pro Tyr Val Thr Ala Val Gly Gly Thr Met Ser Tyr Ala Pro
                405                 410                 415

Glu Ile Ala Trp Glu Ala Ser Ser Gly Gly Phe Ser Asn Tyr Phe Glu
                420                 425                 430

Arg Ala Trp Phe Gln Lys Glu Ala Val Gln Asn Tyr Leu Ala His His
                435                 440                 445

Ile Thr Asn Glu Thr Lys Gln Tyr Tyr Ser Gln Phe Ala Asn Phe Ser
            450                 455                 460

Gly Arg Gly Phe Pro Asp Val Ala Ala His Ser Phe Glu Pro Ser Tyr
465                 470                 475                 480

Glu Val Ile Phe Tyr Gly Ala Arg Tyr Gly Ser Gly Thr Ser Ala
                485                 490                 495

Ala Cys Pro Leu Phe Ser Ala Leu Val Gly Met Leu Asn Asp Ala Arg
                500                 505                 510

Leu Arg Ala Gly Lys Ser Thr Leu Gly Phe Leu Asn Pro Leu Leu Tyr
            515                 520                 525

Ser Lys Gly Tyr Arg Ala Leu Thr Asp Val Thr Gly Gly Gln Ser Ile
            530                 535                 540

Gly Cys Asn Gly Ile Asp Pro Gln Asn Asp Glu Thr Val Ala Gly Ala
545                 550                 555                 560

Gly Ile Ile Pro Trp Ala His Trp Asn Ala Thr Val Gly Trp Asp Pro
                565                 570                 575

Val Thr Gly Leu Gly Leu Pro Asp Phe Glu Lys Leu Arg Gln Leu Val
            580                 585                 590

Leu Ser Leu
        595

<210> SEQ ID NO 10
<211> LENGTH: 566
<212> TYPE: PRT
<213> ORGANISM: Aspergillus niger

<400> SEQUENCE: 10

Val Pro Ser Gly Trp His His Val Glu Asp Ala Gly Ser Asp His Gln
1               5                   10                  15

Ile Ser Leu Ser Ile Ala Leu Ala Arg Lys Asn Leu Asp Gln Leu Glu
                20                  25                  30

Ser Lys Leu Lys Asp Leu Ser Thr Pro Gly Glu Ser Gln Tyr Gly Gln
            35                  40                  45

Trp Leu Asp Gln Glu Asp Val Asp Thr Leu Phe Pro Val Ala Ser Asp
        50                  55                  60

Lys Ala Val Ile Asn Trp Leu Arg Ser Ala Asn Ile Thr His Ile Ser
65                  70                  75                  80

Arg Gln Gly Ser Leu Val Asn Phe Ala Thr Thr Val Asp Lys Val Asn
                85                  90                  95

Lys Leu Leu Asn Ala Thr Phe Ala Tyr Tyr Gln Ser Gly Ser Ser Gln
                100                 105                 110

Arg Leu Arg Thr Thr Glu Tyr Ser Ile Pro Asp Asp Leu Val Asp Ser
            115                 120                 125
```

-continued

```
Ile Asp Leu Ile Ser Pro Thr Thr Phe Phe Gly Lys Glu Lys Thr Thr
130                 135                 140

Ala Gly Leu Asn Gln Arg Ala Gln Lys Ile Asp Asn His Val Ala Lys
145                 150                 155                 160

Arg Ser Asn Ser Ser Cys Ala Asp Leu Ile Thr Leu Ser Cys Leu
            165                 170                 175

Lys Glu Met Tyr Asn Phe Gly Asn Tyr Thr Pro Ser Ala Ser Ser Gly
            180                 185                 190

Ser Lys Leu Gly Phe Gly Ser Phe Leu Asn Glu Ser Ala Ser Tyr Ser
        195                 200                 205

Asp Leu Ala Lys Phe Glu Lys Leu Phe Asn Leu Pro Ser Gln Ser Phe
210                 215                 220

Ser Val Glu Leu Val Asn Gly Val Asn Asp Gln Asn Gln Ser Thr
225                 230                 235                 240

Ala Ser Leu Thr Glu Ala Asp Leu Asp Val Glu Leu Leu Val Gly Val
            245                 250                 255

Ala His Pro Leu Pro Val Thr Glu Phe Ile Thr Ser Gly Glu Pro Pro
            260                 265                 270

Phe Ile Pro Asp Pro Asp Glu Pro Ser Ala Ala Asp Asn Glu Asn Glu
            275                 280                 285

Pro Tyr Leu Gln Tyr Tyr Glu Tyr Leu Leu Ser Lys Pro Asn Ser Ala
290                 295                 300

Leu Pro Gln Val Ile Ser Asn Ser Tyr Gly Asp Asp Glu Gln Thr Val
305                 310                 315                 320

Pro Glu Tyr Tyr Ala Lys Arg Val Cys Asn Leu Thr Gly Leu Val Gly
                325                 330                 335

Leu Arg Gly Ile Ser Val Leu Glu Ser Ser Gly Asp Glu Gly Ile Gly
            340                 345                 350

Ser Gly Cys Arg Thr Thr Asp Gly Thr Asn Arg Thr Gln Phe Asn Pro
        355                 360                 365

Ile Phe Pro Ala Thr Cys Pro Tyr Val Thr Ala Val Gly Gly Thr Met
370                 375                 380

Ser Tyr Ala Pro Glu Ile Ala Trp Glu Ala Ser Ser Gly Gly Phe Ser
385                 390                 395                 400

Asn Tyr Phe Glu Arg Ala Trp Phe Gln Lys Glu Ala Val Gln Asn Tyr
                405                 410                 415

Leu Ala His His Ile Thr Asn Glu Thr Lys Gln Tyr Tyr Ser Gln Phe
            420                 425                 430

Ala Asn Phe Ser Gly Arg Gly Phe Pro Asp Val Ala Ala His Ser Phe
        435                 440                 445

Glu Pro Ser Tyr Glu Val Ile Phe Tyr Gly Ala Arg Tyr Gly Ser Gly
450                 455                 460

Gly Thr Ser Ala Ala Cys Pro Leu Phe Ser Ala Leu Val Gly Met Leu
465                 470                 475                 480

Asn Asp Ala Arg Leu Arg Ala Gly Lys Ser Thr Leu Gly Phe Leu Asn
                485                 490                 495

Pro Leu Leu Tyr Ser Lys Gly Tyr Arg Ala Leu Thr Asp Val Thr Gly
            500                 505                 510

Gly Gln Ser Ile Gly Cys Asn Gly Ile Asp Pro Gln Asn Asp Glu Thr
        515                 520                 525

Val Ala Gly Ala Gly Ile Ile Pro Trp Ala His Trp Asn Ala Thr Val
530                 535                 540

Gly Trp Asp Pro Val Thr Gly Leu Gly Leu Pro Asp Phe Glu Lys Leu
```

Arg Gln Leu Val Leu Ser
            565

<210> SEQ ID NO 11
<211> LENGTH: 532
<212> TYPE: PRT
<213> ORGANISM: Homo sapiens

<400> SEQUENCE: 11

Leu Pro Pro Gly Trp Val Ser Leu Gly Arg Ala Asp Pro Glu Glu
1               5                   10                  15

Leu Ser Leu Thr Phe Ala Leu Arg Gln Gln Asn Val Glu Arg Leu Ser
                20                  25                  30

Glu Leu Val Gln Ala Val Ser Asp Pro Ser Ser Pro Gln Tyr Gly Lys
            35                  40                  45

Tyr Leu Thr Leu Glu Asn Val Ala Asp Leu Val Arg Pro Ser Pro Leu
    50                  55                  60

Thr Leu His Thr Val Gln Lys Trp Leu Leu Ala Ala Gly Ala Gln Lys
65                  70                  75                  80

Cys His Ser Val Ile Thr Gln Asp Phe Leu Thr Cys Trp Leu Ser Ile
                85                  90                  95

Arg Gln Ala Glu Leu Leu Pro Gly Ala Glu Phe His His Tyr Val
            100                 105                 110

Gly Gly Pro Thr Glu Thr His Val Val Arg Ser Pro His Pro Tyr Gln
            115                 120                 125

Leu Pro Gln Ala Leu Ala Pro His Val Asp Phe Val Gly Gly Leu His
    130                 135                 140

His Phe Pro Pro Thr Ser Ser Leu Arg Gln Arg Pro Glu Pro Gln Val
145                 150                 155                 160

Thr Gly Thr Val Gly Leu His Leu Gly Val Thr Pro Ser Val Ile Arg
                165                 170                 175

Lys Arg Tyr Asn Leu Thr Ser Gln Asp Val Gly Ser Gly Thr Ser Asn
            180                 185                 190

Asn Ser Gln Ala Cys Ala Gln Phe Leu Glu Gln Tyr Phe His Asp Ser
        195                 200                 205

Asp Leu Ala Gln Phe Met Arg Leu Phe Gly Gly Asn Phe Ala His Gln
    210                 215                 220

Ala Ser Val Ala Arg Val Val Gly Gln Gln Gly Arg Gly Arg Ala Gly
225                 230                 235                 240

Ile Glu Ala Ser Leu Asp Val Gln Tyr Leu Met Ser Ala Gly Ala Asn
                245                 250                 255

Ile Ser Thr Trp Val Tyr Ser Pro Gly Arg His Glu Gly Gln Glu
            260                 265                 270

Pro Phe Leu Gln Trp Leu Met Leu Leu Ser Asn Glu Ser Ala Leu Pro
        275                 280                 285

His Val His Thr Val Ser Tyr Gly Asp Asp Glu Asp Ser Leu Ser Ser
    290                 295                 300

Ala Tyr Ile Gln Arg Val Asn Thr Glu Leu Met Lys Ala Ala Arg
305                 310                 315                 320

Gly Leu Thr Leu Leu Phe Ala Ser Gly Asp Ser Gly Ala Gly Cys Trp
                325                 330                 335

Ser Val Ser Gly Arg His Gln Phe Arg Pro Thr Phe Pro Ala Ser Ser
            340                 345                 350

```
Pro Tyr Val Thr Thr Val Gly Gly Thr Ser Phe Gln Glu Pro Phe Leu
        355                 360                 365

Ile Thr Asn Glu Ile Val Asp Tyr Ile Ser Gly Gly Phe Ser Asn
    370                 375                 380

Val Phe Pro Arg Pro Ser Tyr Gln Glu Glu Ala Val Thr Lys Phe Leu
385                 390                 395                 400

Ser Ser Ser Pro His Leu Pro Pro Ser Ser Tyr Phe Asn Ala Ser Gly
                405                 410                 415

Arg Ala Tyr Pro Asp Val Ala Ala Leu Ser Asp Gly Tyr Trp Val Val
            420                 425                 430

Ser Asn Arg Val Pro Ile Pro Trp Val Ser Gly Thr Ser Ala Ser Thr
        435                 440                 445

Pro Val Phe Gly Gly Ile Leu Ser Leu Ile Asn Glu His Arg Ile Leu
    450                 455                 460

Ser Gly Arg Pro Pro Leu Gly Phe Leu Asn Pro Arg Leu Tyr Gln Gln
465                 470                 475                 480

His Gly Ala Gly Leu Phe Asp Val Thr Arg Gly Cys His Glu Ser Cys
                485                 490                 495

Leu Asp Glu Glu Val Glu Gly Gln Gly Phe Cys Ser Gly Pro Gly Trp
            500                 505                 510

Asp Pro Val Thr Gly Trp Gly Thr Pro Asn Phe Pro Ala Leu Leu Lys
        515                 520                 525

Thr Leu Leu Asn
    530

<210> SEQ ID NO 12
<211> LENGTH: 1991
<212> TYPE: DNA
<213> ORGANISM: Aspergillus niger

<400> SEQUENCE: 12
acccatcaat accttcagtt cgttagcaat cgtcttcccg tcgttcaatt caacttctga      60
tcacactctc tgaggcgtgg tcgaatataa accgtcaaaa ttttcgccac acttcttaac     120
tcgcggcacc acccgttcaa cggccggcgc tcatccaacc gtggtggggc accggactac     180
gcattatacg tccagtaaac aactcgcagt ctgaacactc gtattatctg tctcgcaccc     240
caatctgtca actgtgaaca atggctcccc acgcaagctc ggatgttgct gccaatggcg     300
ccgtgaacgg gtccgctcgt gccaacgctc ctttgtttac cgtcaactcg cccaacgtcg     360
tgtacaccga caatgaaatc agaagccagt atgcttatca taccactgat atcacccgca     420
ctgccgacaa caagctcgtt gccactccca aggccaccaa ctaccacttc aaggtcgacc     480
gcaaggtggg caaggtgggc gtcatgatgg tcggctgggg tggtaacaat ggttccaccg     540
tgacgcaggt atccttgcca accgccgtgg tctcgaatgg agaccgcga gccatgcgcg      600 cctccaacta ctacggctct gtggtcatgg gttccaccat caagctcggt actgacgcca     660
agaccggtga ggagattaac attcctttcc acgacatgct gcccatggtc caccccaatg     720
atctcgctat tggtggctgg gacattagca gcctgaacct tgccgattcc atggaccgtg     780
cccaggtcct ggagcctacc ctcaagcagc aggttcgtaa ggagatggcc gagatgaagc     840
ccctgcctag tatctactac ccggacttta tcgctgccaa ccaggaggac cgggccgaca     900
atgtgctcga gggctccaag gcatgctggg ctcatgttga aagatccag caggacattc     960 gcgacttcaa ggctcagaac ggcctcgaca aggtcatcgt gatgtggact gccaacaccg    1020
agcgttacgc cgacatcctg cctggcgtca atgacacggc cgacaacctc ctcaacgcta    1080
```

-continued

```
tcaagaccgg ccacctggag gtgtccccgt ccactgtctt tgctgtggcc tgtatcctgg    1140
acaacgttcc cttcatcaac ggctctcccc agaacacctt tgttcccggt gccatccagt    1200
tggctgagca gcacaaggcc ttcattggcg gagacgactt caagtctggc cagaccaaaa    1260
tgaagtcggc tctggttgac ttcttgatca acgccggtat caagctcacc tcgattgcca    1320
gctacaacca cctgggcaac aacgacggca agaacttgag ctcccagaag cagttccggt    1380
ccaaggagat ctccaagtcc aacgtggtgg acgacatggt cgcggctaac aagatcctct    1440
acgccgagga cgagcacccc gaccacaccg tggtgatcaa gtacatgcct gcggtgggcg    1500
acaacaagcg cgcgctcgac gagtactacg cggagatctt catgggtggc caccagacca    1560
tcagtctgtt caacatctgc gaggactccc tgctggcgtc tcccttgatc attgatctgg    1620
tgctgattgc ggagatgatg acccgcatca gctggaagtc ggacgaggcg gccgagtaca    1680
agggcttcca gcgtgctc agcgtgctca gctacatgct caaggcgcct ctgactcccc    1740
ctggcactcc tgtggtcaac tcgctgacca agcagcgcag tgccttgacc aacatcttcc    1800
gggcgtgcgt tggactgcag cctgaatccg agatgactct ggagcacaag ctgttctaga    1860
cacccaccta gtaatgctta gccatcatgc taggcgttga tcacactttta cccattgtca    1920 gccaactaca gccactcttt gaatatcagt gactaccttc gaaaaaaaaa aaaaaaaaa    1980 aaaaaaaaaa a                                                         1991
```

<210> SEQ ID NO 13
<211> LENGTH: 532
<212> TYPE: PRT
<213> ORGANISM: Aspergillus niger

<400> SEQUENCE: 13

```
Met Ala Pro His Ala Ser Ser Asp Val Ala Ala Asn Gly Ala Val Asn
1               5                   10                  15

Gly Ser Ala Arg Ala Asn Ala Pro Leu Phe Thr Val Asn Ser Pro Asn
            20                  25                  30

Val Val Tyr Thr Asp Asn Glu Ile Arg Ser Gln Tyr Ala Tyr His Thr
        35                  40                  45

Thr Asp Ile Thr Arg Thr Ala Asp Asn Lys Leu Val Ala Thr Pro Lys
    50                  55                  60

Ala Thr Asn Tyr His Phe Lys Val Asp Arg Lys Val Gly Lys Val Gly
65                  70                  75                  80

Val Met Met Val Gly Trp Gly Asn Asn Gly Ser Thr Val Thr Gln
                85                  90                  95

Val Ser Leu Pro Thr Ala Val Val Ser Asn Gly Arg Pro Arg Ala Met
            100                 105                 110

Arg Ala Ser Asn Tyr Tyr Gly Ser Val Val Met Gly Ser Thr Ile Lys
        115                 120                 125

Leu Gly Thr Asp Ala Lys Thr Gly Glu Glu Ile Asn Ile Pro Phe His
    130                 135                 140

Asp Met Leu Pro Met Val His Pro Asn Asp Leu Ala Ile Gly Gly Trp
145                 150                 155                 160

Asp Ile Ser Ser Leu Asn Leu Ala Asp Ser Met Asp Arg Ala Gln Val
                165                 170                 175

Leu Glu Pro Thr Leu Lys Gln Gln Val Arg Lys Glu Met Ala Glu Met
            180                 185                 190

Lys Pro Leu Pro Ser Ile Tyr Tyr Pro Asp Phe Ile Ala Ala Asn Gln
        195                 200                 205
```

```
Glu Asp Arg Ala Asp Asn Val Leu Glu Gly Ser Lys Ala Cys Trp Ala
    210                 215                 220

His Val Glu Lys Ile Gln Gln Asp Ile Arg Asp Phe Lys Ala Gln Asn
225                 230                 235                 240

Gly Leu Asp Lys Val Ile Val Met Trp Thr Ala Asn Thr Glu Arg Tyr
                245                 250                 255

Ala Asp Ile Leu Pro Gly Val Asn Asp Thr Ala Asp Asn Leu Leu Asn
            260                 265                 270

Ala Ile Lys Thr Gly His Leu Glu Val Ser Pro Ser Thr Val Phe Ala
        275                 280                 285

Val Ala Cys Ile Leu Asp Asn Val Pro Phe Ile Asn Gly Ser Pro Gln
    290                 295                 300

Asn Thr Phe Val Pro Gly Ala Ile Gln Leu Ala Glu Gln His Lys Ala
305                 310                 315                 320

Phe Ile Gly Gly Asp Asp Phe Lys Ser Gly Gln Thr Lys Met Lys Ser
                325                 330                 335

Ala Leu Val Asp Phe Leu Ile Asn Ala Gly Ile Lys Leu Thr Ser Ile
            340                 345                 350

Ala Ser Tyr Asn His Leu Gly Asn Asn Asp Gly Lys Asn Leu Ser Ser
        355                 360                 365

Gln Lys Gln Phe Arg Ser Lys Glu Ile Ser Lys Ser Asn Val Val Asp
    370                 375                 380

Asp Met Val Ala Ala Asn Lys Ile Leu Tyr Ala Glu Asp Glu His Pro
385                 390                 395                 400

Asp His Thr Val Val Ile Lys Tyr Met Pro Ala Val Gly Asp Asn Lys
                405                 410                 415

Arg Ala Leu Asp Glu Tyr Tyr Ala Glu Ile Phe Met Gly Gly His Gln
            420                 425                 430

Thr Ile Ser Leu Phe Asn Ile Cys Glu Asp Ser Leu Leu Ala Ser Pro
        435                 440                 445

Leu Ile Ile Asp Leu Val Leu Ile Ala Glu Met Met Thr Arg Ile Ser
    450                 455                 460

Trp Lys Ser Asp Glu Ala Ala Glu Tyr Lys Gly Phe His Ser Val Leu
465                 470                 475                 480

Ser Val Leu Ser Tyr Met Leu Lys Ala Pro Leu Thr Pro Pro Gly Thr
                485                 490                 495

Pro Val Val Asn Ser Leu Thr Lys Gln Arg Ser Ala Leu Thr Asn Ile
            500                 505                 510

Phe Arg Ala Cys Val Gly Leu Gln Pro Glu Ser Glu Met Thr Leu Glu
        515                 520                 525

His Lys Leu Phe
    530

<210> SEQ ID NO 14
<211> LENGTH: 505
<212> TYPE: PRT
<213> ORGANISM: Aspergillus niger

<400> SEQUENCE: 14

Phe Thr Val Asn Ser Pro Asn Val Val Tyr Thr Asp Asn Glu Ile Arg
1               5                   10                  15

Ser Gln Tyr Ala Tyr His Thr Thr Asp Ile Thr Arg Thr Ala Asp Asn
                20                  25                  30

Lys Leu Val Ala Thr Pro Lys Ala Thr Asn Tyr His Phe Lys Val Asp
```

-continued

```
                35                  40                  45
Arg Lys Val Gly Lys Val Gly Val Met Met Val Gly Trp Gly Gly Asn
 50                  55                  60

Asn Gly Ser Thr Val Thr Gln Val Ser Leu Pro Thr Ala Val Val Ser
 65                  70                  75                  80

Asn Gly Arg Pro Arg Ala Met Arg Ala Ser Asn Tyr Tyr Gly Ser Val
                 85                  90                  95

Val Met Gly Ser Thr Ile Lys Leu Gly Thr Asp Ala Lys Thr Gly Glu
                100                 105                 110

Glu Ile Asn Ile Pro Phe His Asp Met Leu Pro Met Val His Pro Asn
                115                 120                 125

Asp Leu Ala Ile Gly Gly Trp Asp Ile Ser Ser Leu Asn Leu Ala Asp
130                 135                 140

Ser Met Asp Arg Ala Gln Val Leu Glu Pro Thr Leu Lys Gln Gln Val
145                 150                 155                 160

Arg Lys Glu Met Ala Glu Met Lys Pro Leu Pro Ser Ile Tyr Tyr Pro
                165                 170                 175

Asp Phe Ile Ala Ala Asn Gln Glu Asp Arg Ala Asp Asn Val Leu Glu
                180                 185                 190

Gly Ser Lys Ala Cys Trp Ala His Val Glu Lys Ile Gln Gln Asp Ile
                195                 200                 205

Arg Asp Phe Lys Ala Gln Asn Gly Leu Asp Lys Val Ile Val Met Trp
210                 215                 220

Thr Ala Asn Thr Glu Arg Tyr Ala Asp Ile Leu Pro Gly Val Asn Asp
225                 230                 235                 240

Thr Ala Asp Asn Leu Leu Asn Ala Ile Lys Thr Gly His Leu Glu Val
                245                 250                 255

Ser Pro Ser Thr Val Phe Ala Val Ala Cys Ile Leu Asp Asn Val Pro
                260                 265                 270

Phe Ile Asn Gly Ser Pro Gln Asn Thr Phe Val Pro Gly Ala Ile Gln
                275                 280                 285

Leu Ala Glu Gln His Lys Ala Phe Ile Gly Gly Asp Asp Phe Lys Ser
290                 295                 300

Gly Gln Thr Lys Met Lys Ser Ala Leu Val Asp Phe Leu Ile Asn Ala
305                 310                 315                 320

Gly Ile Lys Leu Thr Ser Ile Ala Ser Tyr Asn His Leu Gly Asn Asn
                325                 330                 335

Asp Gly Lys Asn Leu Ser Ser Gln Lys Gln Phe Arg Ser Lys Glu Ile
                340                 345                 350

Ser Lys Ser Asn Val Val Asp Asp Met Val Ala Ala Asn Lys Ile Leu
                355                 360                 365

Tyr Ala Glu Asp Glu His Pro Asp His Thr Val Val Ile Lys Tyr Met
370                 375                 380

Pro Ala Val Gly Asp Asn Lys Arg Ala Leu Asp Glu Tyr Tyr Ala Glu
385                 390                 395                 400

Ile Phe Met Gly Gly His Gln Thr Ile Ser Leu Phe Asn Ile Cys Glu
                405                 410                 415

Asp Ser Leu Leu Ala Ser Pro Leu Ile Asp Leu Val Leu Ile Ala
                420                 425                 430

Glu Met Met Thr Arg Ile Ser Trp Lys Ser Asp Glu Ala Ala Glu Tyr
                435                 440                 445

Lys Gly Phe His Ser Val Leu Ser Val Leu Ser Tyr Met Leu Lys Ala
450                 455                 460
```

```
Pro Leu Thr Pro Pro Gly Thr Pro Val Val Asn Ser Leu Thr Lys Gln
465                 470                 475                 480

Arg Ser Ala Leu Thr Asn Ile Phe Arg Ala Cys Val Gly Leu Gln Pro
                485                 490                 495

Glu Ser Glu Met Thr Leu Glu His Lys
            500                 505

<210> SEQ ID NO 15
<211> LENGTH: 505
<212> TYPE: PRT
<213> ORGANISM: Sesamum indicum

<400> SEQUENCE: 15

Phe Lys Val Glu Ser Pro Asn Val Lys Tyr Thr Glu Gly Glu Ile His
1               5                   10                  15

Ser Val Tyr Asn Tyr Glu Thr Thr Glu Leu Val His Glu Ser Arg Asn
                20                  25                  30

Gly Thr Tyr Gln Trp Ile Val Lys Pro Lys Thr Val Lys Tyr Glu Phe
            35                  40                  45

Lys Thr Asp Thr His Val Pro Lys Leu Gly Val Met Leu Val Gly Trp
50                  55                  60

Gly Gly Asn Asn Gly Ser Thr Leu Thr Gly Gly Val Ile Ala Asn Arg
65                  70                  75                  80

Glu Gly Ile Ser Trp Ala Thr Lys Asp Lys Val Gln Gln Ala Asn Tyr
                85                  90                  95

Phe Gly Ser Leu Thr Gln Ala Ser Ser Ile Arg Val Gly Ser Phe Asn
            100                 105                 110

Gly Glu Glu Ile Tyr Ala Pro Phe Lys Ser Leu Leu Pro Met Val Asn
        115                 120                 125

Pro Asp Asp Val Val Phe Gly Gly Trp Asp Ile Ser Asn Met Asn Leu
    130                 135                 140

Ala Asp Ala Met Gly Arg Ala Lys Val Leu Asp Ile Asp Leu Gln Lys
145                 150                 155                 160

Gln Leu Arg Pro Tyr Met Glu His Met Val Pro Leu Pro Gly Ile Tyr
                165                 170                 175

Asp Pro Asp Phe Ile Ala Ala Asn Gln Gly Ser Arg Ala Asn Asn Val
            180                 185                 190

Ile Lys Gly Thr Lys Lys Glu Gln Val Gln Gln Ile Ile Lys Asp Met
        195                 200                 205

Arg Asp Phe Lys Glu Gln Asn Lys Val Asp Lys Val Val Val Leu Trp
    210                 215                 220

Thr Ala Asn Thr Glu Arg Tyr Ser Asn Val Val Gly Leu Asn Asp
225                 230                 235                 240

Thr Ala Glu Ser Leu Met Ala Ser Val Glu Arg Asn Glu Ala Glu Ile
                245                 250                 255

Ser Pro Ser Thr Leu Tyr Ala Ile Ala Cys Val Phe Glu Asn Val Pro
            260                 265                 270

Phe Ile Asn Gly Ser Pro Gln Asn Thr Phe Val Pro Gly Leu Ile Asp
        275                 280                 285

Leu Ala Ile Gln Arg Asn Ser Leu Ile Gly Gly Asp Asp Phe Lys Ser
    290                 295                 300

Gly Gln Thr Lys Met Lys Ser Val Leu Val Asp Phe Leu Val Gly Ala
305                 310                 315                 320

Gly Ile Lys Pro Thr Ser Ile Val Ser Tyr Asn His Leu Gly Asn Asn
```

```
            325                 330                 335
Asp Gly Met Asn Leu Ser Ala Pro Gln Thr Phe Arg Ser Lys Glu Ile
            340                 345                 350

Ser Lys Ser Asn Val Val Asp Asp Met Val Ala Ser Asn Gly Ile Leu
            355                 360                 365

Tyr Glu Pro Gly Glu His Pro Asp His Ile Val Val Ile Lys Tyr Val
            370                 375             380

Pro Tyr Val Gly Asp Ser Lys Arg Ala Met Asp Glu Tyr Thr Ser Glu
385                 390                 395                 400

Ile Phe Met Gly Gly Lys Ser Thr Ile Val Leu His Asn Thr Cys Glu
                405                 410                 415

Asp Ser Leu Leu Ala Ala Pro Ile Ile Leu Asp Leu Val Leu Leu Ala
                420                 425                 430

Glu Leu Ser Thr Arg Ile Gln Leu Lys Ala Glu Gly Glu Gly Lys Phe
                435                 440                 445

His Ser Phe His Pro Val Ala Thr Ile Leu Ser Tyr Leu Thr Lys Ala
            450                 455                 460

Pro Leu Val Pro Pro Gly Thr Pro Val Val Asn Ala Leu Ser Lys Gln
465                 470                 475                 480

Arg Ala Met Leu Glu Asn Ile Leu Arg Ala Cys Val Gly Leu Ala Pro
                485                 490                 495

Glu Asn Asn Met Ile Leu Glu Tyr Lys
                500                 505

<210> SEQ ID NO 16
<211> LENGTH: 2059
<212> TYPE: DNA
<213> ORGANISM: Aspergillus niger

<400> SEQUENCE: 16
cttttctctt gtcttttccc tcgttcttct ctctttcttc tcttctttct ttctctgctt      60
cggtccagtc tctcgttctt gtctttactg accctagtct ttcgtttcgc gtggtctgtc     120
gtggtgtcgt atcaaatgat tattattatc ttctaaccta tccctctgcc tatttgctat     180
atatccccaa aactgaccca tacatatcac atctctccac ctttggttac atatacatac     240
attcatacat acatatacac ctctcataca acaatgaagg ccactagcgc aacggtggct     300
ttcctagcca ttgctgctgt ccaagcagcc aagcacgccc atgaccatgg ccaccaccgt     360
agccatcgct cggtggatag ccccgtggtc aagaagagtt cctcgtgtca gttcccctcc     420
ggggctggct tgatccccat cactccccac gagaccaatg gtggttgggc gatgagccct     480
gatcaggagt gcaagcctgg cggatattgt ccgtatgctt gtccagccgg ccaggtctcc     540
atgcagtggg acccggaggc tacttcgtac acctacccca tgtccatgaa tggtggactg     600
tactgcgacg agaatggcga aatacagaag ccattcccgg accgtcccta ctgcaaggac     660
ggcacaggcg tcgtcagcgc gaagaacaag tgcaaggagc aggtgtcttt ctgccagact     720
gttcttccgg gcaatgaagc catgccgatc cccacgcttg tggaagagcc ggctaccctg     780
gctgttccgg atctgagtta ctggtgtgag actgcggcgc acttctatat caaccctccg     840
ggatacaaca ccaagactgc ctgtgtctgg ggtacctctg agaaccccta cggcaactgg     900
tccccgtatg ttgccggtgc caacactgac ggcgacggca cacctatgt gaagctcaga     960 tggaacccga tttacctaga accgactacc ccgttccgca acgaagtccc tgagttcggt    1020
gtcgagatcg agtgtgaggg agacggctgc aatggactgc catgcaagat cgacccatcc    1080
```

-continued

```
gtgaacggcg tgaacgagat gactggcgac agctcagtgg gtgcaggcgg tgcatccttc    1140
tgtgtggtgg acggtgccca agggcggaaa ggccaatgtc gttgtcttcg acaagggacg    1200
gcggtggact ctaccagcgt gccggtgtcc agcagcagtg ttagcagcgt cgtcgtgagc    1260
agcagcgcca gcaccagcag cacctcgacc agcagcatcg tccctactac gagcagcacg    1320
ccgacgagtg tcagcaccag caccagcacc agcaccagta ctagcaccag cactagcact    1380
agcactagca gcagcacccc ggccccgacg ccgtccagca ctactactac tatctccagc    1440
accactctca gctccagctc caccatcagc accaccagct ccagcagcat aactccccgg    1500
cccacccccca gctggacgcc ctcttccagc tggaagatca gctcgagcgc agcactgaac    1560
tggaccgtgt cggctagcta cacgtacaag ccacacgtga tggtggagac gggctcctcg    1620
cacacgcagc ctgtagctgc tgctgctgtt gccagtgagg gctcgagcca acgactgga    1680
accgctcaag caacgcagtc agcggttgtg acggagggag ctgctgtcag cactgccgtg    1740
tcgaagctga gtctgattgt ggcagttctt ggagccattg tcatggtcta gacaatagac    1800
catgttgacc atcataccga tcaactgtgt cggttgcata ctcactcacc atcatcactt    1860
ttcttggttc acttctgatg ggcacctttt tcacacttac acttataccc ttatgattga    1920
cgttcttgta tgtgcttgat tgatgagcat ttatcgataa tgtttactgt taatatagtc    1980
attaatttgc ctgtaaattc caagtgccac ttagcacaga gtagaggtcc aaaaaaaaaa    2040
aaaaaaaaaa aaaaaaaaa                                                 2059
```

<210> SEQ ID NO 17
<211> LENGTH: 505
<212> TYPE: PRT
<213> ORGANISM: Aspergillus niger

<400> SEQUENCE: 17

```
Met Lys Ala Thr Ser Ala Thr Val Ala Phe Leu Ala Ile Ala Ala Val
1               5                   10                  15

Gln Ala Ala Lys His Ala His Asp His Gly His His Arg Ser His Arg
            20                  25                  30

Ser Val Asp Ser Pro Val Lys Lys Ser Ser Cys Gln Phe Pro
        35                  40                  45

Ser Gly Ala Gly Leu Ile Pro Ile Thr Pro His Glu Thr Asn Gly Gly
    50                  55                  60

Trp Ala Met Ser Pro Asp Gln Glu Cys Lys Pro Gly Gly Tyr Cys Pro
65                  70                  75                  80

Tyr Ala Cys Pro Ala Gly Gln Val Ser Met Gln Trp Asp Pro Glu Ala
                85                  90                  95

Thr Ser Tyr Thr Tyr Pro Met Ser Met Asn Gly Gly Leu Tyr Cys Asp
            100                 105                 110

Glu Asn Gly Glu Ile Gln Lys Pro Phe Pro Asp Arg Pro Tyr Cys Lys
        115                 120                 125

Asp Gly Thr Gly Val Val Ser Ala Lys Asn Lys Cys Lys Glu Gln Val
    130                 135                 140

Ser Phe Cys Gln Thr Val Leu Pro Gly Asn Glu Ala Met Pro Ile Pro
145                 150                 155                 160

Thr Leu Val Glu Glu Pro Ala Thr Leu Ala Val Pro Asp Leu Ser Tyr
                165                 170                 175

Trp Cys Glu Thr Ala Ala His Phe Tyr Ile Asn Pro Pro Gly Tyr Asn
            180                 185                 190

Thr Lys Thr Ala Cys Val Trp Gly Thr Ser Glu Asn Pro Tyr Gly Asn
```

-continued

```
              195                 200                 205
Trp Ser Pro Tyr Val Ala Gly Ala Asn Thr Asp Gly Asp Gly Asn Thr
    210                 215                 220

Tyr Val Lys Leu Arg Trp Asn Pro Ile Tyr Leu Glu Pro Thr Thr Pro
225                 230                 235                 240

Phe Arg Asn Glu Val Pro Glu Phe Gly Val Glu Ile Glu Cys Glu Gly
            245                 250                 255

Asp Gly Cys Asn Gly Leu Pro Cys Lys Ile Asp Pro Ser Val Asn Gly
            260                 265                 270

Val Asn Glu Met Thr Gly Asp Ser Ser Val Gly Ala Gly Gly Ala Ser
            275                 280                 285

Phe Cys Val Val Asp Gly Ala Gln Gly Arg Lys Gly Gln Cys Arg Cys
    290                 295                 300

Leu Arg Gln Gly Thr Ala Val Asp Ser Thr Ser Val Pro Val Ser Ser
305                 310                 315                 320

Ser Ser Val Ser Ser Val Val Ser Ser Ala Ser Thr Ser Ser
            325                 330                 335

Thr Ser Thr Ser Ser Ile Val Pro Thr Thr Ser Thr Pro Thr Ser
            340                 345                 350

Val Ser Thr Ser Thr Ser Thr Ser Thr Ser Thr Ser Thr Ser
            355                 360                 365

Thr Ser Thr Ser Ser Thr Pro Ala Pro Thr Pro Ser Ser Thr Thr
    370                 375                 380

Thr Thr Ile Ser Ser Thr Thr Leu Ser Ser Ser Thr Ile Ser Thr
385                 390                 395                 400

Thr Ser Ser Ser Ser Ile Thr Pro Arg Pro Thr Pro Ser Trp Thr Pro
            405                 410                 415

Ser Ser Ser Trp Lys Ile Ser Ser Ser Ala Ala Leu Asn Trp Thr Val
            420                 425                 430

Ser Ala Ser Tyr Thr Tyr Lys Pro His Val Met Val Glu Thr Gly Ser
    435                 440                 445

Ser His Thr Gln Pro Val Ala Ala Ala Val Ala Ser Glu Gly Ser
    450                 455                 460

Ser Gln Thr Thr Gly Thr Ala Gln Ala Thr Gln Ser Ala Val Val Thr
465                 470                 475                 480

Glu Gly Ala Ala Val Ser Thr Ala Val Ser Lys Leu Ser Leu Ile Val
            485                 490                 495

Ala Val Leu Gly Ala Ile Val Met Val
            500                 505
```

<210> SEQ ID NO 18
<211> LENGTH: 1904
<212> TYPE: DNA
<213> ORGANISM: Aspergillus niger

<400> SEQUENCE: 18

```
aacaaatttt tctcctctta cctttaatca ttttctttta ttctccttct tccccccat      60
acatcatact ctccgcaata gctctctttc ttgagtgttt tgtgtcttaa actctactgt    120
cccactttcc gcttaatact taccctcct ccttttacac attcaccatg gctgcccgtc    180
ctcagaacat tggtatcaag gccattgagg tctacttccc tcgtcagtgt gtcgaccaga    240
gcgagcttga gaaattcgat ggcgtgagcg aaggcaaata caccattggt cttggtcaga    300
ccaagatgag cttctgtgat gaccgtgaag acatctactc cattgctttg accaccttct    360
```

-continued

```
cctcccttct ccgcaagtac aacatcgacc ccaactccat tggccgcctg gaggtcggta      420
ccgagacctt gctggacaag tccaagtccg tcaagtccgt cctgatgcag cttctggctc      480
cccacggaaa caccaacgtt gagggtgttg acaacgtcaa tgcttgctgc ggtggcacca      540
acgctgtttt caacagcatc aactggctcg agtcctctgc ctgggatggc agagatgccg      600
ttgttgtctg cggtgacatt gccctgtacg ccgagggtgc tgctcgccct accggtggtg      660
ctggctgtgt cgccatgctg atcggtcctg acgcccctat tgtgttcgag cccggtcttc      720
gtgcctccta cgtcacccac gcctacgact tcttcaagcc cgacctgacc agcgagtacc      780
ctgtcgtgga tggtcacttc tccctcagat gctacactga ggctgtcaac gcttgctaca      840
aggcctacaa tgctcgtgag aagaccttga aggagaaggt tcagaacggt accaacggca      900
ccgcccagga cgactcccag actgccttgg accgcttcga atacctctgc taccatgctc      960
ctacctgcaa gctggtgcag aaatccttcg ctcgtatgct gtacaacgac tacctcacaa     1020
acccactca ccctgctttc gccgaagtgg ctcctgagct ccgtgatttg gactacgcca     1080
cctctctcac tgacaagaac gtggagaaga ccttcatggg cctgaccaag aagcgcttcg     1140
ctgagcgtgt taagcccgct ctcgaggttg ccactctttg cggtaacatg tacactgcca     1200
ccgtttgggc tggtctggct agcttgatct ctcacgtccc cttcgatgct agcgagtcca     1260
agcgcatcgg tctcttctcc tacggcagtg gtcttgccag ctccctgctt agcgtaaaga     1320
ttgtcggaga cgtgtccaac ctggtggaga agctcgatct caagaaccgt cttagcaacc     1380
gcaacgttct ccctcctcag tcctacgttg acatgtgtgc cctccgtgag catgctcacc     1440
tcaagaagaa cttcaagcct tccggcaaca ccgagactct ctaccctggt acttactact     1500
tgactgaggt ggacgatatg ttccgccgca agtacgacgt caaggcatga attatgagca     1560
tatgatggac ttgctttcga ccttgcttct ttggacatga ccggttgctt agacggttta     1620
actagattcc cttcagcatg cgcattgttt atttgtggtt cgccttaata gagcttgggg     1680
gcagcggaat gctcctacca atttccgggt ctgcttttct cctttacatt ggttcttaat     1740
gtttcatacg ttgttcatgt atcctcctag ggaggagacc ttctcttgtc cagacaggag     1800
ctggaatgca attatataag acgatgacca ataattccag actcatcaag agtcagaaag     1860
aagagtcatg aaaggaaaaa aaaaaaaaaa aaaaaaaaaa aaaa                       1904
```

<210> SEQ ID NO 19
<211> LENGTH: 460
<212> TYPE: PRT
<213> ORGANISM: Aspergillus niger

<400> SEQUENCE: 19

```
Met Ala Ala Arg Pro Gln Asn Ile Gly Ile Lys Ala Ile Glu Val Tyr
1               5                   10                  15

Phe Pro Arg Gln Cys Val Asp Gln Ser Glu Leu Glu Lys Phe Asp Gly
            20                  25                  30

Val Ser Glu Gly Lys Tyr Thr Ile Gly Leu Gly Gln Thr Lys Met Ser
        35                  40                  45

Phe Cys Asp Asp Arg Glu Asp Ile Tyr Ser Ile Ala Leu Thr Thr Phe
    50                  55                  60

Ser Ser Leu Leu Arg Lys Tyr Asn Ile Asp Pro Asn Ser Ile Gly Arg
65                  70                  75                  80

Leu Glu Val Gly Thr Glu Thr Leu Leu Asp Lys Ser Lys Ser Val Lys
                85                  90                  95

Ser Val Leu Met Gln Leu Leu Ala Pro His Gly Asn Thr Asn Val Glu
```

-continued

```
                100                 105                 110
Gly Val Asp Asn Val Asn Ala Cys Cys Gly Thr Asn Ala Val Phe
            115                 120                 125

Asn Ser Ile Asn Trp Leu Glu Ser Ser Ala Trp Asp Gly Arg Asp Ala
130                 135                 140

Val Val Val Cys Gly Asp Ile Ala Leu Tyr Ala Glu Gly Ala Ala Arg
145                 150                 155                 160

Pro Thr Gly Gly Ala Gly Cys Val Ala Met Leu Ile Gly Pro Asp Ala
                165                 170                 175

Pro Ile Val Phe Glu Pro Gly Leu Arg Ala Ser Tyr Val Thr His Ala
            180                 185                 190

Tyr Asp Phe Phe Lys Pro Asp Leu Thr Ser Glu Tyr Pro Val Val Asp
        195                 200                 205

Gly His Phe Ser Leu Arg Cys Tyr Thr Glu Ala Val Asn Ala Cys Tyr
    210                 215                 220

Lys Ala Tyr Asn Ala Arg Glu Lys Thr Leu Lys Glu Lys Val Gln Asn
225                 230                 235                 240

Gly Thr Asn Gly Thr Ala Gln Asp Asp Ser Gln Thr Ala Leu Asp Arg
                245                 250                 255

Phe Glu Tyr Leu Cys Tyr His Ala Pro Thr Cys Lys Leu Val Gln Lys
            260                 265                 270

Ser Phe Ala Arg Met Leu Tyr Asn Asp Tyr Leu Thr Asn Pro Thr His
        275                 280                 285

Pro Ala Phe Ala Glu Val Ala Pro Glu Leu Arg Asp Leu Asp Tyr Ala
    290                 295                 300

Thr Ser Leu Thr Asp Lys Asn Val Glu Lys Thr Phe Met Gly Leu Thr
305                 310                 315                 320

Lys Lys Arg Phe Ala Glu Arg Val Lys Pro Ala Leu Glu Val Ala Thr
                325                 330                 335

Leu Cys Gly Asn Met Tyr Thr Ala Thr Val Trp Ala Gly Leu Ala Ser
            340                 345                 350

Leu Ile Ser His Val Pro Phe Asp Ala Ser Glu Ser Lys Arg Ile Gly
        355                 360                 365

Leu Phe Ser Tyr Gly Ser Gly Leu Ala Ser Ser Leu Leu Ser Val Lys
    370                 375                 380

Ile Val Gly Asp Val Ser Asn Leu Val Glu Lys Leu Asp Leu Lys Asn
385                 390                 395                 400

Arg Leu Ser Asn Arg Asn Val Leu Pro Pro Gln Ser Tyr Val Asp Met
                405                 410                 415

Cys Ala Leu Arg Glu His Ala His Leu Lys Lys Asn Phe Lys Pro Ser
            420                 425                 430

Gly Asn Thr Glu Thr Leu Tyr Pro Gly Thr Tyr Leu Thr Glu Val
        435                 440                 445

Asp Asp Met Phe Arg Arg Lys Tyr Asp Val Lys Ala
    450                 455                 460

<210> SEQ ID NO 20
<211> LENGTH: 460
<212> TYPE: PRT
<213> ORGANISM: Aspergillus niger

<400> SEQUENCE: 20

Met Ala Ala Arg Pro Gln Asn Ile Gly Ile Lys Ala Ile Glu Val Tyr
1               5                   10                  15
```

-continued

```
Phe Pro Arg Gln Cys Val Asp Gln Ser Glu Leu Glu Lys Phe Asp Gly
             20                  25                  30

Val Ser Glu Gly Lys Tyr Thr Ile Gly Leu Gly Gln Thr Lys Met Ser
         35                  40                  45

Phe Cys Asp Asp Arg Glu Asp Ile Tyr Ser Ile Ala Leu Thr Thr Phe
     50                  55                  60

Ser Ser Leu Leu Arg Lys Tyr Asn Ile Asp Pro Asn Ser Ile Gly Arg
65                  70                  75                  80

Leu Glu Val Gly Thr Glu Thr Leu Leu Asp Lys Ser Lys Ser Val Lys
                 85                  90                  95

Ser Val Leu Met Gln Leu Leu Ala Pro His Gly Asn Thr Asn Val Glu
            100                 105                 110

Gly Val Asp Asn Val Asn Ala Cys Cys Gly Gly Thr Asn Ala Val Phe
        115                 120                 125

Asn Ser Ile Asn Trp Leu Glu Ser Ser Ala Trp Asp Gly Arg Asp Ala
    130                 135                 140

Val Val Val Cys Gly Asp Ile Ala Leu Tyr Ala Glu Gly Ala Ala Arg
145                 150                 155                 160

Pro Thr Gly Gly Ala Gly Cys Val Ala Met Leu Ile Gly Pro Asp Ala
                165                 170                 175

Pro Ile Val Phe Glu Pro Gly Leu Arg Ala Ser Tyr Val Thr His Ala
            180                 185                 190

Tyr Asp Phe Phe Lys Pro Asp Leu Thr Ser Glu Tyr Pro Val Val Asp
        195                 200                 205

Gly His Phe Ser Leu Arg Cys Tyr Thr Glu Ala Val Asn Ala Cys Tyr
    210                 215                 220

Lys Ala Tyr Asn Ala Arg Glu Lys Thr Leu Lys Glu Lys Val Gln Asn
225                 230                 235                 240

Gly Thr Asn Gly Thr Ala Gln Asp Asp Ser Gln Thr Ala Leu Asp Arg
                245                 250                 255

Phe Glu Tyr Leu Cys Tyr His Ala Pro Thr Cys Lys Leu Val Gln Lys
            260                 265                 270

Ser Phe Ala Arg Met Leu Tyr Asn Asp Tyr Leu Thr Asn Pro Thr His
        275                 280                 285

Pro Ala Phe Ala Glu Val Ala Pro Glu Leu Arg Asp Leu Asp Tyr Ala
    290                 295                 300

Thr Ser Leu Thr Asp Lys Asn Val Glu Lys Thr Phe Met Gly Leu Thr
305                 310                 315                 320

Lys Lys Arg Phe Ala Glu Arg Val Lys Pro Ala Leu Glu Val Ala Thr
                325                 330                 335

Leu Cys Gly Asn Met Tyr Thr Ala Thr Val Trp Ala Gly Leu Ala Ser
            340                 345                 350

Leu Ile Ser His Val Pro Phe Asp Ala Ser Glu Ser Lys Arg Ile Gly
        355                 360                 365

Leu Phe Ser Tyr Gly Ser Gly Leu Ala Ser Ser Leu Leu Ser Val Lys
    370                 375                 380

Ile Val Gly Asp Val Ser Asn Leu Val Glu Lys Leu Asp Leu Lys Asn
385                 390                 395                 400

Arg Leu Ser Asn Arg Asn Val Leu Pro Pro Gln Ser Tyr Val Asp Met
                405                 410                 415

Cys Ala Leu Arg Glu His Ala His Leu Lys Lys Asn Phe Lys Pro Ser
            420                 425                 430

Gly Asn Thr Glu Thr Leu Tyr Pro Gly Thr Tyr Tyr Leu Thr Glu Val
```

```
                    435                 440                 445
Asp Asp Met Phe Arg Arg Lys Tyr Asp Val Lys Ala
    450                 455                 460

<210> SEQ ID NO 21
<211> LENGTH: 454
<212> TYPE: PRT
<213> ORGANISM: Neurospora crassa

<400> SEQUENCE: 21

Met Ala Thr Arg Pro Gln Asn Ile Gly Ile Lys Ala Ile Glu Ile Tyr
1               5                   10                  15

Phe Pro Ser Gln Tyr Val Glu Gln Ser Glu Leu Glu Lys Phe Asp Gly
            20                  25                  30

Val Ser Thr Gly Lys Tyr Thr Ile Gly Leu Gly Gln Thr Lys Met Ala
        35                  40                  45

Phe Cys Asp Asp Arg Glu Asp Ile Tyr Ser Leu Ala Leu Thr Ala Val
    50                  55                  60

Ser Arg Leu Leu Lys Asn Tyr Glu Ile Asp Thr Asn Thr Ile Gly Arg
65                  70                  75                  80

Leu Glu Val Gly Thr Glu Thr Leu Leu Asp Lys Ser Lys Ser Val Lys
                85                  90                  95

Ser Val Leu Met Gln Leu Phe Gly Glu Asn Thr Asn Ile Glu Gly Val
            100                 105                 110

Asp Thr Ile Asn Ala Cys Tyr Gly Gly Thr Asn Ala Phe Phe Asn Ser
        115                 120                 125

Val Asn Trp Ile Glu Ser Ser Ala Trp Asp Gly Arg Asp Ala Ile Val
130                 135                 140

Val Ala Gly Asp Ile Ala Leu Tyr Ala Lys Gly Asn Ala Arg Pro Thr
145                 150                 155                 160

Gly Gly Ala Gly Cys Val Ala Met Leu Val Gly Pro Asn Ala Pro Ile
                165                 170                 175

Ala Val Glu Pro Gly Leu Arg Gly Ser Tyr Met Ala His Ala Tyr Asp
            180                 185                 190

Phe Tyr Lys Pro Asp Leu Thr Ser Glu Tyr Pro Tyr Val Asp Gly His
        195                 200                 205

Tyr Ser Val Asn Cys Tyr Thr Glu Ala Leu Asp Gly Ala Tyr Arg Ala
    210                 215                 220

Tyr Asn Gln Arg Glu Lys Leu Leu Thr Asn Gly Val Asn Gly His Ser
225                 230                 235                 240

Glu Asp Ser Thr Lys Thr Pro Leu Asp Arg Phe Asp Tyr Leu Ala Phe
                245                 250                 255

His Ala Pro Thr Cys Lys Leu Val Gln Lys Ser Tyr Ala Arg Leu Leu
            260                 265                 270

Tyr His Asp Tyr Leu Ala Asn Pro Glu Ser Pro Val Phe Ala Asp Val
        275                 280                 285

Pro Pro Glu Val Arg Asp Met Asp Tyr Lys Lys Ser Leu Thr Asp Lys
    290                 295                 300

Val Val Glu Lys Thr Phe Met Thr Leu Thr Lys Lys Arg Phe Gln Glu
305                 310                 315                 320

Arg Val Asn Pro Ala Ile Gln Val Pro Thr Leu Cys Gly Asn Met Tyr
                325                 330                 335

Cys Gly Ser Val Trp Gly Gly Leu Ala Ser Ile Ile Gly His Val Asp
            340                 345                 350
```

```
Ser Ala Gln Leu Glu Gly Lys Arg Ile Gly Leu Phe Ser Tyr Gly Ser
        355                 360                 365
Gly Leu Ala Ala Ser Phe Cys Ser Phe Arg Val Thr Gly Ser Thr Glu
    370                 375                 380
Lys Leu Ala Lys Thr Leu Asn Leu Pro Ala Arg Leu Ala Ala Arg Arg
385                 390                 395                 400
Ala Val Pro Pro Glu Ser Tyr Asp Ala Met Cys Asp Leu Arg Lys Gln
                405                 410                 415
Ala His Leu Gln Lys Asn Tyr Thr Pro Lys Gly Glu Val Ser Thr Leu
            420                 425                 430
Glu Pro Gly Thr Tyr Tyr Leu Glu Asn Val Asp Asp Met Phe Lys Arg
        435                 440                 445
Thr Tyr Ser Ile Lys Ala
        450

<210> SEQ ID NO 22
<211> LENGTH: 1498
<212> TYPE: DNA
<213> ORGANISM: Aspergillus niger

<400> SEQUENCE: 22
agctcaaatt ctcttcccct tgatctcaac taccattcct taagaagctg tgcttcgtac     60
cttcatttcg ccttactttt tttctgctta ctactacaac tccatcactc tctattcttt    120
caatatgaag ttcaccggaa tcgctttcgc cggtcttatc ggttacgctg ccgccctgcc    180
ggccatgggc gcccagcaag actctgctcc caacggtgtt caggccaccg agctcccctc    240
cttccagggt gctgccccct ccggctccct tcttcccctt ccctcgggtg ctcctcaggg    300
ccagggcttc ggaggccagg gcttcggcaa ctctaacggt cagggccagg ctcccaccgt    360
gagcttgggc gatgctcctc agcctcctcc cactggctcc gctgcccctg ctccttctgg    420
agctcctcgt ggccacaaga ggcgtcagct cgagatcccg gcttccgtct ccaacgtccc    480
cgccccgacc ggctccgctg ctgctggagg tgacttcggt ggtgctcctt cgggtcccgc    540
tccctctggt gccgctccct ctggcgtcgc tggtggtgac ggccctctc cttctggttc    600
tttcggtggc cagggcggcc agtctggctc tttcggcggc aacggcgccg ctccctctgg    660
cattgctggc ggcaatggcc cctctacttc cggctctttc ggtggtgccg ctcctccggt    720
gttgctggta gcaatggccc ctctacctcc ggctcttttg gcggccagca gggtcagcag    780
ggccagagcg gcttcggcgg ccaggactcc cagtcccagg ccagtcccca ggactccaag    840
tctcagagct ctaagtccca gaactccagg tctgagggct ctcagtctca ggactcccag    900
tcccagggat ctgactctga gggatctcag ggctctttcg agcagggctc ctcctctgag    960
cagggctctg gctctagctc tttcggtggt aacggtgctg ctccctccgg tgttgctggt   1020
ggcaacggcc cctctccttc cggctctttc ggcggtgctg ctccctccgg tgttgctggc   1080
ggcaacggtc cctctccctc tggctccttc ggcggtaacg gcgctgctcc ctctggcgtc   1140
gctggtggaa acggcccctc tccttccggc tccttcggtg gtaacggtgc tgctccttct   1200
ggtgctgccg gtggtgctcc cgctgcctcg ggcgcccccg ccgccgctcc ctcgggtgct   1260
tcttactaag tccatgcgaa agtcttggac ttcgatcgac aataaacacc ttccatatca   1320
tctgacgctg atgcaatagt tccaccgagg acatcgacaa tgccattgtg tcggcgtgga   1380
ccagaacaac aacaactgga tgaaggtgtg atggattgga cgcttgtgta cattaatcac   1440
tcaataacca gtcattcctt tgaccagatc tggtagaaag aaaaaaaaaa aaaaaaa      1498
```

```
<210> SEQ ID NO 23
<211> LENGTH: 404
<212> TYPE: PRT
<213> ORGANISM: Aspergillus niger

<400> SEQUENCE: 23

Met Lys Phe Thr Gly Ile Ala Phe Ala Gly Leu Ile Gly Tyr Ala Ala
1               5                   10                  15

Ala Leu Pro Ala Met Gly Ala Gln Gln Asp Ser Ala Pro Asn Gly Val
            20                  25                  30

Gln Ala Thr Gly Ala Pro Ser Phe Gln Gly Ala Ala Pro Ser Gly Ser
        35                  40                  45

Pro Leu Pro Leu Pro Ser Gly Ala Pro Gln Gly Gln Gly Phe Gly Gly
    50                  55                  60

Gln Gly Phe Gly Asn Ser Asn Gly Gln Gly Gln Ala Pro Thr Val Ser
65                  70                  75                  80

Leu Gly Asp Ala Pro Gln Pro Pro Thr Gly Ser Ala Ala Pro Ala
                85                  90                  95

Pro Ser Gly Ala Pro Arg Gly His Lys Arg Arg Gln Leu Glu Ile Pro
            100                 105                 110

Ala Ser Val Ser Asn Val Pro Ala Pro Thr Gly Ser Ala Ala Ala Gly
        115                 120                 125

Gly Asp Phe Gly Gly Ala Pro Ser Gly Pro Ala Pro Ser Gly Ala Ala
    130                 135                 140

Pro Ser Gly Val Ala Gly Gly Asp Gly Pro Ser Pro Ser Gly Ser Phe
145                 150                 155                 160

Gly Gly Gln Gly Gly Gln Ser Gly Ser Phe Gly Gly Asn Gly Ala Ala
                165                 170                 175

Pro Ser Gly Ile Ala Gly Gly Asn Gly Pro Ser Thr Ser Gly Ser Phe
            180                 185                 190

Gly Gly Ala Ala Pro Pro Val Leu Leu Val Ala Met Ala Pro Leu Pro
        195                 200                 205

Pro Ala Leu Leu Ala Ala Ser Arg Val Ser Arg Ala Arg Ala Ala Ser
    210                 215                 220

Ala Ala Arg Thr Pro Ser Pro Arg Ala Ser Pro Arg Thr Pro Ser Leu
225                 230                 235                 240

Arg Ala Leu Ser Pro Arg Thr Pro Gly Leu Arg Ala Leu Ser Leu Arg
                245                 250                 255

Thr Pro Ser Pro Arg Asp Leu Thr Leu Arg Asp Leu Arg Ala Leu Ser
            260                 265                 270

Ser Arg Ala Pro Pro Leu Ser Arg Ala Leu Ala Leu Ala Leu Ser Val
        275                 280                 285

Val Thr Val Leu Leu Pro Pro Val Leu Leu Val Ala Thr Ala Pro Leu
    290                 295                 300

Leu Pro Ala Leu Ser Ala Val Leu Leu Pro Val Leu Leu Ala Ala
305                 310                 315                 320

Thr Val Pro Leu Pro Leu Ala Pro Ser Ala Val Thr Ala Leu Leu Pro
                325                 330                 335

Leu Thr Ser Leu Val Glu Thr Ala Pro Leu Leu Pro Ala Pro Ser Val
            340                 345                 350

Val Thr Val Leu Leu Leu Leu Val Leu Pro Val Val Leu Pro Leu Pro
        355                 360                 365

Arg Ala Pro Pro Pro Leu Pro Arg Val Leu Leu Thr Lys Ser Met
    370                 375                 380
```

Arg Lys Ser Trp Thr Ser Ile Asp Asn Lys His Leu Pro Tyr His Leu
385                 390                 395                 400

Thr Leu Met Gln

<210> SEQ ID NO 24
<211> LENGTH: 763
<212> TYPE: DNA
<213> ORGANISM: Aspergillus niger

<400> SEQUENCE: 24
acacaaagca cattccttac attcacattc gtttcttctt cactcctta cttccctatc      60
tttccaatat tcacgatgca gtggacgaac tttctgtgcc ctctgattgc catgcaggct    120
agcctgagtg ctgcctgggg cacccacgtc aagagaggat cggagaccaa tgccaccctg    180
tttgcctatg gacagaactc ttccgcttac cccattgctt atgggctcag tgacggtctt    240
ctctacattg cccaagatcc ggagaacacc gcggcggacc tgacacccat gtcctgggat    300
ctgccctcca tcactgatga gtgctggatt gtcaacggca cgtttatgaa tggcactcgt    360
gcaggatctc tctatatccg accggatagc aacaactgtc ttggcgtgct gccttttgcc    420
caggctaaag gggtgaatgg cgtggtcacg ggctttggcc tctttgcatc gcagctggtc    480
tataacaacg atacccagct ggaagcacag ttctgggcgt cgaagacaga cactgaagat    540
gtctacaaac tggtgtgggt ggaggactct tcgcaaattg cgagcgaaag ctttcccgtc    600
gtggtgaaag cgtccgagga ctcgacctga aaagaacagc gatccaggga ggtgtgactt    660
gggttgttgg ggtggtgctc cgagcatgat gttgttcatt gccattgcgt ggtaatatat    720
ataatagtca ctcgtttata tttgacaaaa aaaaaaaaa aaa                       763

<210> SEQ ID NO 25
<211> LENGTH: 184
<212> TYPE: PRT
<213> ORGANISM: Aspergillus niger

<400> SEQUENCE: 25

Met Gln Trp Thr Asn Phe Leu Cys Pro Leu Ile Ala Met Gln Ala Ser
1               5                   10                  15

Leu Ser Ala Ala Trp Gly Thr His Val Lys Arg Gly Ser Glu Thr Asn
            20                  25                  30

Ala Thr Leu Phe Ala Tyr Gly Gln Asn Ser Ser Ala Tyr Pro Ile Ala
        35                  40                  45

Tyr Gly Leu Ser Asp Gly Leu Leu Tyr Ile Ala Gln Asp Pro Glu Asn
    50                  55                  60

Thr Ala Ala Asp Leu Thr Pro Met Ser Trp Asp Leu Pro Ser Ile Thr
65                  70                  75                  80

Asp Glu Cys Trp Ile Val Asn Gly Thr Phe Met Asn Gly Thr Arg Ala
                85                  90                  95

Gly Ser Leu Tyr Ile Arg Pro Asp Ser Asn Asn Cys Leu Gly Val Leu
            100                 105                 110

Pro Phe Ala Gln Ala Lys Gly Val Asn Gly Val Thr Gly Phe Gly
        115                 120                 125

Leu Phe Ala Ser Gln Leu Val Tyr Asn Asn Asp Thr Gln Leu Glu Ala
    130                 135                 140

Gln Phe Trp Ala Ser Lys Thr Asp Thr Glu Asp Val Tyr Lys Leu Val
145                 150                 155                 160

Trp Val Glu Asp Ser Ser Gln Ile Ala Ser Glu Ser Phe Pro Val Val 165                 170                 175
Val Lys Ala Ser Glu Asp Ser Thr
            180

<210> SEQ ID NO 26
<211> LENGTH: 641
<212> TYPE: DNA
<213> ORGANISM: Aspergillus niger

<400> SEQUENCE: 26
actccacctt ttctcatctg tcctctgtac ctagattcct tcttatatct tatccgtggt    60
tccttctttt ctggccaaga tcttagccat ctatcaacac gagagaaaac ttattcccat   120
cctatcacat acaatgtct gctgctgctc ctcctgctcc cccggttaac ggtgaccggc    180
ccgagacggg tcactcacat ggaaagagtt ccctgtccag caagtcggac ccgaaccagg   240
cgttgagagg tgaagaggct gtgtacagcg ttggatcgag tggattctct ctacgctcaa   300
tgcagcatcg cgaccgtggg ggcaaaatca tcactgaacc cgacttgtcc aaccctaccc   360
gttaccgatt cgagcggccg ctggacacca ttcgatcgtt tgaggcagcc atcgagcgcc   420
gtcgtcgtga ggccatgtaa gatgagactt ggcgtgtgaa tatactgcga atgatgttcg   480
atttcttgtg attatgtttg ggttcggcgc tggacgacgt atggatatgg acatggacat   540
ggatatgagt ttgatttgat tgagcgtgta cattacttca ctgggtatgc ttctggaatg   600
ttaccttgtc gatctcttat ttcaaaaaaa aaaaaaaaaa a                       641

<210> SEQ ID NO 27
<211> LENGTH: 101
<212> TYPE: PRT
<213> ORGANISM: Aspergillus niger

<400> SEQUENCE: 27

Met Ser Ala Ala Ala Pro Pro Ala Pro Val Asn Gly Asp Arg Pro
1               5                   10                  15

Glu Thr Gly His Ser His Gly Lys Ser Ser Leu Ser Ser Lys Ser Asp
            20                  25                  30

Pro Asn Gln Ala Leu Arg Gly Glu Glu Ala Val Tyr Ser Val Gly Ser
        35                  40                  45

Ser Gly Phe Ser Leu Arg Ser Met Gln His Arg Asp Arg Gly Gly Lys
    50                  55                  60

Ile Ile Thr Glu Pro Asp Leu Ser Asn Pro Thr Arg Tyr Arg Phe Glu
65                  70                  75                  80

Arg Pro Leu Asp Thr Ile Arg Ser Phe Glu Ala Ala Ile Glu Arg Arg
                85                  90                  95

Arg Arg Glu Ala Met
            100

<210> SEQ ID NO 28
<211> LENGTH: 1343
<212> TYPE: DNA
<213> ORGANISM: Aspergillus niger

<400> SEQUENCE: 28
cgactggagc acgagggaca ctgacatgga ctgaaggagt agaaaagatc ttcctctccc    60
acctccccag cctttccttc tttgcacctg tgccgtgcac ggtcgagcca ttccttcatt   120
ctttgaacat attgcctggc tccgagtagt ctagcatcca ctccttgcaa gagcactttg   180
agagaaccgg tcttctcata ctcaaaagtt atacatacac atcacttctc tccgaacaaa   240

-continued

```
accgaacaga attcgaagaa cacatacaca atggtctcct tcaagtctct tctgaccgcc    300
accaccctgg ccaccgccgt tctggccatc cctcatagtg gccacggcca tggcagccac    360
aagcaccgtt ccacccatgt cgcctccaag cggacctctt cctccaagcg tggcgctgcc    420
tacaactctg cttccagcgt tcacacgctg acctccggct cctccggcaa cggtaccgtc    480
tcctgggcct acgactggaa catgtacgcc gacggcaccc tccccagtaa cgtcgaatac    540
gtgcccatgc tgtggggcag caagatgttt ggaggctggt tgaccgccat cgagactgcc    600
ctggacagcg gtagcaatta catcatggga ttcaacgagc ctgactcctc ctcccaagcc    660
tcgatgactg cttccgaggc cgccagctcc tacaagaatt acatcactcc ttactctggc    720
aaggctaagc tcgtcacccc ggccgtgacc agtagcacca cggaaggcga gggtctcagc    780
tggatgaagt ccttcctgtc cgaatgcagc gagtgtgaca tgtcggtgct ggcagtccac    840
tggtacggca cctcggccga tgagttcaag tccttcgtgc aggaggccat gcaggtggcg    900
gacgacaacg gattggacga gacctgggtg acagaattcg ccctcaccag cgacgagtct    960
gccggcggcg atgagagttc agcggcggac ttccttgacg aagttttgcc gtggttggac   1020
agccagagtg gcgtgggacg gtatgcgtat tacatgtgtg cagatgggta tctgctcagc   1080
ggggaggagt tgagctcgag tggaaaggtc tacgttgcat agaacaacca actaccttttg  1140
gattccatta gatctgcttt accttggact tttatcccgt gataccttttt tgtgctgttt  1200
tttattctat tccattctac catccatctc tcacctaaga gggaagagaa gacggacaac   1260
cccatttttac ccacccactt tactttccaa tatattacaa ttccaatttg aatcaaattc   1320
aaatccaaaa aaaaaaaaaa aaa                                           1343
```

<210> SEQ ID NO 29
<211> LENGTH: 283
<212> TYPE: PRT
<213> ORGANISM: Aspergillus niger
<220> FEATURE:
<221> NAME/KEY: MISC_FEATURE
<223> OTHER INFORMATION: X = gap in homologous sequence

<400> SEQUENCE: 29

```
Met Val Ser Phe Lys Ser Leu Leu Thr Ala Thr Thr Leu Ala Thr Ala
1               5                   10                  15

Val Leu Ala Ile Pro His Ser Gly His Gly His Gly Ser His Lys His
                20                  25                  30

Arg Ser Thr His Val Ala Ser Lys Arg Thr Ser Ser Lys Arg Gly
            35                  40                  45

Ala Ala Tyr Asn Ser Ala Ser Ser Val His Thr Leu Thr Ser Gly Ser
        50                  55                  60

Ser Gly Asn Gly Thr Val Ser Trp Ala Tyr Asp Trp Asn Met Tyr Ala
65                  70                  75                  80

Asp Gly Thr Leu Pro Ser Asn Val Glu Tyr Val Pro Met Leu Trp Gly
                85                  90                  95

Ser Lys Met Phe Gly Gly Trp Leu Thr Ala Ile Glu Thr Ala Leu Asp
                100                 105                 110

Ser Gly Ser Asn Tyr Ile Met Gly Phe Asn Glu Pro Asp Ser Ser Ser
            115                 120                 125

Gln Ala Ser Met Thr Ala Ser Glu Ala Ala Ser Ser Tyr Lys Asn Tyr
        130                 135                 140

Ile Thr Pro Tyr Ser Gly Lys Ala Lys Leu Val Thr Pro Ala Val Thr
145                 150                 155                 160
```

```
Ser Ser Thr Thr Glu Gly Glu Gly Leu Ser Trp Met Lys Ser Phe Leu
            165                 170                 175

Ser Glu Cys Ser Glu Cys Asp Met Ser Val Leu Ala Val His Trp Tyr
        180                 185                 190

Gly Thr Ser Ala Asp Glu Phe Lys Ser Phe Val Gln Glu Ala Met Gln
    195                 200                 205

Val Ala Asp Asp Asn Gly Leu Asp Glu Thr Trp Val Thr Glu Phe Ala
    210                 215                 220

Leu Thr Ser Asp Glu Ser Ala Gly Gly Asp Glu Ser Ser Ala Ala Asp
225                 230                 235                 240

Phe Leu Asp Glu Val Leu Pro Trp Leu Asp Ser Gln Ser Gly Val Gly
            245                 250                 255

Arg Tyr Ala Tyr Tyr Met Cys Ala Asp Gly Tyr Leu Leu Ser Gly Glu
            260                 265                 270

Glu Leu Ser Ser Ser Gly Lys Val Tyr Val Ala
        275                 280

<210> SEQ ID NO 30
<211> LENGTH: 22
<212> TYPE: PRT
<213> ORGANISM: Aspergillus niger

<400> SEQUENCE: 30

Lys Arg Arg Lys Asp Glu Leu Ala Asp Thr Thr Leu Arg Gln Val Ala
1               5                   10                  15

Gln Asn Gln Thr Glu Thr
            20

<210> SEQ ID NO 31
<211> LENGTH: 16
<212> TYPE: PRT
<213> ORGANISM: Aspergillus niger

<400> SEQUENCE: 31

Leu Gly Asp Val Met Ser Ile Ser Ile Asn Pro Thr Asn Gln Asn Val
1               5                   10                  15

<210> SEQ ID NO 32
<211> LENGTH: 29
<212> TYPE: PRT
<213> ORGANISM: Aspergillus niger

<400> SEQUENCE: 32

Ser Cys Arg Leu Phe Asp Ile Arg Ala Asp Arg Glu Leu Asn Thr Tyr
1               5                   10                  15

Gln Ser Asp Gln Ile Leu Cys Gly Ile Thr Ser Val Ala
            20                  25

<210> SEQ ID NO 33
<211> LENGTH: 1221
<212> TYPE: DNA
<213> ORGANISM: Aspergillus niger

<400> SEQUENCE: 33
taccactcac ctttcgcgca tcgccatctg cgatcctccc cacaacactc cacctagata      60
catacaccat taactgcgct tctacaacat gcagatcttc gttaagaccc tcaccggcaa     120
gacaatcacc ctcgaggtcg agtccagcga taccatcgac aacgtcaaga ccaagatcca     180
ggataaggag ggcatccctc ccgaccagca gcgtctgatc ttcgccggaa agcagctgga     240
```

-continued

```
ggatggccgc acgcttagtg actacaacat ccagaaggag tctactctcc atcttgtcct    300
ccgcctgcgt ggtggtatgc agattttcgt caagaccctg accggaaaga ccatcaccct    360
tgaggtggag tcttctgaca ccatcgacaa tgtgaagacc aagattcagg acaaggaggg    420
cattcccccg gaccagcagc gtctgatctt cgctggaaag cagctggagg atggccgtac    480
cctgtctgac tacaacattc aaaaggaatc caccctccac ctcgtccttc gtctgcgtgg    540
tggtatgcag atcttcgtca agactctcac gggaaagacg atcacattgg aagttgaatc    600
ttccgacaca attgataacg ttaagaccaa gattcaagac aaggaaggca tcccccccgga   660
ccagcagcgt ttgatcttcg ctggtaagca gttggaggat ggccgtacct tgtccgacta    720
caacatccag aaagaatcca ctcttcacct tgtccttcgt ctccgtggtg gtatgcagat    780
cttcgtgaag actcttaccg gcaagacgat tacgctggag gtggagagct cggataccat    840
tgataacgtc aagactaaga ttcaagataa ggagggcatt cccccggacc agcagcgtct    900
catcttcgct ggtaagcagt tggaagatgg acgtacgctc tccgattaca acatccagaa    960
ggagagcact ctgcacctgg tgctccgtct ccgtggcgga aactaatgcc ttattttgat   1020
cttcttcttt tagcacggct catctacggt tgagtggcct gcatggcgtt gggacggttg   1080
ttttcatcgg tttttatgat acggataaat tgggcatacc ttagggtcac catcttccat   1140
ggtgccttgc gtcattcttt tacctaggaa tcaattcaat aatcatattc cacctgatat   1200
ctaaaaaaaa aaaaaaaacc t                                              1221
```

<210> SEQ ID NO 34
<211> LENGTH: 236
<212> TYPE: PRT
<213> ORGANISM: Aspergillus niger

<400> SEQUENCE: 34

```
Val Leu Arg Leu Arg Gly Gly Met Gln Ile Phe Val Lys Thr Leu Thr
1               5                   10                  15

Gly Lys Thr Ile Thr Leu Glu Val Glu Ser Ser Asp Thr Ile Asp Asn
            20                  25                  30

Val Lys Thr Lys Ile Gln Asp Lys Glu Gly Ile Pro Pro Asp Gln Gln
        35                  40                  45

Arg Leu Ile Phe Ala Gly Lys Gln Leu Glu Asp Gly Arg Thr Leu Ser
    50                  55                  60

Asp Tyr Asn Ile Gln Lys Glu Ser Thr Leu His Leu Val Leu Arg Leu
65                  70                  75                  80

Arg Gly Gly Met Gln Ile Phe Val Lys Thr Leu Thr Gly Lys Thr Ile
                85                  90                  95

Thr Leu Glu Val Glu Ser Ser Asp Thr Ile Asp Asn Val Lys Thr Lys
            100                 105                 110

Ile Gln Asp Lys Glu Gly Ile Pro Pro Asp Gln Gln Arg Leu Ile Phe
        115                 120                 125

Ala Gly Lys Gln Leu Glu Asp Gly Arg Thr Leu Ser Asp Tyr Asn Ile
    130                 135                 140

Gln Lys Glu Ser Thr Leu His Leu Val Leu Arg Leu Arg Gly Gly Met
145                 150                 155                 160

Gln Ile Phe Val Lys Thr Leu Thr Gly Lys Thr Ile Thr Leu Glu Val
                165                 170                 175

Glu Ser Ser Asp Thr Ile Asp Asn Val Lys Thr Lys Ile Gln Asp Lys
            180                 185                 190
```

Glu Gly Ile Pro Pro Asp Gln Gln Arg Leu Ile Phe Ala Gly Lys Gln
        195                 200                 205

Leu Glu Asp Gly Arg Thr Leu Ser Asp Tyr Asn Ile Gln Lys Glu Ser
    210                 215                 220

Thr Leu His Leu Val Leu Arg Leu Arg Gly Gly Asn
225                 230                 235

<210> SEQ ID NO 35
<211> LENGTH: 235
<212> TYPE: PRT
<213> ORGANISM: Aspergillus niger

<400> SEQUENCE: 35

Val Leu Arg His Ala Asn Asn Leu Ala Val Val Lys Thr Leu Thr Gly
1               5                   10                  15

Lys Thr Ile Thr Leu Glu Val Glu Ser Ser Asp Thr Ile Asp Asn Val
            20                  25                  30

Lys Thr Lys Ile Gln Asp Lys Glu Gly Ile Pro Pro Asp Gln Gln Arg
        35                  40                  45

Leu Ile Phe Ala Gly Lys Gln Leu Glu Asp Gly Arg Thr Leu Ser Asp
    50                  55                  60

Tyr Asn Ile Gln Lys Glu Ser Thr Leu His Leu Val Leu Arg Leu Arg
65                  70                  75                  80

Gly Gly Met Gln Ile Phe Val Lys Thr Leu Thr Gly Lys Thr Ile Thr
                85                  90                  95

Leu Glu Val Glu Ser Ser Asp Thr Ile Asp Asn Val Lys Ser Lys Ile
            100                 105                 110

Gln Asp Lys Glu Gly Ile Pro Pro Asp Gln Gln Arg Leu Ile Phe Ala
        115                 120                 125

Gly Lys Gln Leu Glu Asp Gly Arg Thr Leu Ser Asp Tyr Asn Ile Gln
    130                 135                 140

Lys Glu Ser Thr Leu His Leu Val Leu Arg Leu Arg Gly Gly Met Gln
145                 150                 155                 160

Ile Phe Val Lys Thr Leu Thr Gly Lys Thr Ile Thr Leu Glu Val Glu
                165                 170                 175

Ser Ser Asp Thr Ile Asp Asn Val Lys Thr Lys Ile Gln Asp Lys Glu
            180                 185                 190

Gly Ile Pro Pro Asp Gln Gln Arg Leu Ile Phe Ala Gly Lys Gln Leu
        195                 200                 205

Glu Asp Gly Arg Thr Leu Ser Asp Tyr Asn Ile Gln Lys Glu Ser Thr
    210                 215                 220

Leu His Leu Val Leu Arg Leu Arg Gly Gly Asn
225                 230                 235

<210> SEQ ID NO 36
<211> LENGTH: 404
<212> TYPE: DNA
<213> ORGANISM: Aspergillus niger

<400> SEQUENCE: 36
tcgagcggcc gccgggcagg tacctcccctt atgctgctgg atgaagacgt ggttactgcc     60
tactatgcgc aagttcccaa ctcggtctac gtgagcagtg ccgtggttaa catctacccc    120
tgcaacacca ctcttcccag cttctcgctt gtcctcggcg agtcgagcct ggccacgatc    180
cccggtaacc tgatcaattt ctccaaggtt ggcaccaaca ccaccaccgg acaggccttg    240
tgctttggcg gcattcaatc caacggaaac acctcgctgc agattctggg cgatattttc    300

-continued

```
ctgaaggcct ttttcgttgt cttcgacatg cgcggcccct cgcttggtgt tgcctctccc      360
aagaactagt ttccttttcc tgtacctcgg ccgcgaccac gcta                        404

<210> SEQ ID NO 37
<211> LENGTH: 334
<212> TYPE: DNA
<213> ORGANISM: Aspergillus niger

<400> SEQUENCE: 37
acaaagaatt ctccaggact cttgtctgac gtaaaatagg aagaaaagga aaactgaggt        60
gatatcgcct gtgtagtgcg gcgattgacg tccttcctcc gcttgcccag cggtggtggg      120
tcgagctgag gtgtccgttt atacgtgatg gtagtggtca cgatatggcg cacacaaaag      180
gtgtttccat tctcactgac gggtgattcg aagaagcgct gtcccggtc tgatggagta       240 aaagggaac ggaggggtg cgcactccgc ggggacgcag acactggggt aatagaggta       300
tggtgcagga aggcgcatgc gctgggcatg aata                                  334
```